(12) United States Patent
Bryan et al.

(10) Patent No.: US 12,178,986 B2
(45) Date of Patent: Dec. 31, 2024

(54) CONNECTOR

(71) Applicant: Aseptic Connectors Limited, Tring (GB)

(72) Inventors: Matthew Robert Bryan, Tring (GB); Alistair Richard Ian Wilson, Tring (GB)

(73) Assignee: Aseptic Connectors Limited, Tring (GB)

( * ) Notice: Subject to any disclaimer, the term of this patent is extended or adjusted under 35 U.S.C. 154(b) by 0 days.

(21) Appl. No.: 18/031,537

(22) PCT Filed: Dec. 13, 2021

(86) PCT No.: PCT/EP2021/085552
§ 371 (c)(1),
(2) Date: Apr. 12, 2023

(87) PCT Pub. No.: WO2022/128954
PCT Pub. Date: Jun. 23, 2022

(65) Prior Publication Data
US 2023/0372692 A1 Nov. 23, 2023

(30) Foreign Application Priority Data

Dec. 17, 2020 (GB) ...................................... 2020053
Sep. 23, 2021 (GB) ...................................... 2113596

(51) Int. Cl.
*A61M 39/18* (2006.01)
*A61M 39/10* (2006.01)
*A61M 39/16* (2006.01)

(52) U.S. Cl.
CPC .................................. *A61M 39/18* (2013.01)

(58) Field of Classification Search
CPC ...... A61M 39/18; A61M 39/10; A61M 39/00; A61M 39/1016; A61M 2039/1016
See application file for complete search history.

(56) References Cited

U.S. PATENT DOCUMENTS

| 4,157,723 A | 6/1979 | Granzow et al. |
| 4,340,097 A | 7/1982 | Ammann et al. |

(Continued)

FOREIGN PATENT DOCUMENTS

| EP | 02563803 B1 | 7/1989 |
| WO | WO 2021/040830 A1 | 3/2021 |
| WO | WO 2021/252190 A1 | 12/2021 |

OTHER PUBLICATIONS

International Search Report and Written Opinion for Application No. PCT/EP2021/085552, mailed Feb. 23, 2022.

(Continued)

*Primary Examiner* — Robert J Utama
*Assistant Examiner* — Hamza A Darb
(74) *Attorney, Agent, or Firm* — Wolf, Greenfield & Sacks, P.C.

(57) ABSTRACT

A connector adapted for forming a fluid flow pathway therethrough by connection with a reciprocal connector, wherein both the connector and the reciprocal connector each comprise a fluid flow passageway part (11A) defining a fluid flow opening, a socket part (12A) located upon the fluid flow passageway part adjacent to the fluid flow opening, a plug part (13A) located upon the fluid flow passageway part adjacent to the fluid flow opening and spaced from the socket part in a direction crossing the fluid flow opening, wherein the socket part of the connector is configured to receive therein the plug part of said reciprocal connector to connect thereto such that the fluid flow opening of the connector is aligned in register with the fluid flow opening of the reciprocal connector and, a closure part (14A) arranged to openably close the fluid flow opening of the connector and to receive an urging force from said received plug part of the reciprocal connector thereby to be displaced in a direction crossing the fluid flow opening to uncover the fluid flow opening such that the connector is thereby con- (Continued)

nectable to the reciprocal connector with respective fluid flow openings in fluid communication.

15 Claims, 37 Drawing Sheets

(56) References Cited

U.S. PATENT DOCUMENTS

| | | |
|---|---|---|
| 2006/0252298 A1 | 11/2006 | Biddel et al. |
| 2012/0042971 A1 | 2/2012 | Py |
| 2019/0224467 A1* | 7/2019 | Zhang .................... F16L 37/28 |
| 2020/0289812 A1 | 9/2020 | Ciccone et al. |
| 2021/0386622 A1 | 12/2021 | Cornelius et al. |

OTHER PUBLICATIONS

International Preliminary Report on Patentability for Application No. PCT/EP2021/085552, mailed Jun. 29, 2023.

* cited by examiner

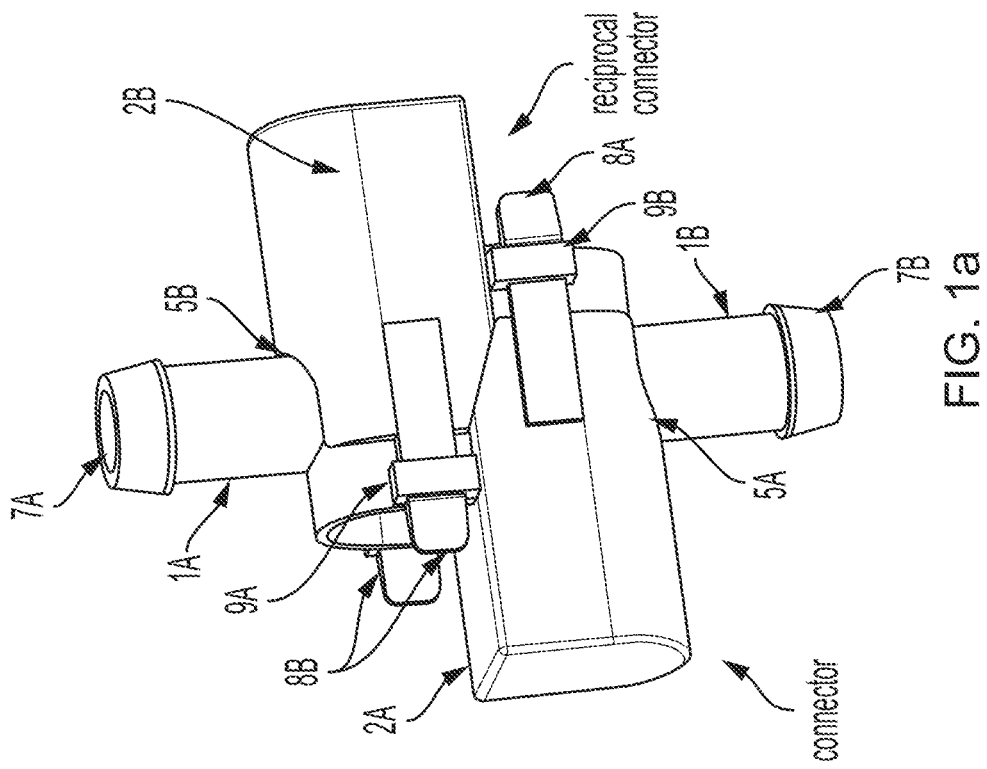
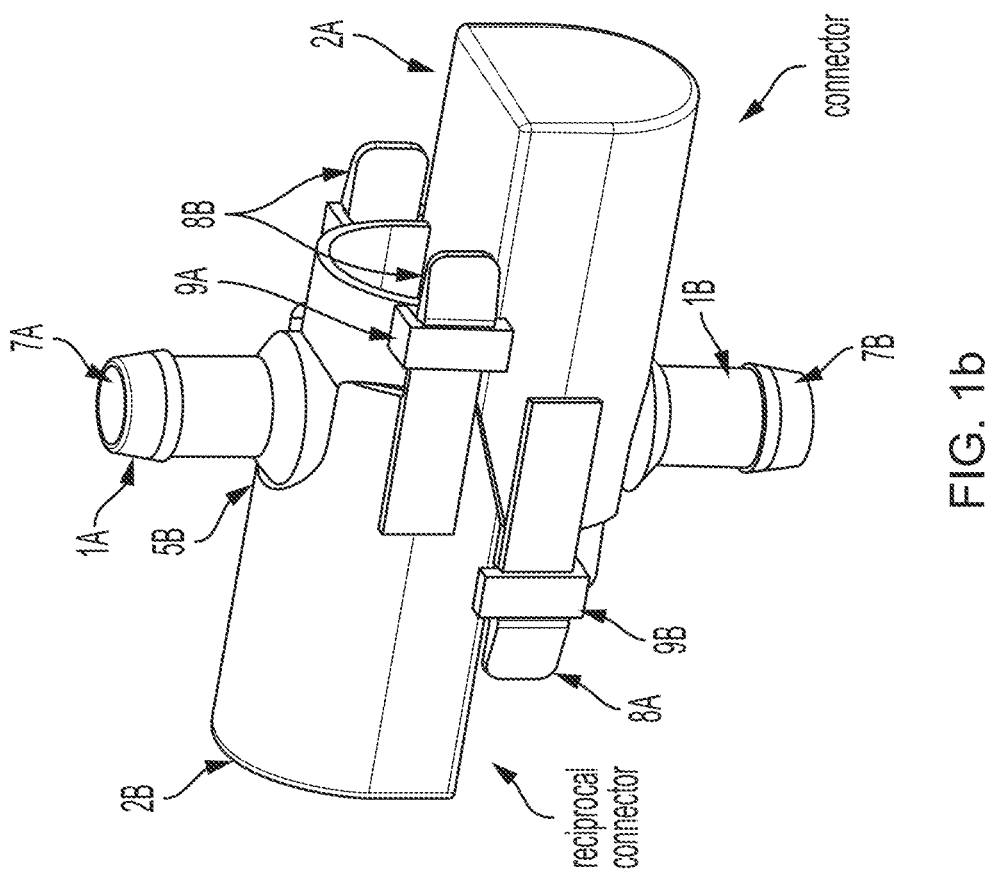

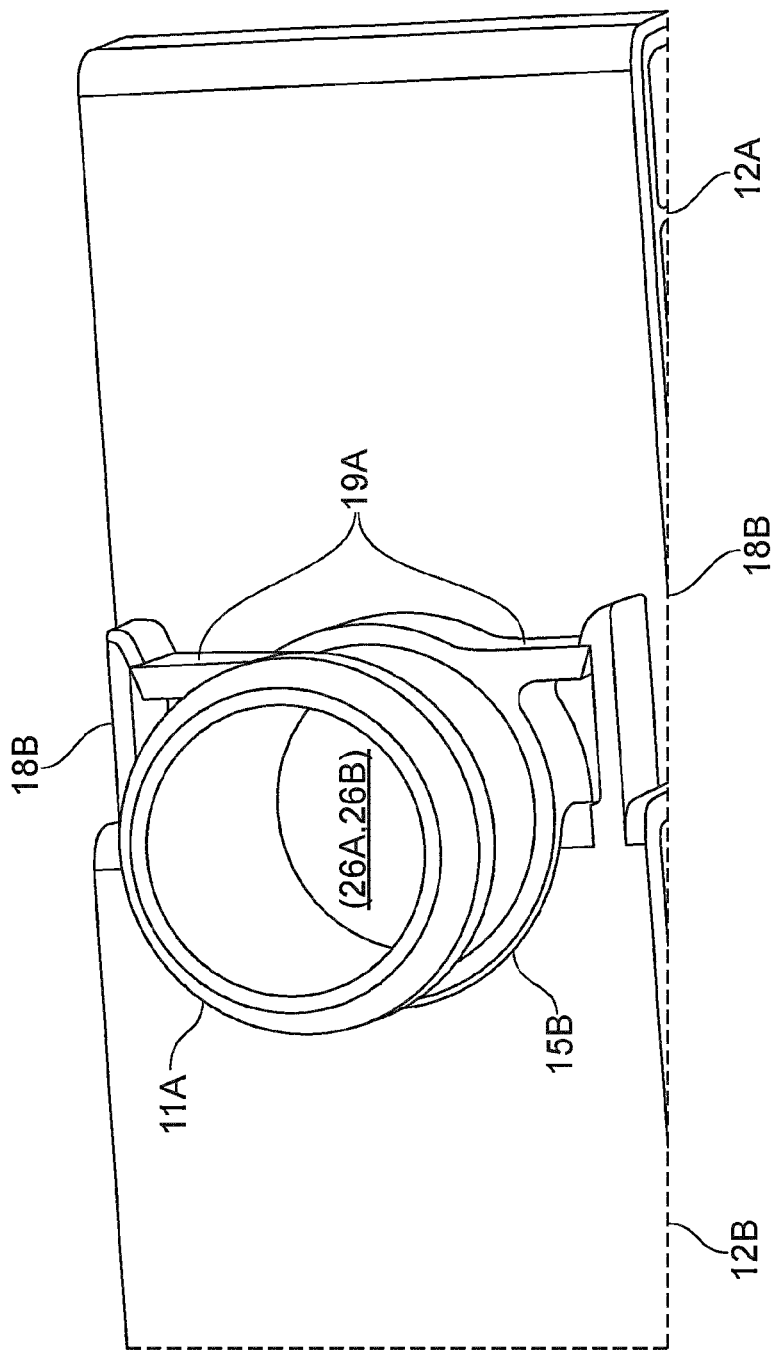

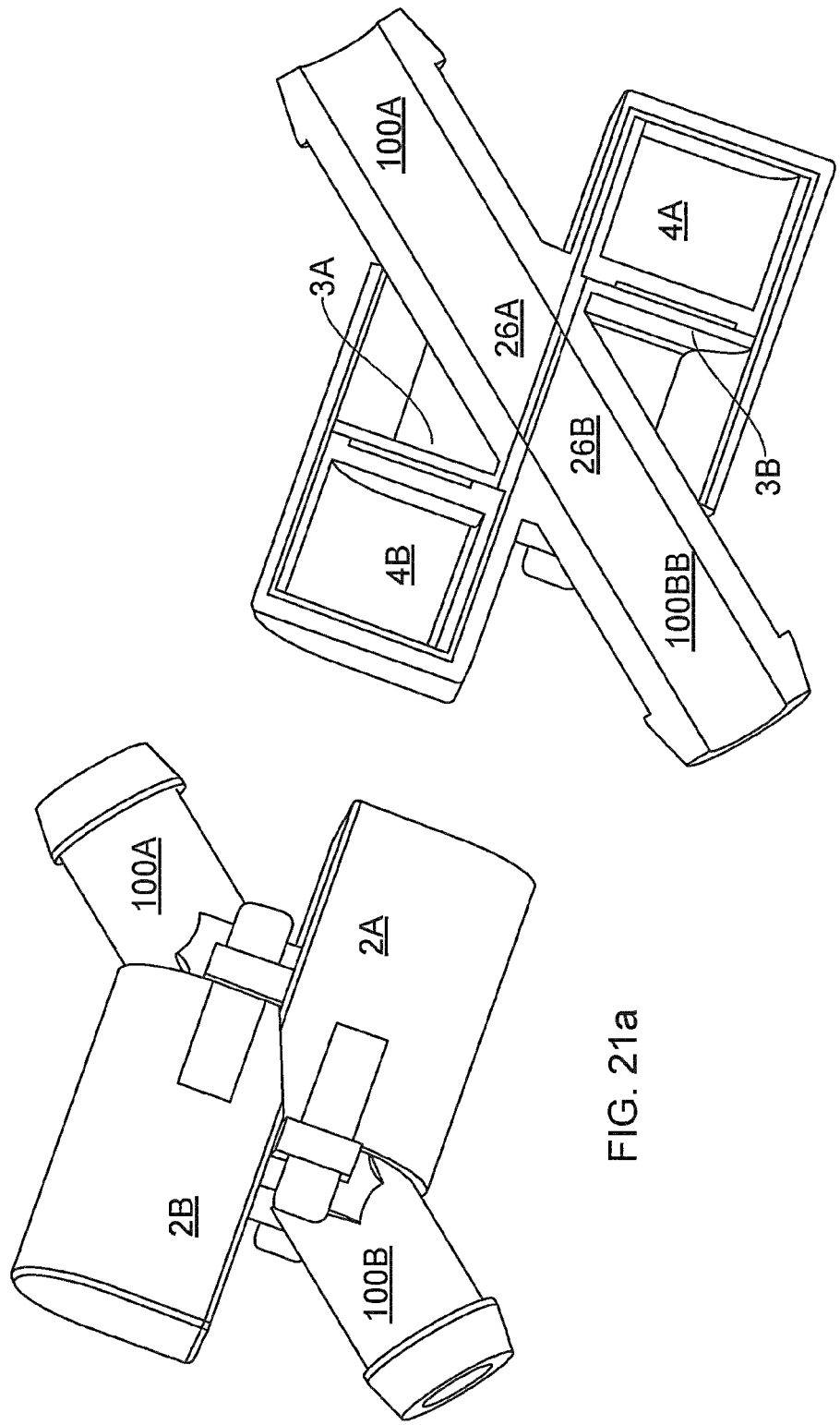

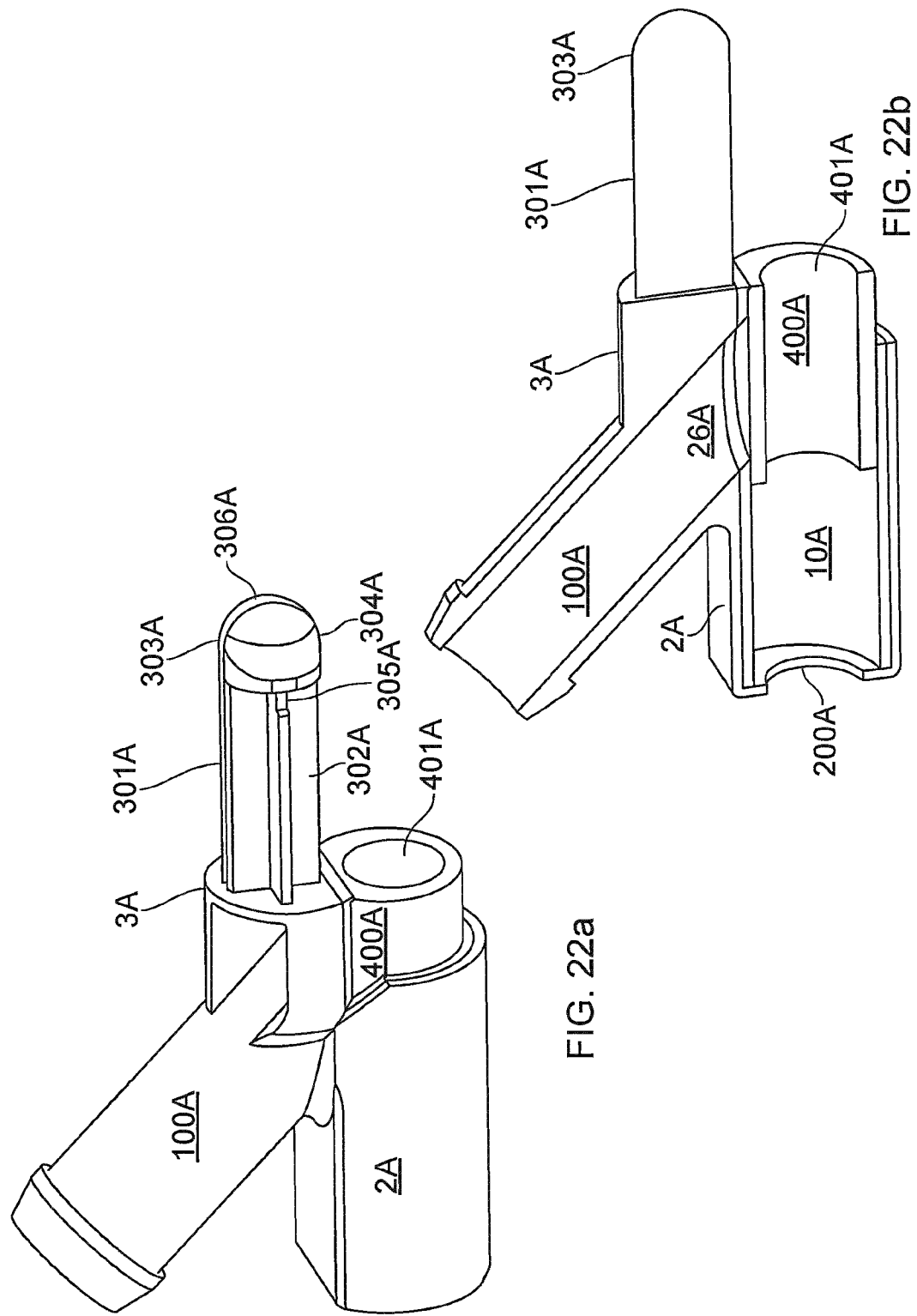

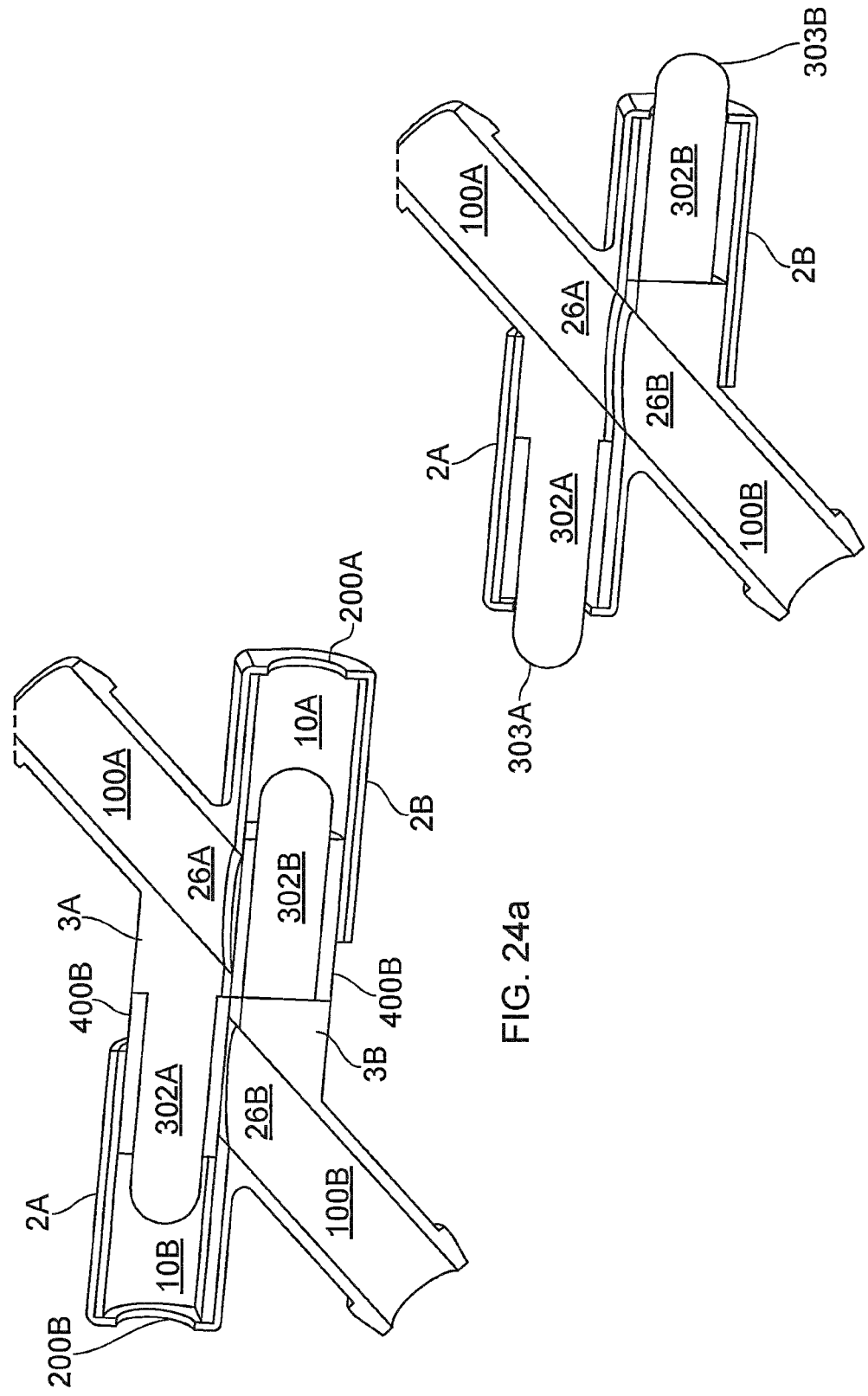

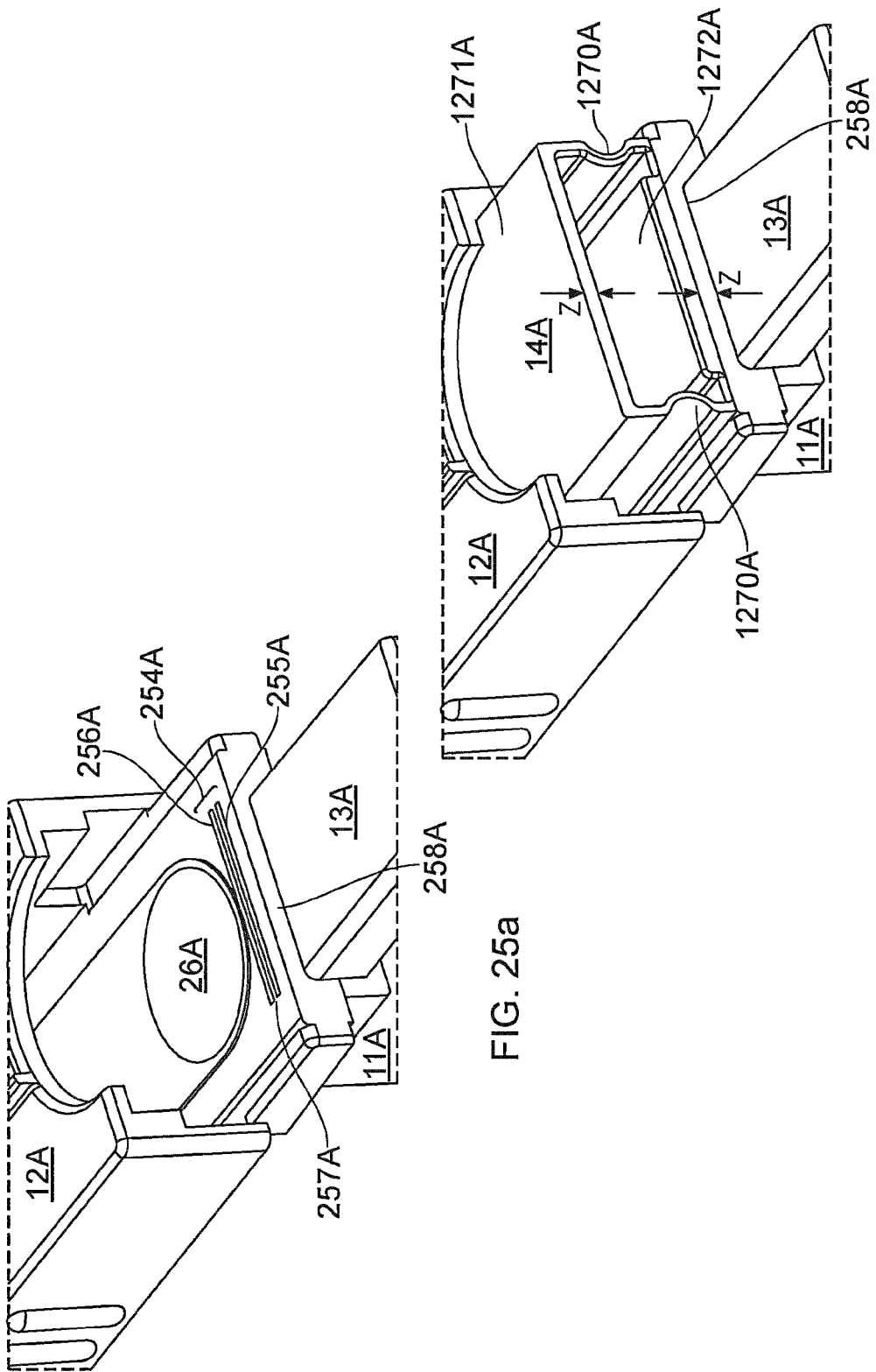

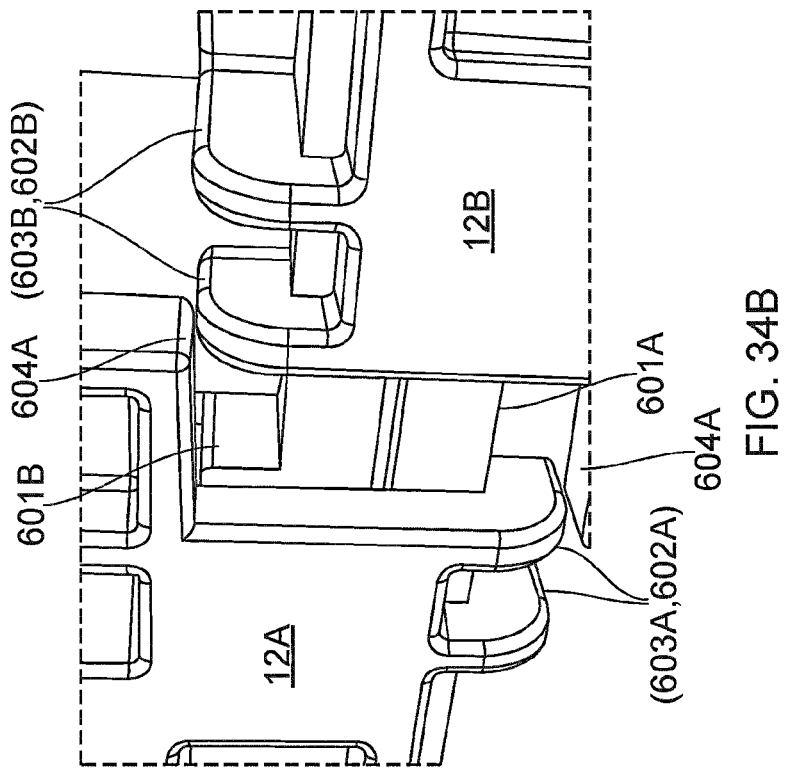
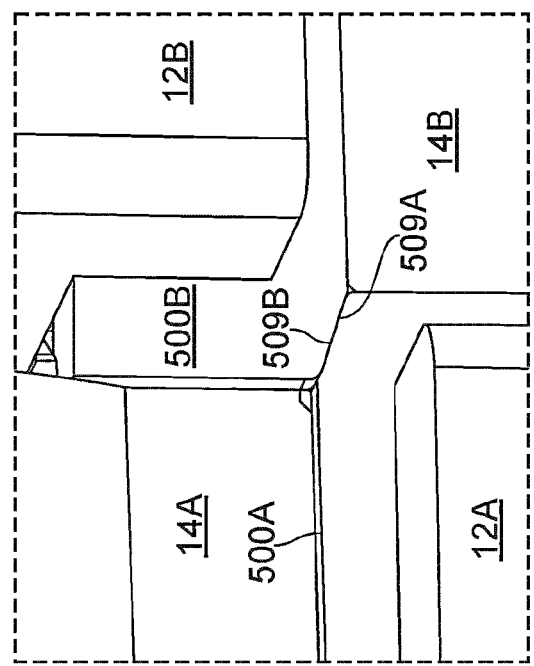
FIG. 34B
FIG. 34A

CONNECTOR

This application is a national stage filing under 35 U.S.C. § 371 of international PCT application PCT/EP2021/085552, filed Dec. 13, 2021, which claims priority from earlier application number GB2020053.1 filed Dec. 17, 2020 and from earlier application number GB2113596.7 filed Sep. 23, 2021, the contents and elements of which are herein incorporated by reference for all purposes.

FIELD OF THE INVENTION

The present invention relates to connectors for forming fluid flow passageways. The invention relates, for example, to connectors for safely forming a fluid-tight connection between fluid flow conduits to form a fluid flow pathway therebetween. Particularly, although not exclusively, the invention relates to connectors for forming fluid flow passageways in medical, pharmaceutical, and bioprocessing applications.

BACKGROUND

In certain circumstances, it is critical that the process of forming a fluid flow conduit connection avoids, or at least minimises the possibilities for introducing contaminants into the conduit so formed. This is, of course, critical in medical settings but is also of great importance in other setting such as in food manufacturing or processing settings where contamination control is necessary.

In certain medical, pharmaceutical, and bioprocessing applications it may be required to join two fluid flow conduits such that they form a fluid flow pathway between them that is sterile and does not leak. In these applications it is vital to ensure that any fluid passing through this connection point is not exposed to foreign contaminates such as microbes or debris from the external environment. Likewise, it is important that the external environment including human operators are not exposed to the fluid flowing between the two connected fluid flow conduits.

This type of sterile connection is especially important in processes where the fluid is either; highly sensitive to external contaminants, is cytotoxic or hazardous to health and/or is for use in patients (animal or human) where any external contamination would pose a threat to life or compromise the effectiveness of treatment with said fluid. A number of such sterile or "aseptic" connectors currently exist in the marketplace. Many employ the use of a sacrificial membrane that serves to protect the openings of the fluid conduits until such time as the two conduits are brought together in a closed, or semi-closed environment, at which point they may be safely removed.

Often, the bringing together of the two reciprocal connectors to form the sterile connection requires a multi-step sequence of events. These sequences range in terms of complexity and time taken to affect an aseptic connection, with many of the connectors requiring either significant force, significant user training and/or additional clamping to create a successful connection which can withstand the required operating conditions. Unfortunately, the currently available connector offerings still carry significant user error issues inherent to their design and mode of operation.

The invention aims to address this problem and to provide a connector apparatus for use in creating connections between fluid flow conduits to safely form fluid flow pathways.

SUMMARY OF THE INVENTION

In a first of its aspects, the invention may provide a connector adapted for forming a fluid flow pathway therethrough by connection with a reciprocal connector, wherein both the connector and the reciprocal connector each comprise: a fluid flow passageway part defining a fluid flow opening; a socket part located upon the fluid flow passageway part adjacent to the fluid flow opening; a plug part located upon the fluid flow passageway part adjacent to the fluid flow opening and spaced from the socket part in a direction crossing the fluid flow opening, wherein the socket part of the connector is configured to receive therein the plug part of said reciprocal connector to connect thereto such that the fluid flow opening of the connector is aligned in register with the fluid flow opening of the reciprocal connector; and, a closure part arranged to openably close the fluid flow opening of the connector and to receive an urging force from said received plug part of the reciprocal connector thereby to be displaced in a direction crossing the fluid flow opening to uncover the fluid flow opening such that the connector is thereby connectable to the reciprocal connector with respective fluid flow openings in fluid communication.

Preferably, the configuration of the connector means that it is able to serve as a reciprocal connector to a substantially identical connector (e.g., a replica of itself, or at least having a substantially identical connection interface in function and/or design, shape or structure), and the two can be directly connected to each other, with each one of the two connectors acting upon the other in the same way and each one responding to the other in the same way. As a result, preferably the connector is "genderless" such that a user need only obtain a plurality of copies of the same connector in order to be able to make such connections. It is not necessary in this case to obtain a number of "male" connectors and an equal number of corresponding "female" connectors, as in prior art systems. The user may be safe in the knowledge that each connector according to the invention is connectable to another such connector. Historically, connectors in the art involve two structurally distinct parts: a male part and a female part configured to mate together to form the desired connection. These two "gendered" parts are two distinctly different parts each with its own structure designed to mate with an inverse structure on the other part. Connections like these are considered in the art to be "gendered". The "female" attributes of a connector are generally those defining a receptacle that receives and holds the "male" connector element. The terms "socket" and "plug" are of used in the art synonymously with "female" and "male" in this context. Gendered connectors have the opposite nominal gender to the connector they are designed to connect (or "mate") with.

However, "genderless" connections are considered in the art to be those in which the interconnecting elements of the two connector parts are substantially identical in function and/or design, shape or structure, thus eliminating the need for different male and female parts to make the connection. The term "genderless" is used in the art to include connectors having mating elements or surfaces possessing both male and female attributes involving complementary paired identical parts each individually containing both "male" attributes (e.g., protrusions) and "female" attributes (e.g., indentations). These mating structures may be mounted into identical fittings which can freely mate with any other, without regard for gender.

Genderless connectors may eliminate the problem inherent in gendered connectors whereby two connectors of the same gender cannot be mated. This attribute is especially important when designing new fluid pathways in industrial settings with multiple connections, as it reduces errors in designing the system where the designer must ensure each connection has the correct gender ("male" or "female") to interact with the next part of the system, at each connection point. The use of genderless connectors also makes ordering replacement parts much simpler, as the purchaser does not need to be concerned about the number of both "male" and "female" parts held in stock on site, where a relative imbalance or shortage in stock of either version of the connector could lead to process downtime and in ordering the correct number of male to female parts. In connectors currently available, typically each manufacturer has a distinct connection type, so connectors from one manufacturer cannot be used interchangeably with those from another manufacturer. Genderless connectors may be simpler and/or more intuitive to use because they make possible a reduced number of actuation steps—being genderless means that the actuation of one part (one half of the connection) is the same as the actuation of the other part (other half of the connection). The more distinct/different actuation steps required in a connection, the higher is the risk of operator error.

A further advantage of genderless connectors is the reduced tooling requirement for manufacturing (e.g., moulding) the constituent parts of the connector. Because a genderless connector, according to preferred aspects of the invention, connects with a replica of itself, only one set of tools are required for the production of a connector system. This reduces cost and time of manufacture.

In preferred aspects of the invention disclosed herein, the connection is genderless. The plug part of the connector (or, therefore, of the reciprocal connector) may be configured to be pushed into the socket part of the reciprocal connector (or, therefore, of the connector) during connection of the connector and reciprocal connector. This pushing may be a linear displacement in a direction transverse (e.g., perpendicular) to a longitudinal axis of the fluid flow channel. The displacement may be a linear sliding action (e.g., without rotation or twisting). The connection preferably forms a push-fit, or a click-fit or snap-fit (e.g., as described in examples below), of the received plug part of the reciprocal connector (or, therefore, of the connector) within the receiving socket part of the connector (or, therefore, of the reciprocal connector) as the plug part is pushed into the socket part. The fluid flow opening of the connector (or, therefore, of the reciprocal connector) may thereby be pushed into register/alignment with an opposing fluid flow opening of a reciprocal connector (or, therefore, of the connector) during the act of connecting (e.g., pushing together) the connector to the reciprocal connector.

The fluid flow passageway of the connector (or, therefore, the reciprocal connector) is preferably linear in extent and extends along a longitudinal axis linearly (i.e., is straight) from a fluid flow inlet (e.g., nozzle) to the fluid flow opening. The plug part of the connector may be configured to be pushed towards (and into) the socket part of the reciprocal connector (and vice versa) in a direction is transverse (e.g., perpendicular) to the longitudinal axis of fluid flow passageway. The connector and reciprocal connector may be connected with the longitudinal axes of respective fluid flow passageways aligned in coaxial alignment. This has the benefit of providing a composite fluid flow passageway (i.e., formed by the two colinear flow passageways) that is linear, without bends of turns, along its longitudinal axis. Flow of fluid along the composite fluid flow passageway will therefore not suffer pressure drops as would otherwise be caused by a non-linear fluid flow passageway.

Preferably, the plug part and the socket part are located upon the fluid flow passageway part adjacent to (e.g., directly disposed next to) opposite respective sides of the fluid flow opening, being separated in a direction transverse to (e.g., substantially perpendicular to) a longitudinal axis of the fluid flow passageway part. The plug part and the socket part may be located upon the outer surface of the fluid flow passageway part adjacent to opposite respective sides of the fluid flow opening, being separated in a direction transverse to (e.g., substantially perpendicular to) a longitudinal axis of the fluid flow passageway part, as well as being separated in a direction axially along the longitudinal axis of the fluid flow passageway part. Longitudinal axes of the plug part and the socket part may be generally parallel to each other, and may also be transverse to (e.g., coplanar with) the longitudinal axis of the fluid flow passageway. When the connector is rotated through 180 degrees around an axis perpendicular to the longitudinal axis of the fluid flow passageway and perpendicular to longitudinal axis of the socket part and/or plug part, the result may be to provide the orientation necessary for functioning as a reciprocal connector to connect to a connector as described above. To this extent, a reciprocal connector, when connected to a connector, may be substantially identical to the connector when rotated through the aforesaid 180 degrees (i.e., as an example of "genderless"). Consequently, the fluid flow opening, the socket part and the plug part of both the connector and the reciprocal connector may be configured such that the connector is connectable to the reciprocal connector to position the longitudinal axis of respective fluid flow passageways thereof in mutually coaxial alignment.

The invention may provide a connector apparatus for use in creating connections between fluid flow conduits to safely form sterile fluid flow pathways with a reduced number of manual operational steps and without employing the use of sacrificial membranes or additional clamps. For example, an effective and simple to install aseptic connector may be provided which may be capable of meeting one or more of the following beneficial requirements: providing a reliable and robust sterile connection; able to operate at suitable processing temperatures and pressures; cost effective to manufacture and install; reducing the likelihood of operator error and requiring less operator training; requiring lower/minimal operator force and is quick and safe to install; made from compatible and safe materials.

The fluid flow passageway part is preferably configured, in use, to be in contact with a fluid passing through the fluid flow conduit formed by the connection of the connector to a reciprocal connector. Material(s) from which the fluid flow passageway part is formed are preferably materials having an appropriate chemical resistance (i.e. resistance to chemical attack, damage or degradation when in contact with selected fluid chemical). The fluid flow passageway part (and preferably the plug part and/or preferably the socket part) is preferably formed from a material having a suitably greater degree of rigidity in comparison with that of the closure part. Preferably, the closure part is configured to flex resiliently, whereas the fluid flow passageway part (and preferably the plug part and/or preferably the socket part) is preferably configured to be substantially rigid and substantially inflexible. The appropriate rigidity of the fluid flow passageway part (and preferably the plug part and/or preferably the socket part) may be achieved through a combination of wall thickness, design features and material selection. The fluid flow passageway part (and preferably the plug part and/or preferably the socket part) may be integrally formed, and may be formed as a single moulding. These part(s) may be moulded from a polycarbonate, polysulfone, acetal, polypropylene or Nylon 6 for example.

The closure part may be formed as a single moulding and may be formed as a single injection moulding. The connector may be used in such a way that the closure part will not come into contact with the fluid subsequently flowing through the conduit formed by connecting two connectors after that conduit has been formed. In this case it is not necessary for this part to have any chemical resistance. The material selected in this case may preferably have mechanical properties that allow the closure part to flex correctly when it slides away from the fluid flow opening in response to the urging from an advancing plug part of a reciprocal connector during the connection process. In this case the material of the closure part may be a polypropylene, polyethylene or an ABS (Acrylonitrile butadiene styrene).

Conversely, the connector, when not connected (yet) to a reciprocal connector, may be used as a closure device to close the end of fluid flow conduit connected to the fluid flow passageway of the connector, thereby to hold back the fluid until it is connected to a reciprocal connector. In this case, the closure part may also be made of a material having a suitable degree of chemical resistance. Thus, the material selected for the closure part, in this case, may also have mechanical properties that allow the part to flex as necessary. In this case the material from which the closure part is formed may comprise a polycarbonate, polyethylene, polypropylene, an acetal (copolymer or homopolymer), PTFE or Nylon 6. Other chemically resistant mouldable plastics materials are available and may be selected according to specific applications.

By providing a closure part covering the fluid flow opening when the connector is unconnected to a reciprocal connector, but which is moveable to reveal the fluid flow passageway by the same action which connects the connector to its reciprocal connector, the invention provides for the simultaneous and immediate occurrences of: (a) the uncovering of the fluid flow openings of the connector and its reciprocal; (b) the alignment of the fluid flow openings of the connector and its reciprocal; and (c) the connection of the connector and its reciprocal. This reduces the time taken to connect the two connectors, and the number of manual operations/actions required to connect the two connectors and, therefore, it reduces the exposure of the fluid flow openings of the two connectors and the consequent opportunities for contamination. It is to be understood that the fluid flow opening may be a terminal fluid flow opening of the greater fluid flow conduit to which the connector forms a terminal end part. The connector may comprise an adaptor disposed (e.g. formed) at an end of the fluid flow part which is opposite to the end at which the fluid flow opening is disposed (e.g. formed). The adaptor may be configured for making a fluid-tight connection to a hose, and may comprise a hose adaptor, or an insertion nozzle for insertion into a hose. The adaptor may comprise a spike or cannula or other elongated fluid flow interface for permitting the adaptor to form a safe fluid flow connection to a fluid flow vessel (e.g. bag, vial or the like) or conduit (e.g. pipe, hose or the like).

Desirably, the closure part is configured to be displaced into the socket part by said displacement. For example, the closure part may be housed within the socket part and may be slidably displaceable in a direction in to (i.e. further in to) the socket part. The closure part maybe fully housed within the socket part having a portion of the closure part accessible via an opening of the socket part, or may be partially housed within the socket part having a portion of the closure part protruding from the socket opening of the socket part. The accessible portion of the closure part may thereby be accessible to a plug part of a reciprocal connector to permit the plug part to bear against the accessible portion of the closure part there by two urge displacement of the closure part into the socket part.

Preferably, the plug part of the reciprocal connector is configured to be inserted into the socket part to retain the displaced closure part therein. The socket part may comprise an elongated bore or passageway possessing a longitudinal axis along which the displaced closure part, and an inserted plug part of the reciprocal connector, are able to concurrently move. The transverse dimensions (e.g. width, height or diameter) of a bore of the socket part may shaped as to be reciprocally sympathetic to the transverse outer dimensions (e.g. outer width, height or diameter) of the closure part and/or of the plug part of the reciprocal connector. The transverse dimensions of the plug part and the socket part may be such that an interference fit is formable between the socket part and the plug part of a reciprocal connector when inserted into the plug part during connection of the connector with a reciprocal connector.

The closure part may comprise an elongated bore or passageway possessing a longitudinal axis along which an inserted plug part of the reciprocal connector are able to move sufficiently to substantially fill the bore of the closure part. The longitudinal axis of the bore of the closure part may be substantially parallel to (e.g. collinear with) the longitudinal axis of the bore of the socket part. The transverse dimensions (e.g. width, height or diameter) of a bore of the closure part may shaped as to be reciprocally sympathetic to the transverse outer dimensions (e.g. outer width, height or diameter) of the plug part of the reciprocal connector. The transverse dimensions of the plug part and the closure part may be such that an interference fit is formable between the closure part and the plug part of a reciprocal connector when inserted into the closure part during connection of the connector with a reciprocal connector.

The connector may comprise a releasable catch mechanism operable to change from a first state configured to retain the closure part in a position closing the fluid flow opening to a second state configured to permit said displacement of the closure part. The releasable catch mechanism may be formed by a mechanical interface between the socket part and the closure part. The releasable catch mechanism may comprise a resiliently deformable arm, peg or clip member provided on either one of the socket part and the closure part, configured to releasably engage with a reciprocating slot, detent, notch, ridge, edge or groove formation provided on the other one of the socket part and the closure part. The releasable catch mechanism may be configured to form a snap-fit connection between the resiliently deformable arm, peg or clip member and the reciprocating slot, detent, notch, ridge, edge or groove formation.

The releasable catch mechanism is preferably configured for actuation by the plug part of said reciprocal connector from within the socket part of the connector to change from said first state to said second state by action of receiving the plug part of said reciprocal connector within the socket part of the connector. For example, the resiliently deformable arm, peg or clip member may be disposed up on the connector in a position accessible by the plug part of the reciprocal connector for receiving an urging force from a surface of the plug part for resiliently deforming the resiliently deformable arm, peg or clip member as the plug part is pushed into the socket part of the connector during connection of the connector and reciprocal connector. The plug part, the socket part and the resiliently deformable arm, peg or clip member may be collectively configured such that the urging force in question is sufficient to disengage the resiliently deformable arm, peg or clip member from the reciprocating slot, detent, notch, ridge, edge or groove formation so as to release the releasable catch mechanism.

The releasable catch mechanism may comprise an abutment surface configured for abutment by the plug part of the reciprocal connector when received within the socket part of the connector, and the releasable catch mechanism is operable to change from the first state to the second state in response to the abutment between the releasable catch mechanism and the plug part of the reciprocal connector.

The socket part of the connector may comprise the abutment surface of the releasable catch mechanism. For example, the abutment surface may be presented inwardly to the bore of the socket part, so as to be accessible by the plug part of a reciprocal connector when inserted into the bore of the socket part. The abutment surface may be disposed upon the resiliently deformable arm, peg or clip member. The resiliently deformable arm, peg or clip member may be disposed upon (e.g. formed in) the socket part. For example, the resiliently deformable arm, peg or clip member may be disposed upon (e.g. formed in) a surface or wall of the bore of the socket part. The reciprocating slot, detent, notch, ridge, edge or groove formation may be disposed upon (e.g. formed in) a surface or wall of the bore of the closure part.

The closure part of the connector may comprise the abutment surface of the releasable catch mechanism. For example, the abutment surface may be presented inwardly to the bore of the closure part, so as to be accessible by the plug part of a reciprocal connector when inserted into the bore of the closure part. The abutment surface may be disposed upon the resiliently deformable arm, peg or clip member. The resiliently deformable arm, peg or clip member may be disposed upon (e.g. formed in) the closure part. For example, the resiliently deformable arm, peg or clip member may be disposed upon (e.g. formed in) a surface or wall of the bore of the closure part. The reciprocating slot, detent, notch, ridge, edge or groove formation may be disposed upon (e.g. formed in) a surface or wall of the bore of the socket part.

The closure part may comprise a bearing surface configured for receiving the urging force from the plug part of the reciprocal connector when received within the socket part of the connector. The bearing surface may be configured such that it receives the urging force from the plug part of the reciprocal connector not before the releasable catch mechanism has changed from said first state to said second state. For example, the bearing surface may be configured such that it receives the urging force from the plug part of the reciprocal connector after (or concurrently as) the releasable catch mechanism has changed from the first state to the second state. For example, the urging force which induces the releasable catch mechanism to change from the first state to the second state may be separate from the urging force which subsequently separately urges displacement of the closure part into the socket part. For example, the abutment surface of the resiliently deformable arm, peg or clip member may be separate from the bearing surface for receiving from the inserted plug part an urging force for displacing the closure part along the bore of the socket part of the connector after the releasable catch mechanism is in the second state. Alternatively the bearing surface may be configured such that it receives the urging force from the plug part of the reciprocal connector before the releasable catch mechanism has changed from the first state to the second state. For example, the urging force which induces the releasable catch mechanism to change from the first state to the second state may be the same urging force which also urges displacement of the closure part into the socket part. For example, the abutment surface of the resiliently deformable arm, peg or clip member may also serve as an abutment surface for receiving from the inserted plug part an urging force for displacing the closure part along the bore of the socket part of the connector after the releasable catch mechanism is in the second state.

Desirably, the socket part defines a bore for receiving the plug part of the reciprocal connector, whereby the lateral dimension (e.g. width, or height, or area, or diameter etc.) of an opening of the bore exceeds an internal lateral dimension (e.g. width, or height, or area, or diameter etc.) of the bore which abuts against the plug part of the reciprocal connector when received therein to urge the fluid flow passageway part of the connector towards the fluid flow passageway part of the reciprocal connector. In this way, the action of laterally squeezing together the connector and the reciprocal connector to advance the plug part of each in to the socket part of the other, concurrently produces a longitudinal squeezing action which squeezes the fluid flow openings (i.e. the opposing, aligned peripheral edges) of the connectors together. A sufficient squeezing force may be a force sufficient to sealingly hold back fluid of a pressure (P) within the fluid flow conduit produced by the aligned fluid flow passageways of the two connectors when fully connected. This pressure is exerted upon the interface between the two squeezed-together fluid flow openings. Preferably: $0.5\ \text{bar} \le P \le 4\ \text{bar}$, or more preferably $0.5\ \text{bar} \le P \le 6\ \text{bar}$, or more preferably $4\ \text{bar} \le P \le 6\ \text{bar}$, or yet more preferably, $4\ \text{bar} \le P \le 10\ \text{bar}$, or preferably $6\ \text{bar} \le P \le 10\ \text{bar}$.

Preferably, the plug part and the socket part are located upon the fluid flow passageway part adjacent to opposite respective sides of the fluid flow opening, being separated in a direction transverse to the axis of the fluid flow passageway part. In this way, a transverse movement or action is enabled for connecting the two connectors together which is sympathetic to a transverse displacement of the closure part of each connector.

Desirably, the plug part and the socket part are located upon the fluid flow passageway part adjacent to opposite respective sides of the fluid flow opening, being separated in a direction axially along the axis of the fluid flow passageway part. In this way, a longitudinal accommodation is provided to admit a transverse movement or action for connecting the two connectors together. This also accommodates a longitudinal squeezing action to urge together the fluid flow openings of each connector.

Preferably, the fluid flow opening, the socket part and the plug part of both the connector and the reciprocal connector are configured such that the connector is connectable to the reciprocal connector to position the longitudinal axis of respective fluid flow passageways thereof in mutually coaxial alignment.

The plug part of the connector is preferably configured for insertion into the socket part of the reciprocal connector to connect thereto such that the fluid flow passageway part of the connector is urged against the fluid flow passageway part of the reciprocal connector to urge respective fluid flow openings together.

The connector may be such that the longitudinal position of the plug part of the connector and the longitudinal position of the socket part of the connector are such that:

(1) The outer surface of the plug part which is also furthest from the fluid flow opening, is also longitudinally separated from the fluid flow opening by a predetermined longitudinal separation; and (2) The inner bore surface of the socket part which is furthest from the fluid flow opening, is also longitudinally separated from the fluid flow opening by the same predetermined longitudinal separation.

This accommodates a longitudinal squeezing action to urge/squeeze together the fluid flow opening of each connector. This may provide an interference fit between the plug part and the socket part and between the peripheral edges of the opposing fluid flow openings, of a connector and a reciprocal connector when connected.

Preferably, the closure part comprises a concealment surface portion which is disposed to overlay the fluid flow opening. Preferably the closure part fully seals and conceals the fluid flow opening around the whole of its periphery.

The closure part may be resiliently deformable and compressed within the socket part to resiliently urge the concealment surface against the fluid flow passageway parts surrounding the peripheral edge of the fluid flow opening.

Preferably, the concealment surface portion comprises a surface relief ramp formation configured to project therefrom through the fluid flow opening and into the fluid flow passageway whereby said displacement in a direction crossing the fluid flow opening causes the surface relief ramp formation to ride over an abutting peripheral edge of the fluid flow opening thereby to displace the concealment surface portion in a direction away from the fluid flow opening. This formation may not only enhance the efficacy with which the closure part may provide a sealing interface with the periphery of the fluid flow opening, but may also permit the surface portions of the closure part which surround the fluid flow opening, which are not in communication with it, to be lifted (displaced) away from the periphery of the fluid flow opening as the closure part is displaced and moved (e.g. slid) over the fluid flow opening to reveal the opening. This reduces the likelihood of ingress into the fluid flow opening of contaminants that may be present upon the surface portions of the closure part which surround the fluid flow opening.

The surface relief ramp formation may extend along the concealment surface to define a shape reciprocating the shape of a peripheral edge of the fluid flow opening. For example, a circular fluid flow opening may be accompanied by a circular surface relief ramp formation upon the concealment surface.

The surface parts of the connector immediately surrounding peripheral edge of the fluid flow opening facing the closure part, may be present one or more surface relief ramp ring formations (e.g. concentric rings, of more than one), or partial ring formations (e.g. arc, or arcs), surrounding some or all of the periphery of the fluid flow opening. The closure part may be urged to abut against the one or more surface relief ramp ring formations. This assists in forming a more secure sealing interface between the closure part and the opposing portions of the fluid flow part containing the fluid flow opening.

The closure part is preferably resiliently deformable to compress resiliently in the direction away from the fluid flow opening in response to the surface relief ramp formation riding over an abutting peripheral edge of the fluid flow opening. Compression of the closure part may be facilitated by provision of a resiliently deformable cantilever spring arm formation in each of the lateral side walls of the closure part. For example, two parallel cantilever spring arms may connect opposing upper and lower platform parts of the cover part. The upper and lower platform parts may be generally planar and mutually parallel. The upper and lower platform parts may be spaced apart from each other in a direction parallel to the longitudinal axis of the fluid flow part. These upper and lower platform parts may form the upper and lower parts of the closure part. The outer surface of the upper platform may also provide a closure surface for directly (but displacably) covering the fluid flow opening of the connector. One end of a respective resiliently deformable cantilever spring arm formation may be joined to the upper platform of the closure part at a location proximal to the opening of the bore of the closure part. The other end of the respective resiliently deformable cantilever spring arm formation may be joined to the lower platform of the closure part at a location axially further inside the bore of the closure part, on the same side. This allows the resiliently deformable cantilever spring arm formation to extend in a direction diagonally transverse to the compressive forces to be experienced by the closure part as it is displaced into the bore of the socket part of the connector. Consequently, this diagonal direction is sympathetic to the operation of the resilient 'springy' action of the cantilever spring arm formation.

The connector, when not connected (yet) to a reciprocal connector, may be used as a closure device to close the end of fluid flow conduit connected to the fluid flow passageway of the connector, thereby to hold back the fluid until it is connected to a reciprocal connector. The material selected for the closure part, in this case, may also have mechanical properties that allow the part to flex as necessary yet also to exert a sufficient urging force (i.e. a spring-like force) against the periphery of the fluid flow opening of the connector when static and closing-off the fluid flow passage way, prior to connection with a reciprocal connector. A sufficient urging force may be a force (F) sufficient to sealingly hold back fluid of a pressure (P) within the fluid flow passageway which is exerted upon the closure part at the fluid flow opening of a given cross sectional (i.e. bore) area (A), whereby: $F = P \times A$ Newtons. Preferably: $0.5 \text{ bar} \leq P \leq 4$ bar, or more preferably $0.5 \text{ bar} \leq P \leq 6$ bar, or more preferably $4 \text{ bar} \leq P \leq 6$ bar, or yet more preferably, $4 \text{ bar} \leq P \leq 10$ bar, or preferably $6 \text{ bar} \leq P \leq 10$ bar. In this case the material from which the closure part is formed may comprise a polycarbonate, polyethylene, an acetal (copolymer or homopolymer), PTFE or Nylon 6. Other chemically resistant mouldable and sufficiently springy plastics materials are available and may be selected according to specific applications. Compression of the closure part may be facilitated by provision of a resiliently deformable curvature in a wall of the closure part, such as in an optional inner strut wall of the closure part, and/or in each of the lateral side walls of the closure part, which may run longitudinally parallel to or along the longitudinal axis of the bore of the closure part. If a curved inner strut wall is provided, the plug part may comprise a slot or other shaping or configuration suitable to accommodate the corresponding curved inner strut wall of the reciprocal connector if it is configured to be inserted into a bore of the closure part of the reciprocal connector containing the corresponding curved inner strut wall when the plug part is connected to the socket part of the reciprocal connector. For example, a curved inner strut wall, and/or two opposing curved side walls, may connect opposing upper and lower platform parts of the cover part. The upper and lower platform parts may be generally planar and mutually parallel. The upper and lower platform parts may be spaced apart from each other in a direction parallel to the longitudinal axis of the fluid flow part. These upper and lower platform parts may form the upper and lower parts of the closure part. The outer surface of the upper platform may also provide a closure surface for directly (but displacably) covering the fluid flow opening of the connector. The top of a respective resiliently deformable curved inner strut wall, and/or curved side wall formation may be joined to the upper platform of the closure part, and the other end of the respective resiliently deformable curved inner strut wall, and/or curved side wall formation may be joined to the lower platform of the closure part on the same side. This allows the resiliently deformable curved inner strut wall, and/or curved wall formation to curve in a direction transverse to the compressive forces to be experienced by the closure part as it is displaced into the bore of the socket part of the connector. The curvature may comprise a radius of curvature in a plane transverse (e.g. substantially perpendicular) to the longitudinal axis of the closure part and/or of the bore of the socket part. The curvature may comprise a radius of curvature in a plane substantially parallel to the longitudinal axis of the fluid flow part. The curved inner strut wall, and/or curved side walls may be of substantially the same wall thickness as each other, and may be of substantially uniform thickness along the arc of their respective curvature. For example, each side wall may possess an inner wall surface facing into the bore of the closure part and having a first radius of curvature, and an outer wall surface facing away from the bore of the closure part and having a second radius of curvature which exceeds the first radius of curvature by an amount that is substantially constant along the arc of the curvature of the respective side wall. The first and second radii of curvature may share a common centre of curvature such that the arc of the outer wall surface is substantially parallel to the arc of the inner wall surface. Consequently, this bowed curvature direction allows the walls to resiliently flex in response to the compressive forces in question, in a manner sympathetic to the pre-existing curvature of the wall in question, to put into effect the operation of the resilient 'springy' action of the curved wall formations. This structure has been found to be very effective in providing greater spring forces (F) necessary to successfully resist (hold back) higher fluid pressures (P) within the pressure ranges discussed above, and also enables ease of manufacture when mounding the closure part incorporating the curved wall formations.

The invention, in another aspect, may provide a connector assembly comprising a pair of connectors each being as described above and wherein any one connector of the pair of connectors is an aforesaid reciprocal connector for the other connector of the pair of connectors.

The invention, in a further aspect, may provide a connector assembly comprising a connector and a reciprocal connector each adapted for forming a fluid flow pathway therethrough by connection of the connector with the reciprocal connector, wherein both the connector and the reciprocal connector each comprise: a fluid flow passageway part defining a fluid flow opening; a socket part located upon the fluid flow passageway part adjacent to the fluid flow opening; a plug part located upon the fluid flow passageway part adjacent to the fluid flow opening and spaced from the socket part in a direction crossing the fluid flow opening, wherein the socket part of the connector (or, therefore correspondingly, of the reciprocal connector) is configured to receive therein the plug part of said reciprocal connector (or, therefore correspondingly, of the connector) to connect thereto such that the fluid flow opening of the connector is aligned in register with the fluid flow opening of the reciprocal connector; and, a closure part arranged to openably close the fluid flow opening of the connector (or, therefore correspondingly, of the reciprocal connector) and to receive an urging force from said received plug part of the reciprocal connector (or, therefore correspondingly, of the reciprocal connector) thereby to be displaced in a direction crossing the fluid flow opening to uncover the fluid flow opening such that the connector is thereby connectable to the reciprocal connector with respective fluid flow openings in fluid communication.

In yet a further aspect, the invention may provide a method for forming a fluid flow pathway comprising the steps of: providing a connector assembly as described above; connecting the connector to the reciprocal connector with respective fluid flow openings in fluid communication.

Preferably, the connector comprises a transverse buffer member disposed along a step formation of the connector formed by an offset between adjacent surfaces of the connector where the base of the plug part resides. Preferably, the height of the step formation substantially matches the thickness of a platform part of the closure part. Preferably, the height of the transverse buffer member substantially matches both the height of the step formation and the thickness of a platform part of the closure part. Preferably, the transverse buffer member is a longitudinal extension of the step formation over which a lower platform part of the closure part of a reciprocal connector may slide during the process of connecting the connector part to the reciprocal connector part. Preferably, the transverse buffer member is formed from a compressible, compliant and/or resiliently deformable material. Preferably, the transverse buffer member is configured to compress in a direction which is directed perpendicular to the long axis of the buffer member and directed towards the fluid flow opening. Preferably, the transverse buffer member also comprises a covered surface part which is protectively covered by, and in physical contact with, the closure part of the connector when the connector is un-connected to a reciprocal connector wherein the covered surface part is revealed by compression of the transverse buffer member by a reciprocal connector. The transverse buffer member is configured such that said compression causes an upright front surface part thereof to tilt towards an opposing surface of the closure part of the reciprocal connector that applies the compressive force.

Preferably, the deformation of the transverse buffer member causes the covered surface part to peel away from a protective covering surface of the closure part with which it was in physical contact. Preferably, parts of the surface of the transverse buffer member are sealed-off and contained within a trapped volume defined by the opposing parts of the surface of the transverse buffer member and the abutting surface of the closure part of the reciprocal connector.

Preferably, the connector comprises two longitudinal buffer members each of which enable the formation of side seals concurrently at either longitudinal side of the parts of each connector surrounding its respective fluid flow opening. The longitudinal buffer members may be configured to be resiliently flexible/conformable against the abutting sides of an opposing closure part of a reciprocal connector forming a sealing (e.g., airtight) interface between the two connectors when the two connectors are connected together. The longitudinal buffer members of a connector and a reciprocal connector may form at least a part of an outer perimeter seal surrounding the respective fluid flow opening of the connector and the reciprocal connector when connected. The connector may comprise an inner transverse buffer member located within a surface region of the bore of the socked part that is contiguous with the surface region of the connector along which (or adjacent which) the outer transverse buffer member is located. The inner transverse buffer member is preferably located at one side of the fluid flow opening that is opposite to the side at which both the plug part and the outer transverse buffer member are located. The inner transverse buffer member is preferably configured to resiliently flex/conform against the abutting surface of the base of an opposing closure part of the connector both while the connector remains unconnected, and during and after the process of forming a connection with a reciprocal connector. The inner transverse buffer member of a connector may form at least a part of an outer perimeter seal surrounding the respective fluid flow opening of the connector and the reciprocal connector when connected. The inner transverse buffer member of a connector may be joined with, or integrally formed with, each of two longitudinal buffer members of the connector. The transverse buffer member, the inner transverse buffer member and two longitudinal buffer members of a connector and of a reciprocal connector may be configured to press against opposing surface parts to form at least a part of, or the whole of, an outer perimeter seal surrounding the respective fluid flow opening of the connector and the reciprocal connector when connected.

The invention includes the combination of the aspects and preferred features described except where such a combination is clearly impermissible or expressly avoided.

A reference herein to a "catch" may be considered to include a type of mechanical fastener that joins two (or more) objects or surfaces while allowing for their regular separation.

SUMMARY OF THE FIGURES

Embodiments and experiments illustrating the principles of the invention will now be discussed with reference to the accompanying figures in which:

FIGS. 1a and 1b show perspective views of a connector assembly;

FIG. 9 shows a perspective view of a connector assembly of FIG. 7;

FIGS. 17a, 17b and 17c show perspective views of a connector of FIG. 12a;

FIGS. 21a and 21b show cross-sectional and perspective views of a connector assembly formed from two connectors of FIGS. 20a and 20b;

FIGS. 22a and 22b show cross-sectional and perspective views of a connector;

FIGS. 24a and 24b show cross-sectional views of a connector assembly formed from two connectors of FIGS. 22a and 22b;

FIGS. 25a and 25b show perspective views of parts of a connector;

FIGS. 34A and 34B show close-up views of particular positions in a process of interconnection of a connector assembly formed from two connectors.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Referring to FIGS. 1a and 1b, there is shown a connector assembly according to an embodiment of the invention. FIG.

Figure 2B:
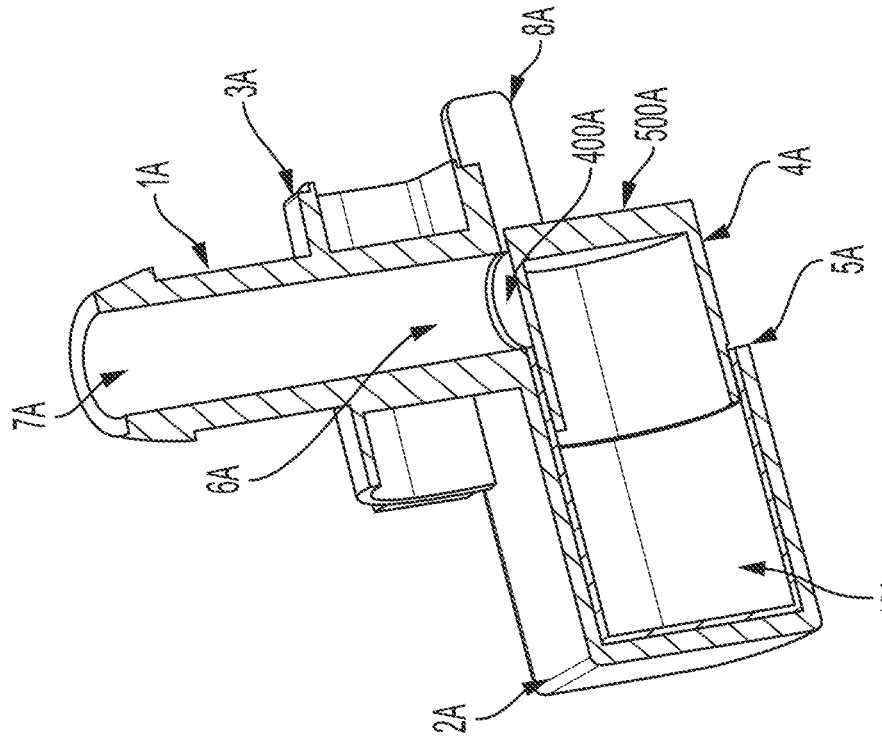
FIGS. 2a and 2b show a perspective view and a cross-sectional view of a connector forming a part of the assembly of FIGS. 1a and 1b.
Figure 2A:
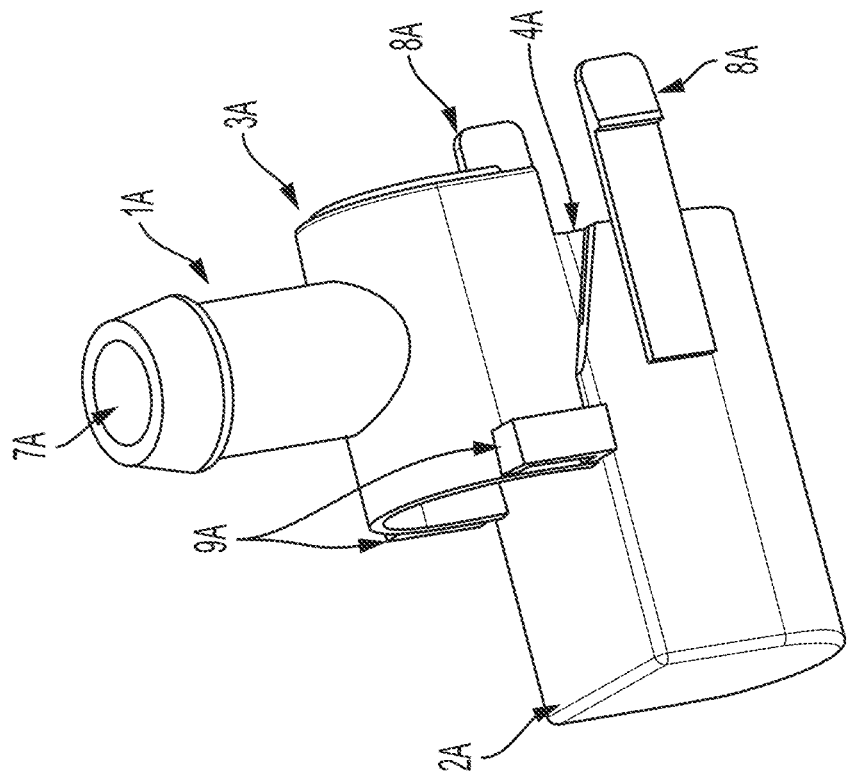

1a shows the assembly from one side, while FIG. 1b shows the same assembly from the opposite side. The connector assembly is adapted for forming a fluid flow pathway by connection of a connector with a reciprocal connector. Both the connector and the reciprocal connector are identical in structure. In other words, connector assembly comprises two identical connectors in that the reciprocal connector is simply a copy of the connector. Referring to FIGS. 2a and 2b, there is shown a perspective view of the connector in isolation (FIG. 2a) and a cross-sectional view of the connector in isolation (FIG. 2b). It is to be understood that the reciprocal connector, being a copy of the connector, is identical to the connector.

Each connector comprises a fluid flow passageway part (1A or 1B) defining a fluid flow opening (6A or 6B). A socket part (2A or 2B) located upon the fluid flow passageway part adjacent to the fluid flow opening. A plug part (3A or 3B) is located upon the fluid flow passageway part adjacent to the fluid flow opening (6A or 6B) and spaced from the socket part (2A or 2B) in a direction crossing the fluid flow opening.

The socket part (2A) of the connector is configured to receive within it the plug part (3B) of the reciprocal connector (and vice versa) thereby to connect the socket part of the connector to the plug part of the reciprocal connector. By doing so, the fluid flow opening (6A) of the connector is aligned in register with the fluid flow opening (6B) of the reciprocal connector. A bore (10A) of the socket part is dimensioned for receiving the plug part (3B) of the reciprocal connector, whereby a lateral dimension (e.g. width and/or height) of the opening of the bore exceeds a corresponding lateral dimension of an internal part of the bore which thereby abuts against the plug part (3B) of the reciprocal connector when it is received in the bore (10A). For example, the bore may be suitably tapered. The closure part may be suitably laterally compressible, resiliently, to accommodate the tapering constriction of the bore of the socket part when displaced along it. In the present example, closure part is formed as a hollow tube presenting a closed distal end accessible to the plug part (3B) of the reciprocal connector as an abutment surface (500A, or 500B for the reciprocal connector), and an open proximal end housed within the bore of the socket part permitting resilient compression of the closure part. Lateral compressibility may be provided in other configurations, as is exemplified in other embodiments disclosed herein. This forms an increasing interference fit between the received plug part (3B) of the reciprocal connector and the bore of the receiving socket part (10A) as the plug part is pushed into the socket part. Similarly, the closure part (4A) of the connector has a corresponding lateral dimension (e.g. width and/or height) which thereby abuts against the internal bore (10A) of the socket part (2A) of the connector when it is received in the bore (10A) so as to provide a firm interface with bore of the socket part which resists free slippage of the closure part relative to the socket part, thereby to hold the closure part in place over the fluid flow opening (6A), but to permit forced (urged) sliding displacement of the closure part along the bore of the socket part (i.e. into the socket part) in reaction to an urging force from an inserting plug part (3B) of the reciprocal connector. Preferably, the provision of a tapering bore of a socket part dimensioned for securely holding an un-displaced/displaced closure part and for firmly holding a received socket part, by interference fit, is applicable to each embodiment of the invention described herein.

Preferably, the lateral dimension of the bore (10A) of the socket part, in the direction transverse to the longitudinal axis of the fluid flow passageway (7A), is tapered so as to narrow/reduce at increasing distances into the bore (10A) of the socket part such that progressive insertion of the received plug part (3B) of the reciprocal connector (3B) along that bore causes the tapering inner surface of the bore to urge against the abutting surface of the received plug part (3B) thereby to urge the received plug part in a longitudinal direction towards the fluid flow opening of the fluid flow passageway part (1A) of the connector. Because the socket part of the connector and the plug part of the reciprocal connector are disposed symmetrically at opposite sides of the fluid flow opening (6A) of the connector (both in the lateral direction, and in the longitudinal direction), this means that this longitudinal urging force upon the plug part generated in this way also results in such longitudinal urging of the fluid flow opening (6B) of the reciprocal connector.

Figure 3:
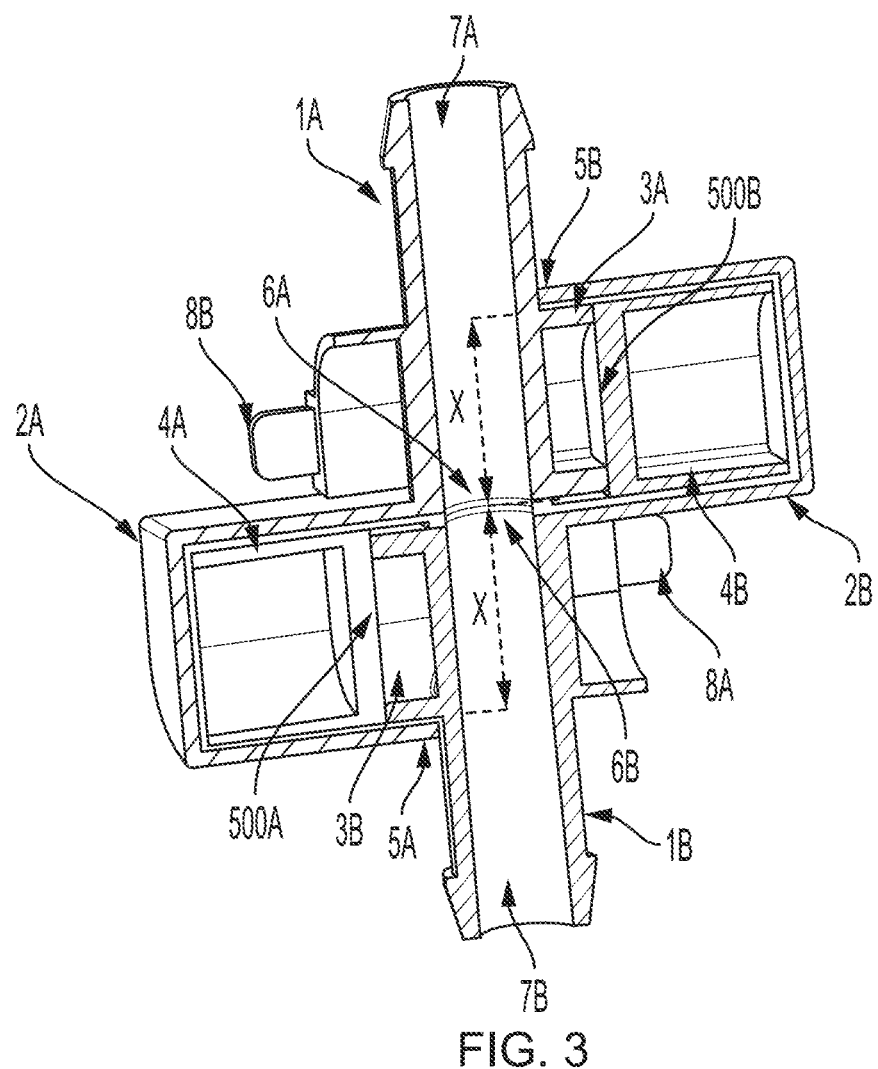
FIG. 3 shows a cross-sectional view of a connector assembly of FIGS. 1a and 1b.

By reciprocal symmetry, a similar, but oppositely directed, longitudinal urging force urges the fluid flow opening (6A) of the connector towards the fluid flow opening (6A) of the connector, thereby assisting in providing a secure interface between the peripheral edges of the fluid flow openings (6A, 6B) of the connector and the reciprocal connector, when the two connectors are connected as shown in FIG. 3. Preferably, the provision of a tapering bore of a socket part dimensioned for generating a longitudinal urging force upon a received socket part, by abutment therewith, is applicable to each embodiment of the invention described herein.

A closure part (4A) is arranged to openably close the fluid flow opening (6A) of the connector and to receive an urging force from the received plug part (3B) of the reciprocal connector. The received urging force displaces the closure part (4A) in a direction crossing the fluid flow opening (6A) of the connector so as to uncover the fluid flow opening (6A). Due to the reciprocal nature of the reciprocal connector, a closure part (4B) of the reciprocal connector is arranged to openably close the fluid flow opening (6B) of the reciprocal connector and to receive an urging force from the received plug part (3A) of the connector. The received urging force displaces the closure part (4B) of the reciprocal connector in a direction crossing the fluid flow opening (6B) of the reciprocal connector so as to uncover the fluid flow opening (6B) of the reciprocal connector. This is done simultaneously with the uncovering of the fluid flow opening (6A) of the connector, as described above. In this way, the connector is thereby connectable to the reciprocal connector with respective fluid flow openings (6A, 6B) aligned in fluid communication, as is shown in the cross-sectional view of the fully-connected connector assembly of FIG. 3.

The closure part (4A) comprises a substantially flat concealment surface portion (400A) which is disposed to overlay the substantially planar fluid flow opening (6A), as shown in FIG. 2b, when the connector is unconnected to a reciprocal connector, but which is displaced by the plug part of the reciprocal connector to reveal the fluid flow opening (6A) when the two connectors are connected as shown in FIG. 3.

FIG. 3 shows how the closure part (4A) of the connector is configured to be displaced into the bore (10A) of the socket part (2A) of the connector by being displaced by an urging/pressing force exerted upon it by an abutting surface of the plug part (3B) of the reciprocal connector. Simultaneously, the closure part (4B) of the reciprocal connector is configured to be displaced into the socket part (2B) of the reciprocal connector by being displaced by an urging/pressing force exerted upon it by an abutting surface of the plug part (3A) of the connector.

In addition, the plug part (3B) of the reciprocal connector is configured to be inserted into the bore (10A) of the socket part (2A) of the connector to retain the displaced closure part (2A) of the connector within the socket part (2A) of the connector. Simultaneously, the plug part (3A) of the connector is configured to be inserted into the socket part (2B) of the reciprocal connector to retain the displaced closure part (2B) of the reciprocal connector within the socket part (2B) of the reciprocal connector.

A recess (5A) is formed within the peripheral edge of the opening of the socket part (2A) of the connector and is configured and dimensioned to receive the outer diameter of the fluid flow passageway part (1B) of the reciprocal connector when the connector and reciprocal connector are fully connected as shown in FIGS. 1a, 1b and 3. Similarly, a recess (5B) is formed within the peripheral edge of the opening of the socket part (2B) of the reciprocal connector and is configured and dimensioned to receive the outer diameter of the fluid flow passageway part (1A) of the connector when the reciprocal connector and connector are fully connected as shown in FIGS. 1a, 1b and 3.

The connector, and the reciprocal connector, each possess a pair of parallel snap-fit latching mechanisms integrally formed upon the outer surface of the respective connectors for retaining the connector and the reciprocal connector together in the attached state. The snap-fit mechanisms each comprise a resiliently flexible protruding male part (8A, 8B) formed upon either one of the connector and the reciprocal connector, configured to be pushed into a receiving through-opening of a female part (9A, 9B) formed upon either one of the reciprocal connector and the connector thereby interlocking the components together. Each of the protruding male parts (8A, 8B) of the connector or reciprocal connector has a tapered barb formation at its outer terminal configured bear against an inner peripheral edge of the entry end of a receiving through-opening of the respective female part (9A, 9B). The tapering nature of the barb formation is thereby deflected slightly by the reactive force exerted by the inner peripheral edge of the receiving through-opening during the pushing operation and once the barb has fully passed through the respective through-opening its resilience causes it snap-fit back against a peripheral edge of the exit end of the receiving through-opening thereby interlock the components. Each flexible protruding male part (8A, 8B) is disposed upon an outer surface of the respective connector, or reciprocal connector, at a location offset to one side of a plane containing the fluid flow opening (6A, 6B) of the respective connector. Similarly, each though-opening of each female part (9A, 9B) is disposed upon an outer surface of the respective connector, or reciprocal connector, at a location offset to the opposite side of the plane containing the fluid flow opening (6A, 6B) of the respective connector. The offset or the male parts matches the offset of the female parts (albeit in the opposite directions relative to the plane) so that the male parts of the connector align with the female parts of a reciprocal connector (and vice versa) when the plug parts of a connector are aligned to be plugged into the socket parts of a reciprocal connector (and vice versa).

In its lateral shape, the closure part (4A) of the connector (and of the reciprocal connector, 4B) is dimensioned and shaped to fill the lateral area of the inner bore (10A) of the socket part (2A) of the connector (or of the reciprocal connector, 2B) and has a terminal end surface (500A, 500B) which extends laterally across the inner bore of the socket part in question so as to laterally fill the bore. This terminal end surface provides a bearing surface of the closure part against which a terminal end of the plug part (3B) of the reciprocal connector (or of the connector, 3A) may abut to impart an urging force to displace the closure part of the connector (or the reciprocal connector) in a direction moving it in to the bore (10A) of the socket part (2A) of the connector (or the reciprocal connector, 10A and 2B). In its longitudinal shape, the closure part (4A) of the connector (and of the reciprocal connector, 4B) is dimensioned and shaped to only partially fill the longitudinal length of the inner bore of the socket part (2A) of the connector (or of the reciprocal connector, 2B) such that the bore may fully accommodate the displacement of the closure part along it when the connector and reciprocal connector are connected, as shown in FIG. 3. In this way, the closure part of the connector is configured for receiving the urging force from the plug part of the reciprocal connector when that plug part is received within the socket part of the connector.

The plug part (3A) and the socket part (2A) are located upon the outer surface of the fluid flow passageway part (1A) adjacent to opposite respective sides of the fluid flow opening (6A), being separated in a direction transverse to the axis (7A) of the fluid flow passageway part, as well as being separated in a direction axially along the axis of the fluid flow passageway part. The longitudinal axes of the plug part (3A) and the socket part (2A) are generally parallel to each other, and transverse to, but coplanar with, the longitudinal axis of the fluid flow passageway. This means that when the connector is rotated through 180 degrees around an axis perpendicular to the axis of the fluid flow passageway and perpendicular to the bore of the socket part, the result is to provide the orientation necessary for a reciprocal connector to connect to the connector as described above, and as shown in FIGS. 1a, 1b and 3. To this extent, a reciprocal connector, when connected to a connector, is identical to the connector when rotated through the aforesaid 180 degrees. Consequently, the fluid flow opening, the socket part and the plug part of both the connector and the reciprocal connector are configured such that the connector is connectable to the reciprocal connector to position the longitudinal axis of respective fluid flow passageways thereof in mutually coaxial alignment.

The plug part (3A) of the connector is configured for insertion into the socket part (2B) of the reciprocal connector, and concurrently the plug part (3B) of the reciprocal connector is configured for insertion into the socket part (2A) of the connector, to connect the connectors together so that the fluid flow passageway part (1A) of the connector is urged against the fluid flow passageway part (1B) of the reciprocal connector to urge respective fluid flow openings (6A, 6B) together.

This is achieved by forming the connector such that the longitudinal position of the plug part (3A) of the connector (or the reciprocal connector) and the longitudinal position of the socket part (2A) of the connector (or the reciprocal connector) are such that:

(3) The outer surface of the plug part (3A) which is arranged to engage the inner bore surface of the socket part (2B) of the reciprocal connector, and which is also furthest from the fluid flow opening (6A), is also longitudinally separated from the fluid flow opening (6A) by a predetermined longitudinal separation (X, see FIG. 3); and (4) The inner bore surface of the socket part (2A) which is furthest from the fluid flow opening (6A) and which is also arranged to engage the outer surface of the plug part (3B) of the reciprocal connector, is also longitudinally separated from the fluid flow opening (6A) by the same predetermined longitudinal separation (X, see FIG. 3).

This ensures an interference fit between the plug part and the socket part and between the peripheral edges of the opposing fluid flow openings (6A, 6B).

Figure 4:
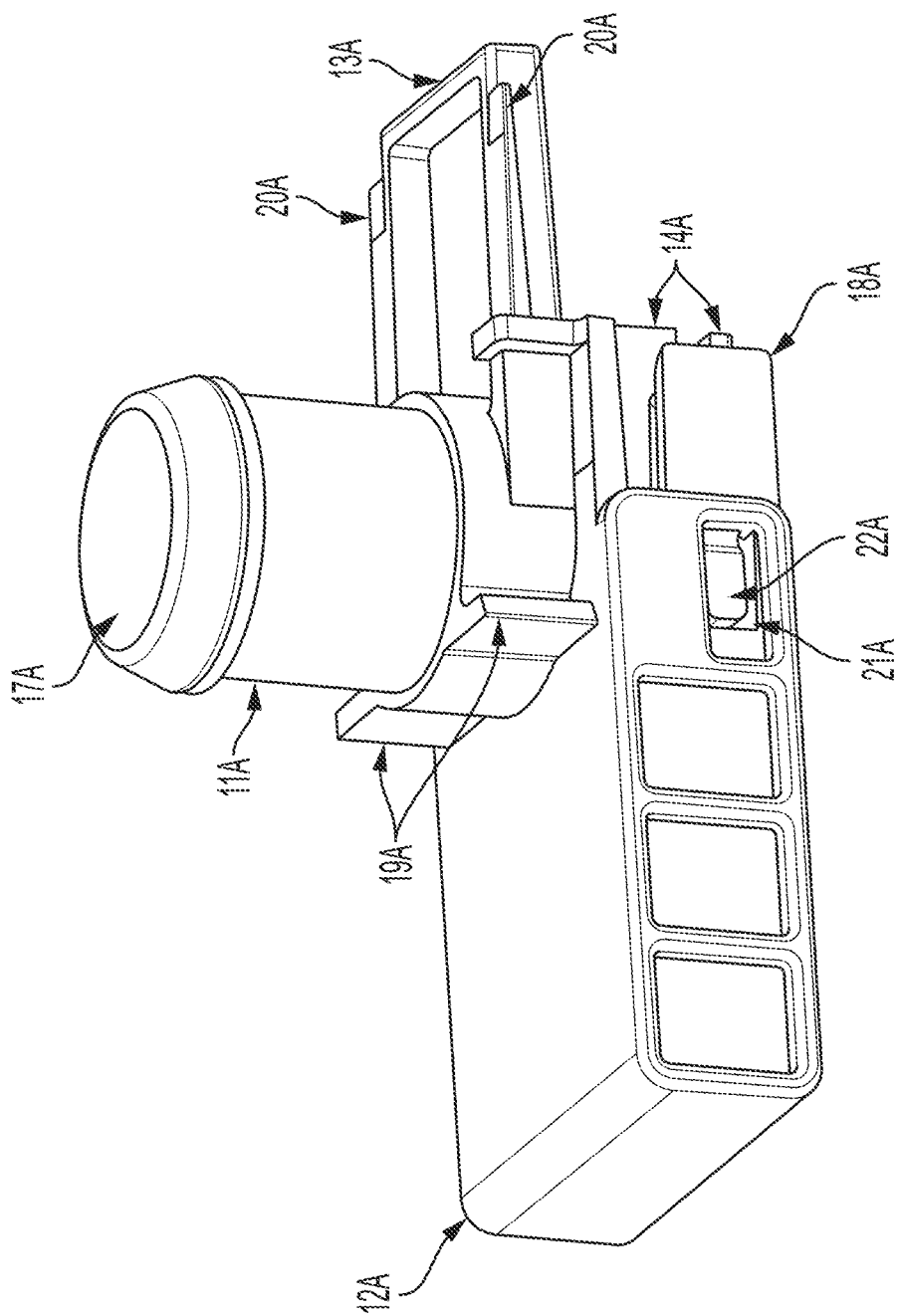
FIG. 4 shows a perspective view of a connector for forming a part of a connector assembly.
Figure 5:
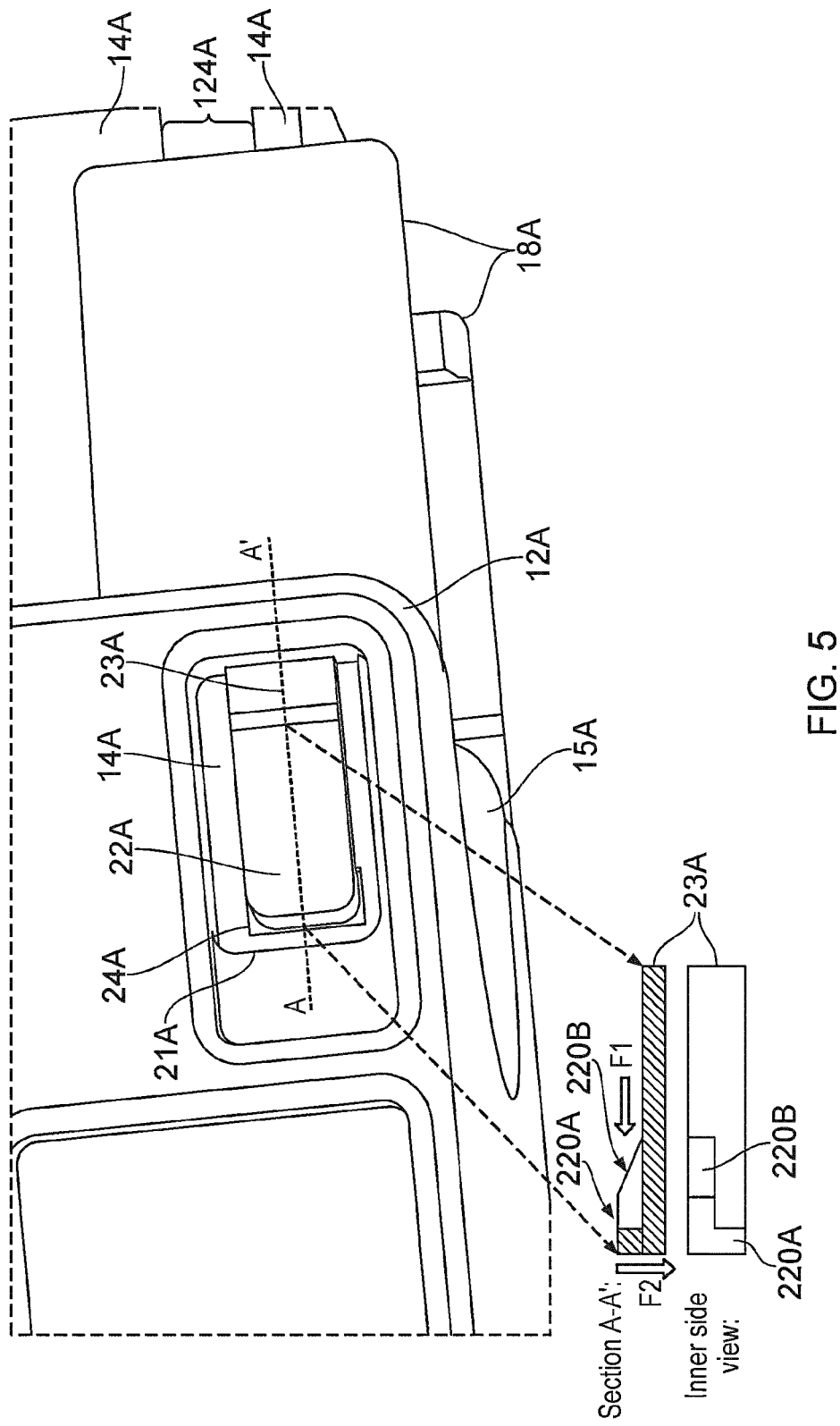
FIG. 5 shows a perspective view of the connector of FIG. 4.
Figure 6:
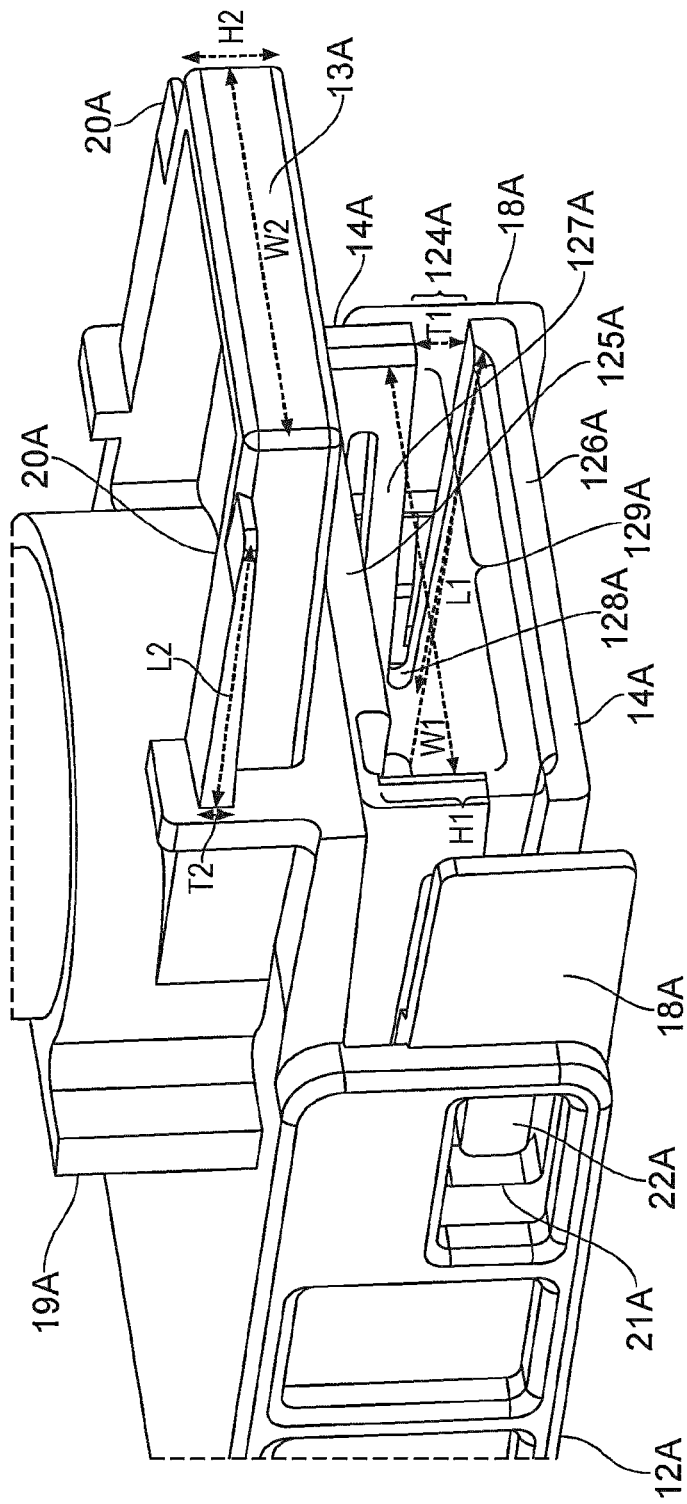
FIG. 6 shows a perspective view of the connector of FIG. 4.
Figure 7:
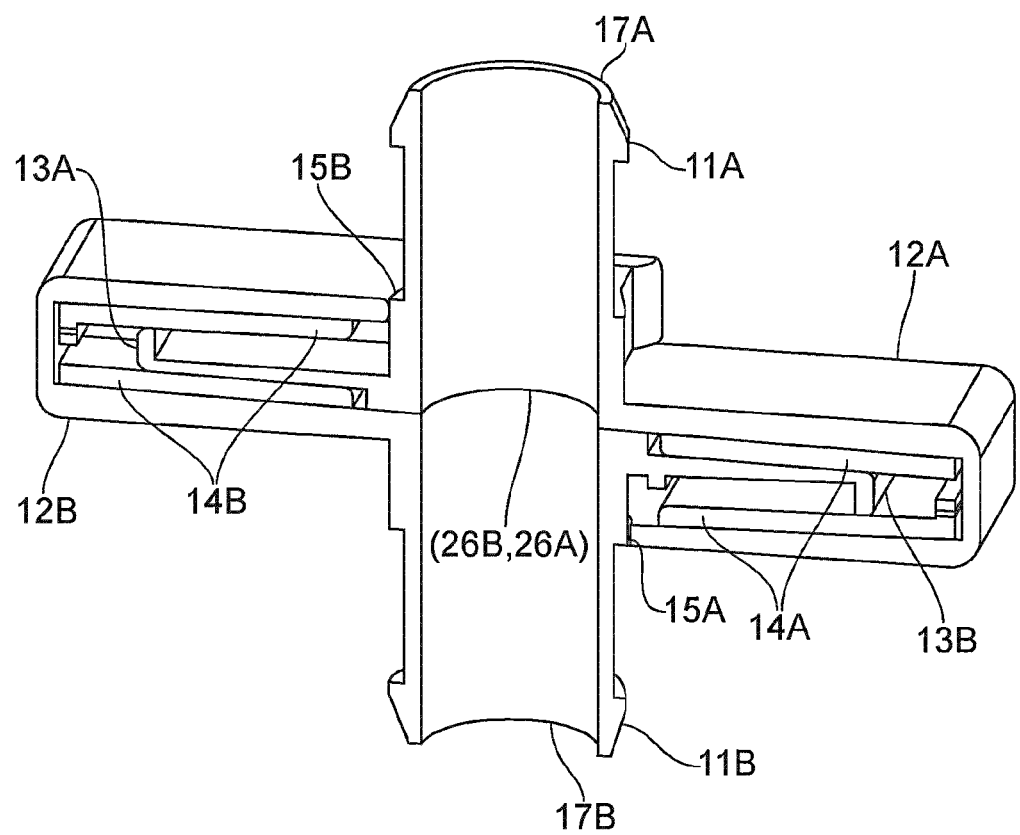
FIG. 7 shows a cross-sectional view of a connector assembly comprising two of the connectors of FIG. 4.
Figure 8:
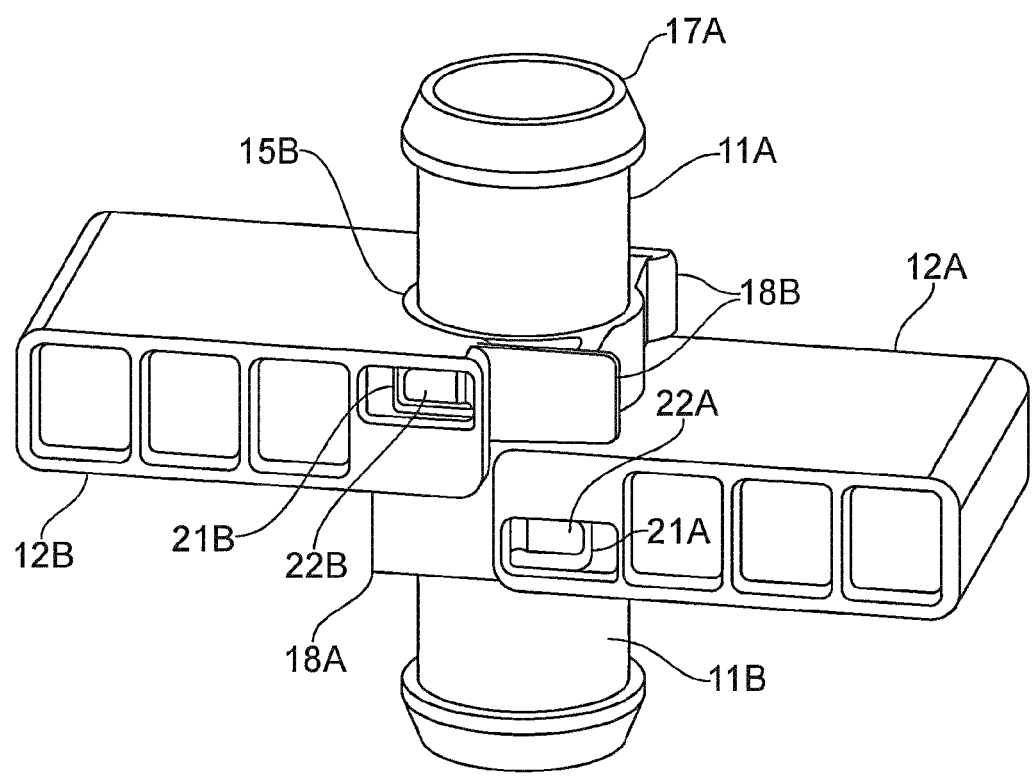
FIG. 8 shows a perspective view of a connector assembly of FIG. 7.

FIGS. 4 to 9 show perspective views and cross-sectional views of a connector according to another embodiment of the invention. It is to be understood that a reciprocal connector is also as shown in FIG. 4. FIGS. 7, 8 and 9 show a connector assembly comprising two of the connectors shown in FIGS. 4 to 6, namely a connector and a reciprocal connector connected together.

The connector comprises a fluid flow passageway part (17A, or reciprocally 17B) defining a fluid flow opening (26A, or reciprocally 26B). A socket part (12A, or reciprocally 12B) is located upon the fluid flow passageway part adjacent to the fluid flow opening. A plug part (13A, or reciprocally 13B) is located upon the fluid flow passageway part adjacent to the fluid flow opening (26A, or reciprocally 26B) and spaced from the socket part (12A, or reciprocally 12B) in a direction crossing the fluid flow opening.

The socket part (12A) of the connector is configured to receive within it the plug part (13B) of the reciprocal connector (and vice versa) thereby to connect the socket part of the connector to the plug part of the reciprocal connector. By doing so, the fluid flow opening (26A) of the connector is aligned in register with the fluid flow opening (26B) of the reciprocal connector.

A closure part (14A) is arranged to openably close the fluid flow opening (26A) of the connector and to receive an urging force from the received plug part (13B) of the reciprocal connector. The received urging force displaces the closure part (14A) in a direction crossing the fluid flow opening (26A) of the connector so as to uncover the fluid flow opening (26A). Due to the reciprocal nature of the reciprocal connector, a closure part (14B) of the reciprocal connector is arranged to openably close the fluid flow opening (26B) of the reciprocal connector and to receive an urging force from the received plug part (13A) of the connector. The received urging force displaces the closure part (14B) of the reciprocal connector in a direction crossing the fluid flow opening (26B) of the reciprocal connector so as to uncover the fluid flow opening (26B) of the reciprocal connector. This is done simultaneously with the uncovering of the fluid flow opening (26A) of the connector, as described above. In this way, the connector is thereby connectable to the reciprocal connector with respective fluid flow openings (26A, 26B) aligned in fluid communication, as is shown in the cross-sectional view of the fully-connected connector assembly of FIG. 7 and in FIGS. 8 and 9.

The closure part (14A) comprises a concealment surface portion (not shown) which is disposed to overlay the fluid flow opening (26A), as shown in FIG. 4, when the connector is unconnected to a reciprocal connector, but which is displaced by the plug part of the reciprocal connector to reveal the fluid flow opening (26A) when the two connectors are connected as shown in FIG. 7, FIG. 8 and FIG. 9.

FIG. 7 shows how the closure part (14A) of the connector is configured to be displaced into the socket part (12A) of the connector by being displaced by an urging/pressing force exerted upon it by an abutting surface of the plug part (13B) of the reciprocal connector. Simultaneously, the closure part (14B) of the reciprocal connector is configured to be displaced into the socket part (12B) of the reciprocal connector by being displaced by an urging/pressing force exerted upon it by an abutting surface of the plug part (13A) of the connector.

In addition, the plug part (13B) of the reciprocal connector is configured to be inserted into the socket part (12A) of the connector to retain the displaced closure part (14A) of the connector within the socket part (12A) of the connector. Simultaneously, the plug part (13A) of the connector is configured to be inserted into the socket part (12B) of the reciprocal connector to retain the displaced closure part (14B) of the reciprocal connector within the socket part (12B) of the reciprocal connector.

A recess (15A) is formed within the peripheral edge of the opening of the socket part (12A) of the connector and is configured and dimensioned to receive the outer diameter of the fluid flow passageway part (11B) of the reciprocal connector when the connector and reciprocal connector are fully connected as shown in FIGS. 7 and 8. Similarly, a recess (15B) is formed within the peripheral edge of the opening of the socket part (12B) of the reciprocal connector and is configured and dimensioned to receive the outer diameter of the fluid flow passageway part (11A) of the connector when the reciprocal connector and connector are fully connected as shown in FIG. 7, FIG. 8 and FIG. 9.

The connector, and the reciprocal connector, each possess a pair of parallel snap-fit latching mechanisms (18A, 19A) integrally formed upon the outer surface of the respective connectors for retaining the connector and the reciprocal connector together in the attached state. The snap-fit mechanisms each comprise a resiliently flexible protruding clip part (18A, or reciprocally 18B) formed upon either one of the connector and the reciprocal connector, configured to be pushed over a receiving flange part (19A, or reciprocally 19B) formed upon either one of the reciprocal connector and the connector thereby interlocking the components together. Each of the protruding clip parts (18A, 18B) of the connector or reciprocal connector has a tapered barb formation at its outer terminal configured bear against a terminal peripheral edge of the end of a receiving respective flange part (19A, 19B). The tapering nature of the barb formation is thereby deflected slightly by the reactive force exerted by the terminal peripheral edge of the receiving flange part during the pushing operation and once the barb has fully passed over the respective terminal peripheral edge its resilience causes it snap-fit back against the peripheral edge of the receiving terminal peripheral edge to thereby interlock the components. Each flexible protruding clip part (18A, 18B) is disposed upon an outer surface of the respective connector, or reciprocal connector, at a location offset to one side of a plane containing the fluid flow opening (26A, 26B) of the respective connector. Similarly, each terminal peripheral edge of each flange part (19A, 19B) is disposed upon an outer surface of the respective connector, or reciprocal connector, at a location offset to the opposite side of the plane containing the fluid flow opening (26A, 26B) of the respective connector. The offset or the clip parts matches the offset of the flange parts (albeit in the opposite directions relative to the plane) so that the clip parts of the connector align with the flange parts of a reciprocal connector (and vice versa) when the plug parts of a connector are aligned to be plugged into the socket parts of a reciprocal connector (and vice versa). A flange part and a clip part, offset in this way, is provided at each side (opposite sides) of the fluid flow passageway part (11A, 11B) so as to provide a snap-fit latching mechanism (18A, 19A) at either side of the fluid flow passageway part. This prevents both lateral and rotational movement of the connector and reciprocal connector when the two are fully connected, and both snap-fit latching mechanism are fully engaged as shown in FIG. 9.

In its lateral shape, the closure part (14A) of the connector (and of the reciprocal connector, 14B) is dimensioned and shaped to substantially fill the lateral area of the inner bore of the socket part (12A) of the connector (or of the reciprocal connector, 12B) and has a terminal end surface outwardly presented at the opening of the bore of the socket part (12A) of the connector so as to be accessible to the plug part (13B) of a reciprocal connector. The closure part is hollow in construction and possesses a bore (129A) extending longitudinally in sympathy with the longitudinal axis of the bore of the socket part in which it resides. The bore of the closure part is generally rectangular in cross-sectional shape and is configured and dimensioned to reciprocally match the cross-sectional profile of the plug part (13B) of the reciprocal connector (and, therefore, of the plug part 13A of the connector itself). The accessible terminal end of the closure part possessed an access opening to the bore (129A) of the closure part configured and dimensioned for receiving the plug part (13B) of the reciprocal connector in a close sliding fit, whereby the plug part of the reciprocal connector is insertable into the bore of the closure part (14A) of the connector, and thereby concurrently into the bore of the socket part (12A) of the connector, in a direction parallel to the longitudinal axis of the bore of the closure part and of the socket part of the connector.

The lateral width (W1) and height (H1) of the rectangular bore of the closure part substantially match (but are slightly greater than), respectively, the lateral width (W2) and height (H2) of the plug part of the connector (13A, and 13B of the reciprocal connector) such that the plug part closely fits into the rectangular bore but is able to slide along it. The two lateral side walls of the bore of the closure part, each being of height H1, have formed in them a re-entrant tapering slot (124A) of length L1 which each begins at slot opening of height T1, positioned at the lateral sides of the opening of the bore of the closure part, and terminates at a slot end surface (128A) positioned at the lateral sides of the inner bore wall of the bore of the closure part. Each tapering slot is accessible along its entire length from within the bore of the closure part, being in communication with that bore all along the slot length. The lateral side edges of the plug part of the connector possess a respective tapering wedge formation (20A) of longitudinal length L2, which tapers from thickness T2 at a thicker base end, located at the base of the plug part, to a thinner terminal tip of the tapering wedge in question, located closer to the tip of the plug part (13A) and at a longitudinal distance L2 from the base end of the tapering wedge. The shape and dimensions of each tapering wedge formation (20A) is configured to reciprocally match the shape and dimensions of each tapering slot (124A) such that: T2 is approximately the same as (but slightly less than) T1; L2 is approximately the same as (but slightly more than) L1. The consequence of this dimensioning is that each one of the two tapering wedge formations (20A) is able to be inserted in to a respective one of the two tapering slot formations, and to slide along the respective tapering slot fully so as to abut against a terminal slot end surface (128A). Thus, each tapering slot is dimensioned to accommodate a respective one of the two tapering wedge formations so as to permit the terminal end of each wedge formation to simultaneously abut the respective terminal slot end surfaces (128A) substantially simultaneously and, in doing so, provide a bearing surface within the closure part (14A) against which an urging force may be applied by the inserted plug part (13B, of the reciprocal connector) for urging the closure part longitudinally along the axis of the bore of the socket part (12A) in a direction into the socket part so as to displace the closure part to reveal the fluid flow opening (126A) of the connector.

Referring to FIGS. 4, 5 and 6, the socket part (12A) of the connector possesses a pair of releasable catch mechanisms (21A, 22A), one at each of the two lateral sides of the socket part, which are operable to change from a first state configured to retain the closure part in a position closing the fluid flow opening (as in FIGS. 4, 5 and 6) to a second state configured to permit said displacement of the closure part (as in FIGS. 7, 8 and 9). The releasable catch mechanism is configured for actuation by the terminal tip of a respective one of the two wedge formations (20A) of the plug part (13B) of the reciprocal connector from within the socket part of the connector to change from the first state to the second state by action of receiving the plug part of said reciprocal connector fully within the socket part of the connector.

In particular, with reference to FIG. 5, the releasable catch mechanism comprises a catch tooth part (220A) mounted upon the inwardly-facing surface of the distal end (22A) of a resiliently bendable arm part (23A) formed so as to extend into, and across, an aperture (21A) formed within the lateral side walls of the socket part (one at each side). The arm part extends in parallel to the longitudinal axis of the bore of the socket part, and extends from its proximal end connected to the peripheral edge of the aperture (21A) which is closest to the opening of the bore of the socket part. The catch tooth part (220A) protrudes from the inwardly-facing surface of the arm part transversely towards the opposing lateral side surface of the closure part (14A) so as to be seated within a reciprocally-shaped groove (24A) formed in the side surface of the closure part. This mechanical engagement between the catch tooth part (220A) of the catch mechanism, and the groove (24A) of the catch mechanism, retains the closure part (14A) in position relative to the socked part (12A) to prevent displacement of the closure part relative to the socket part and to maintain the closure part in a position which cover/closes the fluid flow opening (26A) of the connector.

The releasable catch mechanism may comprise an abutment surface configured for abutment by the plug part of the reciprocal connector when received within the socket part of the connector, and the releasable catch mechanism is operable to change from the first state to the second state in response to the abutment between the releasable catch mechanism and the plug part of the reciprocal connector.

The socket part of the connector also comprises a sloping abutment surface (220B) of the releasable catch mechanism. This takes the form of a ramp formation located upon the inwardly-presented surface of the arm part (22A) which also bears the catch tooth part (220A). The sloping abutment surface presents a continuous abutment surface that smoothly rises from the inwardly-presented surface of the arm part and meets with (coincides with) the peripheral edge of the top surface of the catch tooth part (220A). Each releasable catch mechanism is configured such that the terminal tip of a respective one of the two wedge formations (20A) of the plug part (13B) of the reciprocal connector abuts against the sloping abutment surface (220B) from within the socket part of the connector (i.e. extending laterally through a re-entrant slot (124A) of the closure part), as the wedge tip is advanced towards the terminal abutment surface (128A) of the re-entrant slot in question. As this advance progresses, the tip of the wedge urges against (see force F1) parts of the sloping abutment surface increasing further along the 'ramp' shape of that abutment surface, closer to the 'top' of the ramp which is contiguous with the top surface of the catch tooth part (220A). This increasingly urges the resiliently bendable arm part (23A) to react to the urging force to bend in a direction laterally outwardly away from the advancing wedge tip (see force F1). This bending action dislodges the catch tooth part (220A) from the groove (24A) of the catch mechanism so as to release the catch mechanism and permit the closure part (14A) to be displaced into the socket part (12A) as the tip of the abuts the terminal abutment surface (128A) of the re-entrant slot containing the advancing wedge.

In this way, the catch mechanism is changed from the first state to the second state by action of receiving the plug part of said reciprocal connector fully within the closure part of the connector. The closure part comprises the bearing surface configured for receiving the urging force from the plug part of the reciprocal connector, when received within the socket part of the connector, for displacing the closure part to reveal the fluid flow opening of the connector. The bearing surface of the closure part is configured, as described above, such that it receives the urging force from the plug part of the reciprocal connector not before the releasable catch mechanism has changed from the first state to the second state.

Figure 10A:
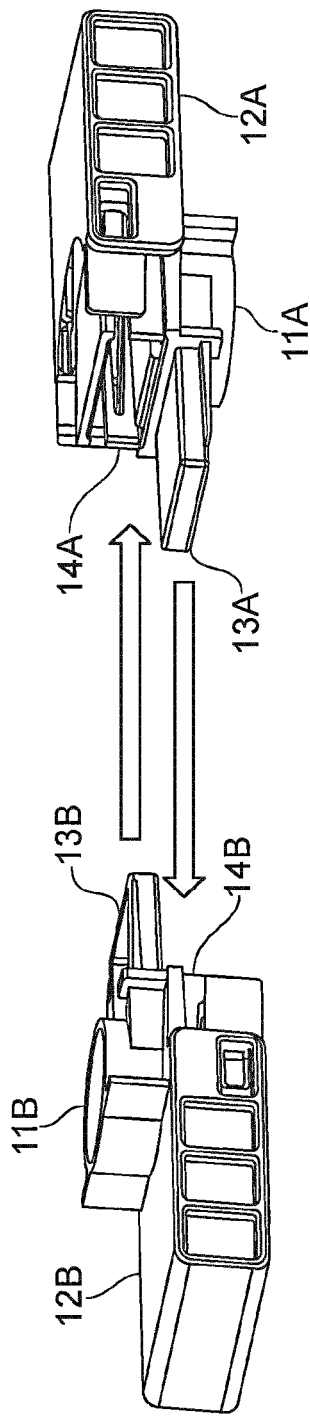
FIG. 10a shows a perspective view of two of the connectors of FIG. 4.
Figure 10B:
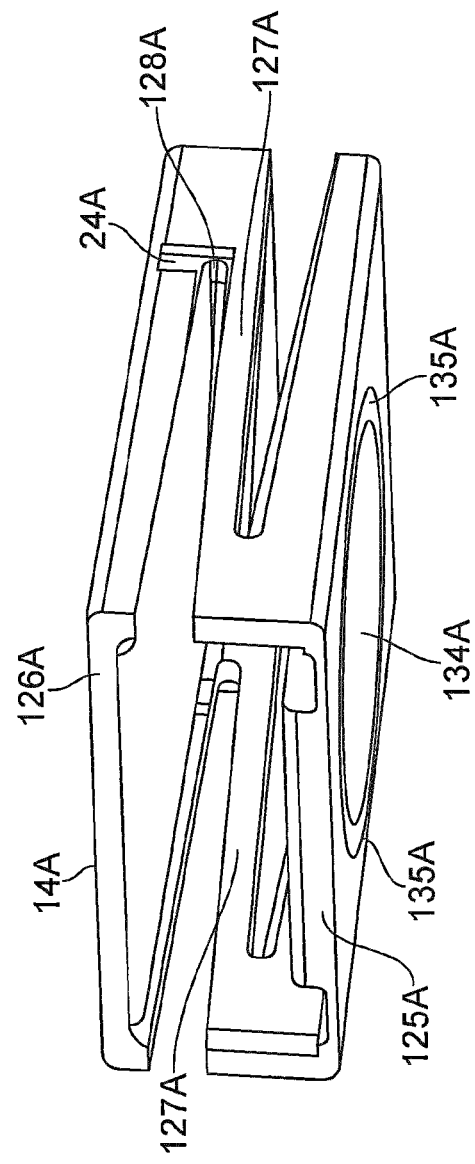
FIG. 10b shows a perspective view of a component part of the connector of FIG. 4.
Figure 11:
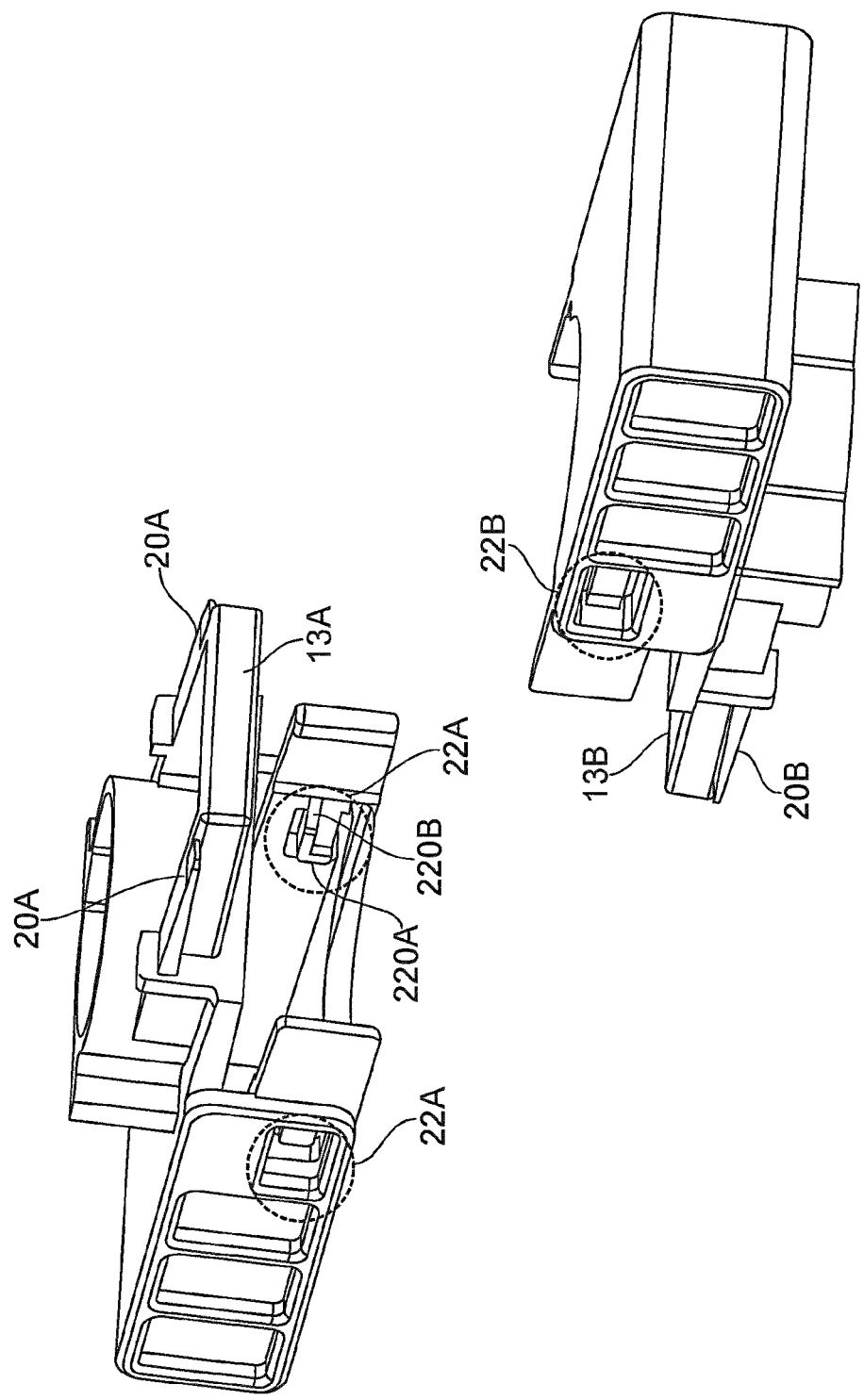
FIG. 11 shows a perspective view of two of the connectors of FIG. 4.

FIGS. 10a, 10b and FIG. 11 illustrate view of the connector and its reciprocal connector, as well as a view of the closure part (14A) in isolation (FIG. 10b). Note that in FIGS. 10a and 11, the hose attachment nozzle portion (17A, 17B) of the fluid flow passageway of the connector is absent, for improved clarity.

The lateral dimensions (i.e. width and height) of the bore of the socket part (12A) is tapered such that the diameter of the opening of the bore of the socket part (12A) exceeds an internal lateral dimensions (i.e. width and height) of the bore axially further along the bore. This means that the bore surface increasingly urges against/abuts the opposing surface of the closure part of the connector as the closure part advances along the bore of the socket part, urged on by the advancing plug part (13B) of the reciprocal connector. This serves to laterally compress the socket part (12A) in the direction perpendicular to its longitudinal axis and parallel to the long axis of the fluid flow part (11A) of the connector. Consequently, the inner bore surface of the compressing closure part similarly increasingly urges against/abuts the opposing surface of the plug part (13B) of the reciprocal connector as the plug part (13B) of the reciprocal connector advances along the bore of the socket part. This urges the fluid flow passageway part of the connector towards the fluid flow passageway part of the reciprocal connector.

Compression of the closure part (14A) is facilitated by provision of a resiliently deformable cantilever spring arm formation in each of the lateral side walls of the closure part. In particular, two parallel cantilever spring arms (127A) connect opposing upper and lower platforms (125A, 126A) of the cover part. The upper and lower platforms are generally planar and mutually parallel, and spaced apart from each other in a direction parallel to the longitudinal axis of the fluid flow part (11A). They form the upper (125A) and lower (126A) parts of the closure part, with the outer surface of the upper platform (125A) also providing a closure surface for directly (but displacably) covering the fluid flow opening (26A) of the connector. One end of the resiliently deformable cantilever spring arm formation (127A) is joined to the upper platform (125A) of the cover part at a location proximal to the opening of the bore of the closure part (14A), while the other end of the resiliently deformable cantilever spring arm formation (127A) is joined to the lower platform (126A) of the cover part at a location axially further inside the bore of the closure part (14A), on the same side. This allows the resiliently deformable cantilever spring arm formation to extend in a direction diagonally transverse to the compressive forces to be experienced by the closure part as it is displaced into the bore of the socket part of the connector. Consequently, this diagonal direction is sympathetic to the operation of the resilient 'springy' action of the cantilever spring arm formation.

FIG. 10b shows a closer direct view of the closure part in islolation. This view shows the concealment surface portion (134A, 135A) of the closure part which, in use, is disposed to overlay the fluid flow opening (26A) when the connector is not connected to a reciprocal connector. The resiliently deformable nature of the closure part, by which it is able to be compressed in a direction transverse to the concealment surface portion within the socket part, permits the closure part to resiliently urge the concealment surface against the parts of the fluid flow passageway surrounding the peripheral edge of the fluid flow opening. The concealment surface portion comprises a flat circular embossed portion (134A) circumscribed by a surface relief ramp formation (135A) contiguously joining the circular embossed portion to the surrounding parts of the concealment surface. The embossed portion is configured to project from the surrounding parts of the concealment surface portion (134A) in a direction into the fluid flow opening (26A) when the connector is not connected to a reciprocal connector, so as to be, in effect, inserted into the fluid flow passageway opening slightly, through the fluid flow opening.

Displacement of the closure part (14A) in a direction crossing the fluid flow opening causes the surface relief ramp formation (135A) to ride over an abutting peripheral edge of the fluid flow opening (26A) thereby to displace the concealment surface portion of the closure part in a direction away from the fluid flow opening. The surface relief ramp formation is annular, or a semi-circular in other examples, and extends along the concealment surface to define a shape reciprocating the shape of a peripheral edge of the fluid flow opening. The compressibility of the closure part, as described above, allows it to compress resiliently in the direction away from the fluid flow opening in response to the surface relief ramp formation riding over an abutting peripheral edge of the fluid flow opening as the closure part is urged into the socket part by the advancing plug part of a reciprocal connector. This has the beneficial effect of separating from the inner bore surface of the socket part (12A) those parts of the concealment surface of the closure part (14A) other than the circular embossed portion (134A) so that those other surfaces are not dragged across the peripheral edge of the fluid flow opening during this displacement. This means that any contaminants that may have accumulated upon those other surfaces are not transferred to the peripheral edge of the fluid flow opening.

The plug part (13A) and the socket part (12A) are located upon the fluid flow passageway part (11A) adjacent to opposite respective sides of the fluid flow opening (26A), being separated in a direction transverse to the axis of the fluid flow passageway part. In addition, the plug part and the socket part are located upon the fluid flow passageway part adjacent to opposite respective sides of the fluid flow opening, being separated in a direction axially along the axis of the fluid flow passageway part. The fluid flow opening, the socket part and the plug part of both the connector and the reciprocal connector are configured, as described above, such that the connector is connectable to the reciprocal connector to position the longitudinal axis of respective fluid flow passageways thereof in mutually coaxial alignment. As described above, the plug part of the connector is preferably configured for insertion into the socket part of the reciprocal connector to connect thereto such that the fluid flow passageway part of the connector is urged against the fluid flow passageway part of the reciprocal connector to urge respective fluid flow openings together.

FIG. 11 shows a closer direct view of the connector part and the reciprocal connector part shown in FIG. 10a, but in which the closure part of each connector part is omitted, for better clarity. This view shows in more detail the inner portions of the socket part of each connector which bear the sloping abutment surface (220B) of the releasable catch mechanism (22A, 22B and 220A, 220B) also shown in FIG. 5.

Figures 12A, 12B:
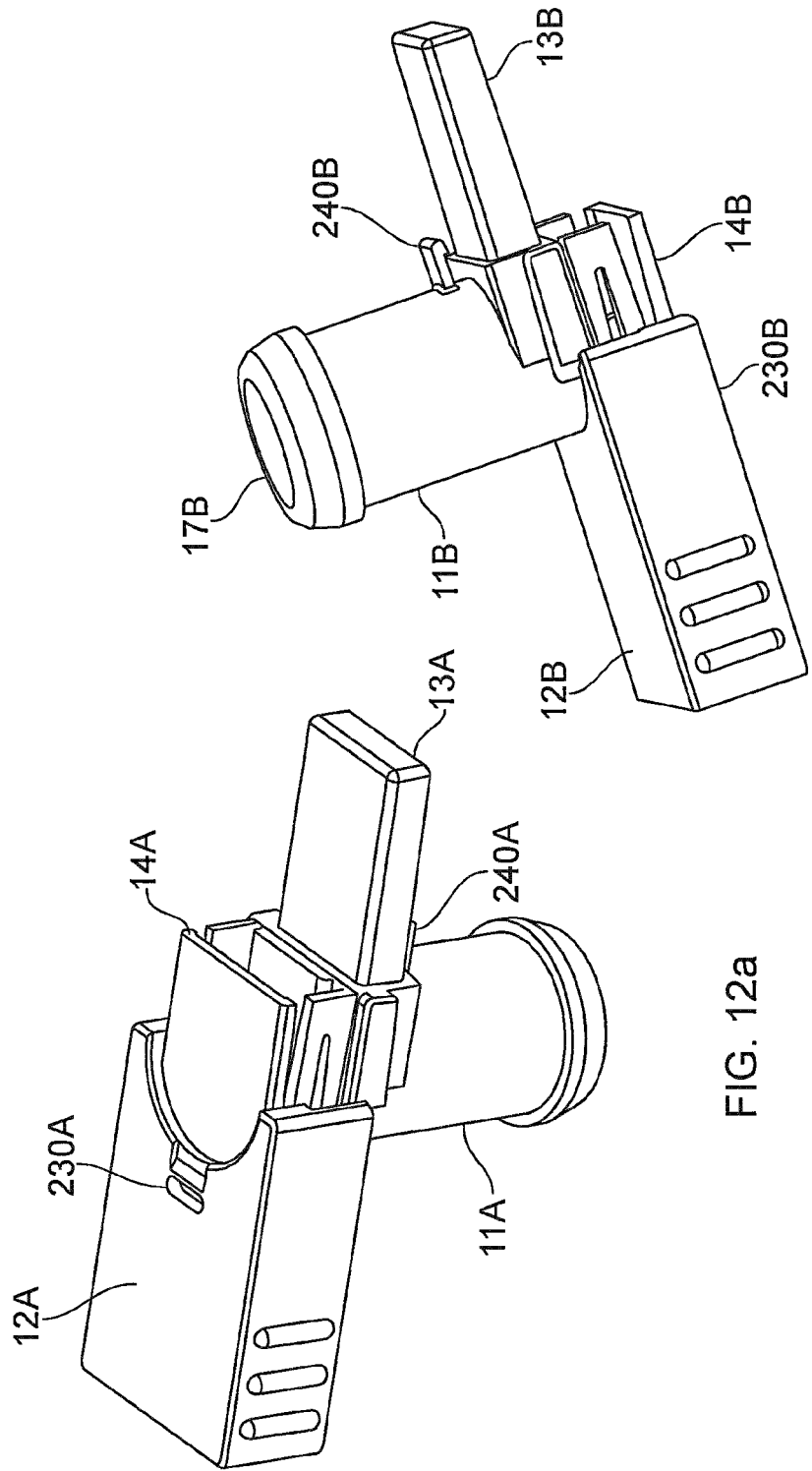
FIGS. 12a and 12b show perspective views of a connector (FIG. 12a) and a reciprocal connector (FIG. 12b)

FIGS. 12a and 12b illustrate perspective views of a connector according to another embodiment of the invention in which the pair of parallel snap-fit latching mechanisms (18A, 19A) described above with reference to FIGS. 4 to 9, is replaced by a different pair of snap-fit latching mechanism (230A, 240A) each of which is integrally formed upon the outer surface of the respective connectors for retaining the connector and the reciprocal connector together in the attached state. The snap-fit mechanisms each comprise a resiliently flexible protruding clip part (240A, and 240B identically on the reciprocal connector) protruding transversely from its proximal end attached to the outer surface of the fluid flow passageway in a direction extending over the plug part (13A) and parallel to the longitudinal axis of the plug part, terminating at its distal end which bears a terminal tooth or barb formation pointing towards the opposing surface of the plug part (13A). The protruding clip part is spaced from the adjacent surface of the plug part by a spacing dimensioned to snugly fit within it a wall of the socket part of the reciprocal connector (12B). That wall of the reciprocal connector contains a notch formation (230B, and 240A identically on the connector) dimensioned to receive, in a snap-fit manner, the terminal tooth/barb formation of the protruding clip part when the connector and the reciprocal connector are fully connected together thereby to hold the connectors together. Both the connector and the reciprocal connector possess this configuration of one resiliently flexible protruding clip part (240A, and 240B identically on the reciprocal connector) disposed at one side (both laterally and longitudinally) of the fluid flow opening of the connector, and one notch formation (230B, and 240A identically on the connector) disposed at the other side (both laterally and longitudinally) of that fluid flow opening.

Each flexible protruding clip part is disposed at a location offset to one side of a plane containing the fluid flow opening of the respective connector. Similarly, each notch formation is disposed at a location offset to the opposite side of the plane containing the fluid flow opening of the respective connector. The offset or the clip parts matches the offset of the notch formations (albeit in the opposite directions relative to the plane) so that the clip parts of the connector align with the notch formations of a reciprocal connector (and vice versa) when the plug parts of a connector are aligned to be plugged into the socket parts of a reciprocal connector (and vice versa). A notch formation and a clip part, offset in this way, is provided at each side (opposite sides) of the fluid flow passageway part (11A, 11B) so as to provide a snap-fit latching mechanism at either side of the fluid flow passageway part. This prevents both lateral and rotational movement of the connector and reciprocal connector when the two are fully connected, and both snap-fit latching mechanism are fully engaged as shown in FIG. 16b.

FIGS. 13a to 13d show a sequence of intermediate positions of the connector and the reciprocal connector as the two connectors are connected together. FIGS. 14a and 14b also show a penultimate and a final position of the reciprocal connector as the two connectors are connected together.

In particular, the notch formation of the connector and the reciprocal connector (230A, 230B) is formed as a through-opening which is simultaneously accessible by the tooth/barb formation of a resiliently flexible protruding clip part (240A, and 240B identically on the reciprocal connector) from the outer surface of the socket part and by an inner resiliently flexible protruding clip part (235A, and 235B identically on the reciprocal connector) formed at the terminal end of the closure part (14A, 14B) of the connector and the reciprocal connector. Each inner resiliently flexible protruding clip part comprises a resiliently flexible limb which protrudes across the terminal end of the bore of a closure part from its proximal end, which is joined to the terminal end of a closure part, to its distal end/tip which is not joined to anything but is disposed within the notch formation of the socket part containing the closure part in question. When in the un-displaced state, the closure part of the connector and the reciprocal connector is positioned such that the distal tip of the inner resiliently flexible protruding clip part engages with a respective notch formation to retain the closure part in position within the bore of the socket part and covering the fluid flow opening of the connector in question.

Figure 13A:
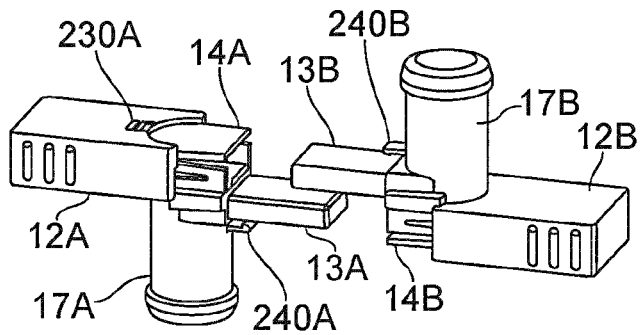
FIGS. 13a, 13b, 13c, 13d show cross-sectional and perspective views of a connector (FIG. 12a) and a reciprocal connector (FIG. 12b) of FIGS. 12a and 12b.
Figure 13B:
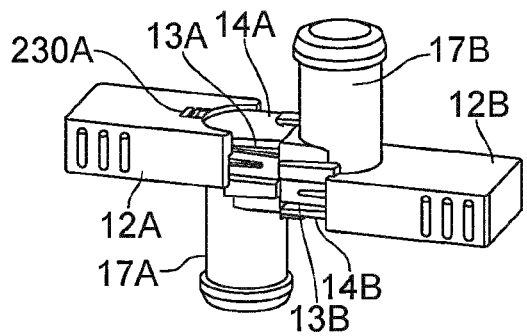
Figure 13C:
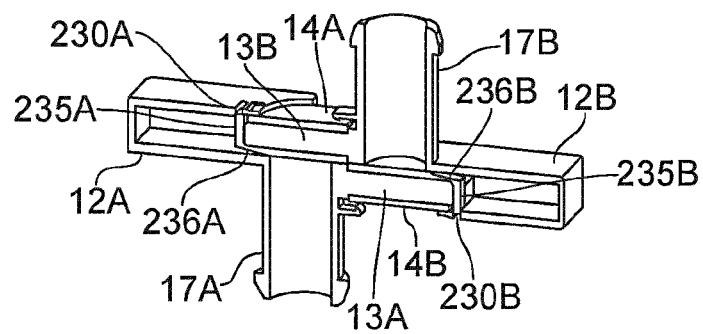
Figure 13D:
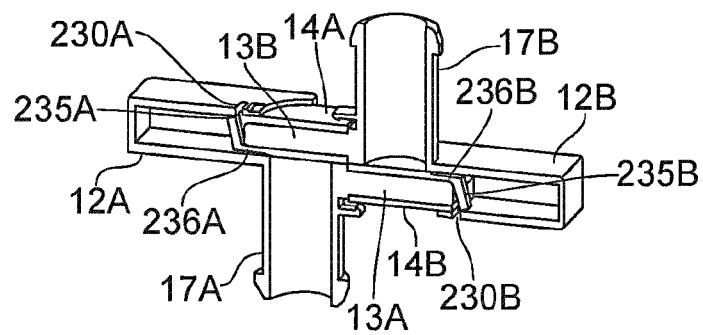
Figure 14A:
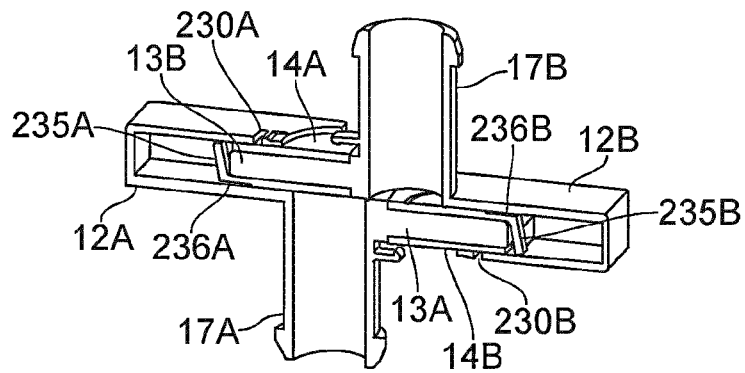
FIGS. 14a and 14b show cross-sectional views of a connector (FIG. 12a) and a reciprocal connector (FIG. 12b) of FIGS. 12a and 12b.
Figure 14B:
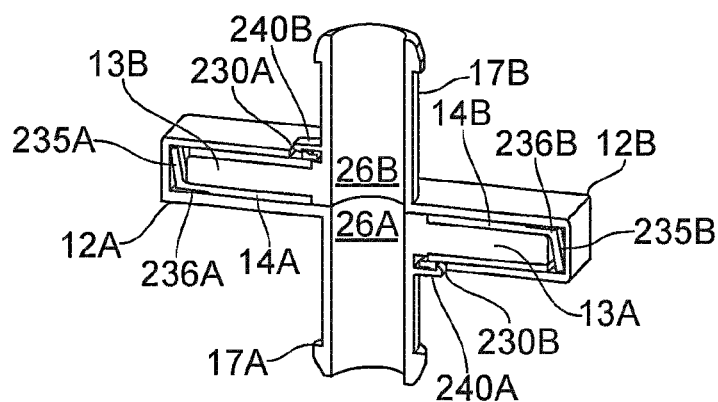
Figure 15A:
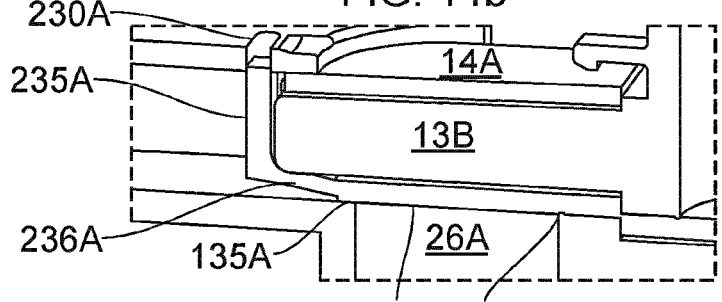
FIGS. 15a and 15b show cross-sectional views of a connector (FIG. 12a) and a reciprocal connector (FIG. 12b) of FIGS. 12a and 12b.
Figure 15B:
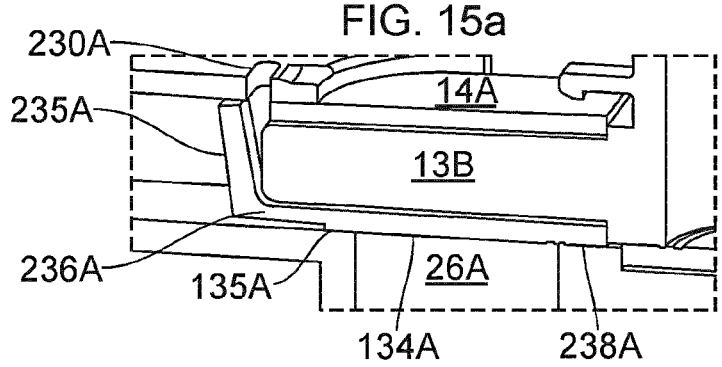

However, upon insertion of a plug part (13A, 13B) of another such connector to such an extent that the terminal end of the inserted plug part presses against the inner resiliently flexible protruding clip part (235A, and 235B identically on the reciprocal connector), as shown in FIG. 13c, internally from within the bore of the closure part. In response to such a pressing or urging force from the abutting plug part, the abutted surface of the inner resiliently flexible protruding clip part is able to rotate about its proximal end so as to displace its distal tip away from the notch formation (230A, 230B). This is achieved by action of the flexing of the closure part at a flexure region (236A, 236B) formed by a relatively thinner portion of the closure part at which proximal end of the inner resiliently flexible protruding clip part is joined to the adjoining portions of the closure part. This process is illustrated in FIGS. 15a and 15b.

Figure 16A:
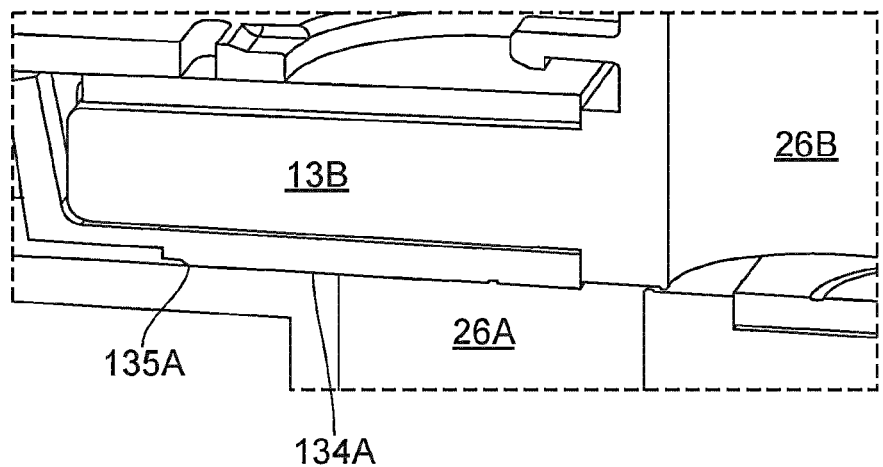
FIGS. 16a and 16b show cross-sectional views of a connector (FIG. 12a) and a reciprocal connector (FIG. 12b) of FIGS. 12a and 12b.
Figure 16B:
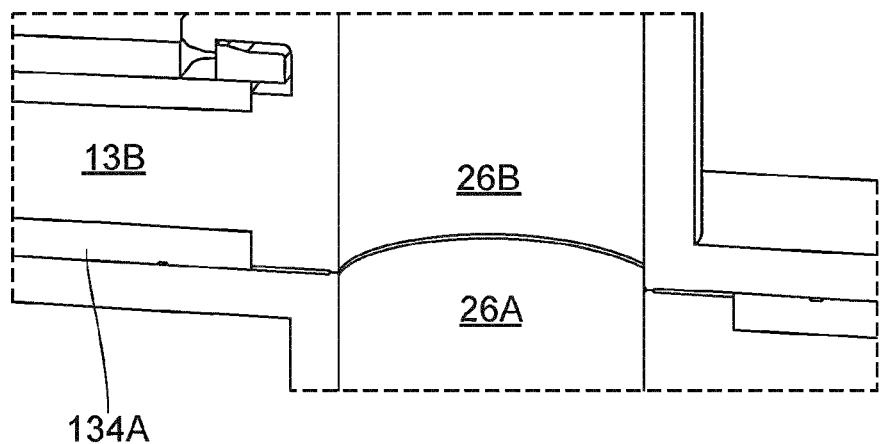
Figure 17A:
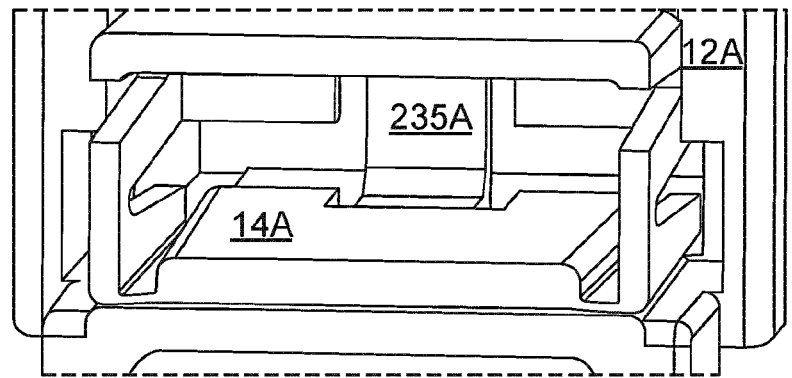
Figure 17B:
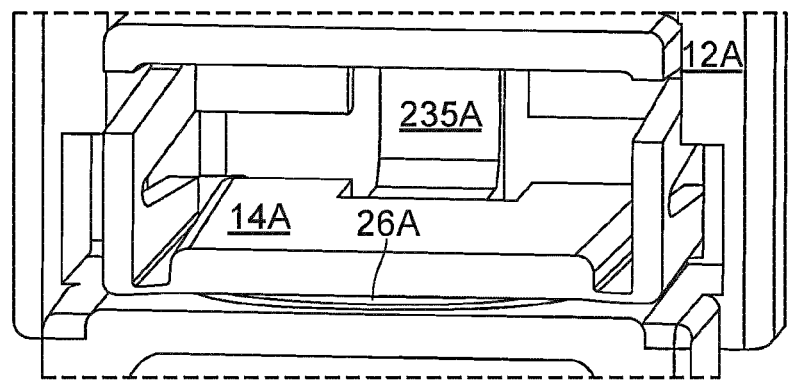
Figure 17C:
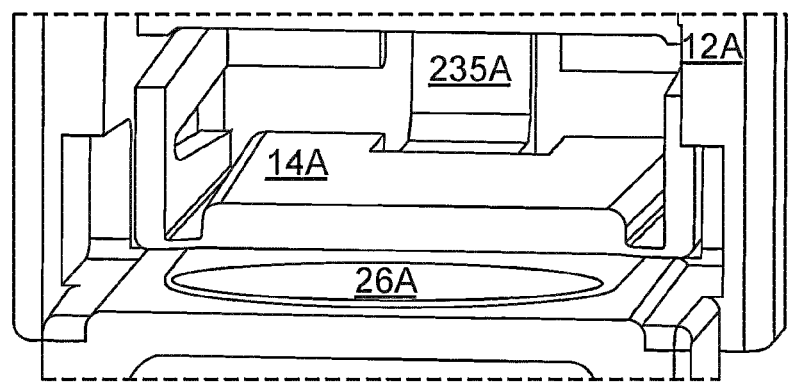

Referring to FIGS. 15a and 15b, and FIGS. 16a and 16b, and in FIGS. 17a, 17b and 17c, in more detail, there is shown the process of the displacement of the closure part (14A) in a direction crossing the fluid flow opening. This causes the surface relief ramp formation (135A) to ride over an abutting peripheral edge of the fluid flow opening (26A) thereby to displace the concealment surface portion of the closure part in a direction away from the fluid flow opening. As described above, the surface relief ramp formation is annular, or a semi-circular in other examples, and extends along the concealment surface to define a shape reciprocating the shape of a peripheral edge of the fluid flow opening. The compressibility of the closure part, as described above, allows it to compress resiliently in the direction away from the fluid flow opening in response to the surface relief ramp formation riding over an abutting peripheral edge of the fluid flow opening as the closure part is urged into the socket part by an advancing plug part of a reciprocal connector. This has the beneficial effect of separating from the inner bore surface of the socket part (12A) those parts of the concealment surface of the closure part (14A) other than the circular embossed portion (134A) so that those other surfaces are not dragged across the peripheral edge of the fluid flow opening during this displacement. This means that any contaminants that may have accumulated upon those other surfaces are not transferred to the peripheral edge of the fluid flow opening.

Disengagement of the distal tip (235A) away from the notch formation (230A) permits displacement of the closure part along the bore of the socket part thereby to reveal the previously covered fluid flow opening (26A) of the connector (similarly for the reciprocal connector), as shown in FIGS. 16a and 17b (partially revealed fluid flow openings) and FIGS. 16b and 17c (fully revealed and aligned fluid flow openings).

Figure 18A:
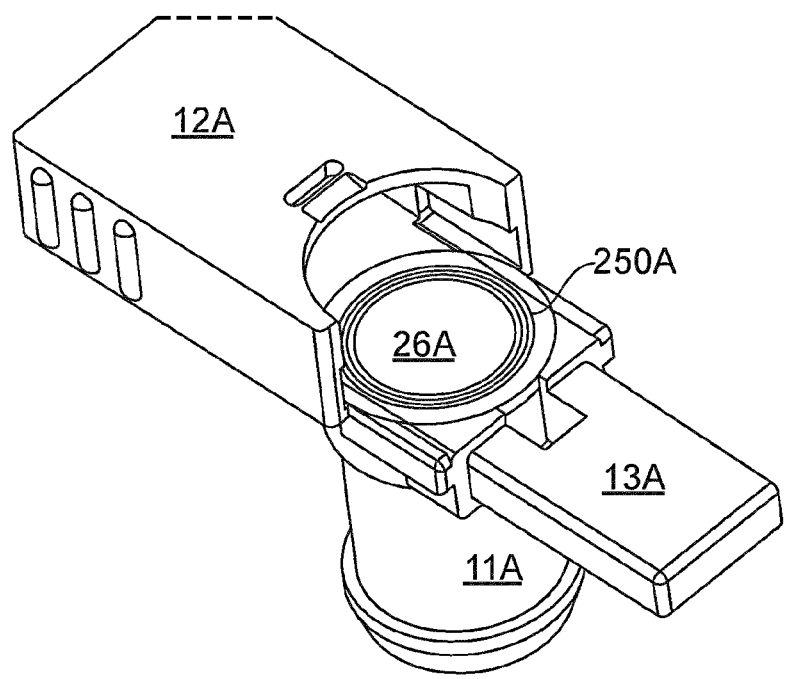
FIGS. 18a and 18b show perspective views of a connector.
Figure 18B:
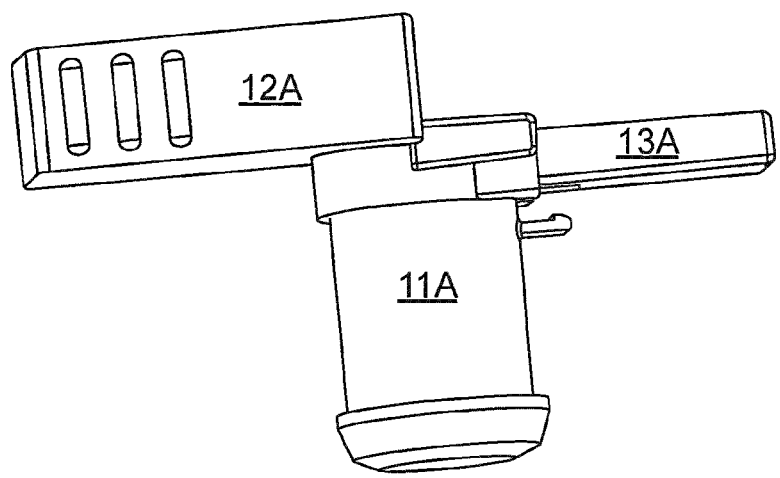
Figure 19:
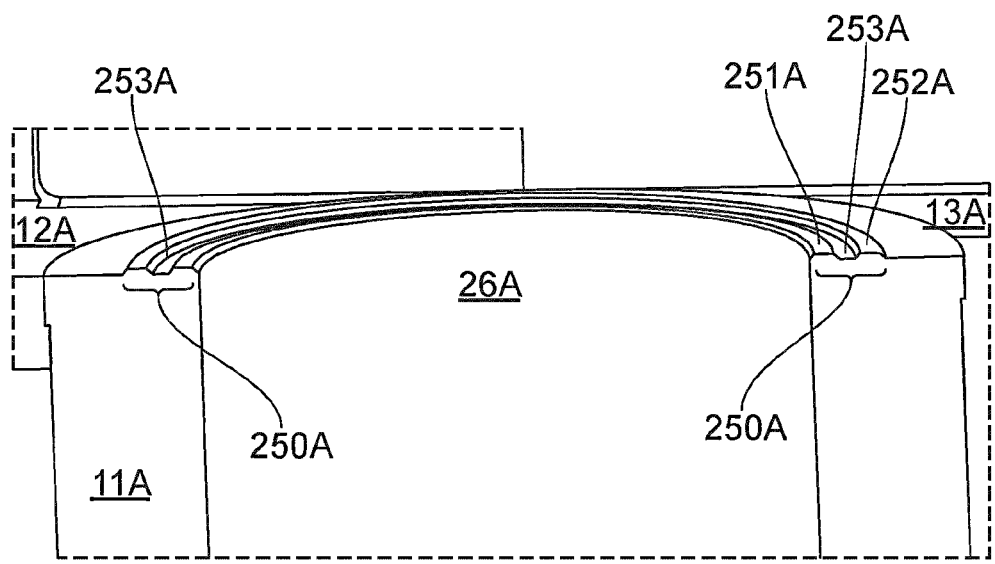
FIG. 19 shows a cross-sectional view of a connector of FIGS. 18a and 18b.

FIGS. 18a and 18b show two perspective views of the connector (or reciprocal connector) of FIGS. 12a and 12b. FIG. 19 shows a cross-sectional view of the connector of FIGS. 18a and 18b into a cross-sectional plane containing the longitudinal axes of both the fluid flow passageway and the bore of the socket part of the connector. These views deliberately omit the associates closure part of the connector in question, to aid clarity, and to better reveal concentric rings (250A) embossed around the fluid flow opening of the connector comprising two circular rings (251A, 251B) of equal embossed height and embossed thickness and in the surface between them define a trough (253A) of uniform depth and width as defined between opposing circumferential edges of the two concentric rings. These rings play a role in the aseptic aspect of the invention, in preferred embodiments. In preferred embodiments, the surface of the fluid flow part of the connector surrounding the periphery of the fluid flow opening (26A, or reciprocally 26B) bears at least one, optionally two (as in FIGS. 18a and 19), or optionally three or more such concentric surface embossments each defining a ring (e.g. circular) of raised surface material of the fluid flow part configured to abut against the opposing surface of the closure part of the connector when the fluid flow opening is closed and the connector is not connected to a reciprocal connector.

Each ring may be considered as a "bump" over which the displaced closure part most traverse when it is displaced during the act of connection to a reciprocal connector, as described above. The physical action of "bumping" over the embossment serves to shake loose and wipe any debris (e.g. contaminants) present upon the abutting face of the displaced closure part as it is pushed past the fluid pathway opening during connection. When two or more concentric such ring embossments are provided, as shown in FIGS. 18a and 19, then the wiped-away debris may be naturally collected within the trough formed between the two concentric rings.

Figure 20B:
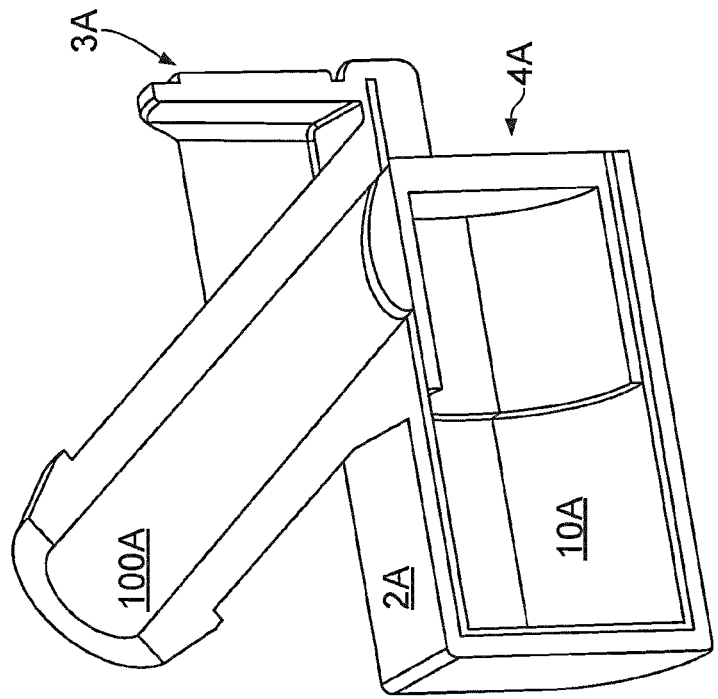
FIGS. 20a and 20b show cross-sectional and perspective views of a connector.
Figure 20A:
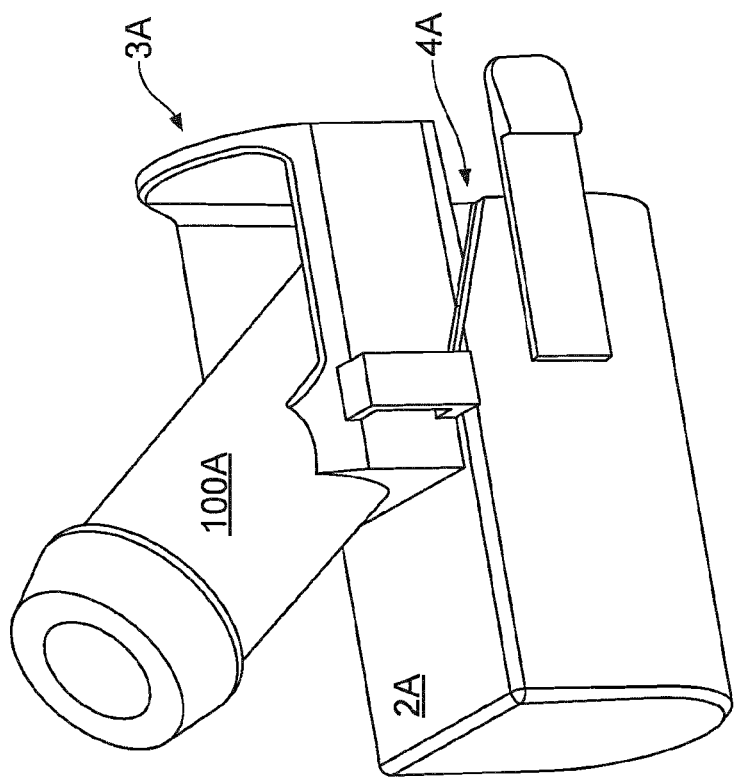

FIGS. 20a and 20b show a perspective view (FIG. 20a) and a cross-sectional view (FIG. 20b) of a variant of the connector design shown in FIG. 1a and FIG. 1b, in which the fluid flow passageway part 100A is configured with its longitudinal fluid flow axis oblique to the axis of the bore (10A) of the socket part. The location of the plug part (3A) of the connector, the socket part (2A) and the closure part (4A), and all other parts of the connector (and its reciprocal) are as described above with reference to FIGS. 2a and 2b. FIGS. 21a and 21b show a perspective view (FIG. 21a) and a cross-sectional view (FIG. 21b) of the connector of FIGS. 20a and 20b when connected to a reciprocal such connector.

FIGS. 22a and 22b show a perspective view (FIG. 22a) and a cross-sectional view (FIG. 22b) of a variant of the connector design shown in FIG. 20a and FIG. 20b, in which the plug part (3A) of the connector possesses a pair of parallel, elongated finger portions (301A, 302A) of equal length and width and each laterally spaced from the other in parallel opposition by a uniform spacing (306A) dimensioned to permit each finger part to resiliently flex towards the other finger part in response to lateral forces applied to them. Each finger portion extends from its respective proximal end which is joined to the surface of the plug part (3A) adjacent to the fluid flow part (100A) of the connector, and terminates at a tapered distal end defined by a half hemispherical surface (303A, 304A) disposed to radially, and longitudinally, outwardly present a half hemispherical bearing surface.

Each finger portion extends in a direction parallel to the axis of the bore (10A) of the socket part of the connector. The pair of finger portions are dimensioned collectively for full insertion through a through-opening (401A) formed axially along the inside of the closure part (400A). The axis of the through-opening is coaxial with the axis of the bore (10A) of the socket part containing the closure part in question. The socket part (2A) possesses a terminal end wall comprising a through-opening (200A) which presents a circumferential peripheral edge dimensioned to receive and admit, concurrently, the two adjacent terminal half hemispherical bearing surfaces (303A, 304A) located at the end of each finger portion (301A, 302A) of the plug part when the finger portions are fully inserted into the socket part (2A) and the plug part (3A) has fully displaced the closure part (400A) from the fluid flow opening (26A) to fully reveal the fluid flow opening.

When the connector and reciprocal connector are in this relative position, notch indentations (305A) formed in the radially outer side surfaces of each finger portion of the reciprocal connector, adjacent to its distal end, are configured to engage with the adjacent circumferential peripheral edge of the through-opening (200A) of the terminal end wall of the bore of the socket part (2A) of the connector. Simultaneously, the reciprocal situation occurs between the finger portion of the connector and the circumferential peripheral edge of the through-opening of the terminal end wall of the bore of the socket part of the reciprocal connector. During the act of connection, the two adjacent terminal half hemispherical bearing surfaces located at the end of each finger portion of the plug part, simultaneously bear against the circumferential peripheral edge of the through-opening of the terminal end wall of the bore of the socket part of the connector as the two connectors are pushed together. The half hemispherical tapering of the bearing surfaces (303A, 304A) convert an axial urging force, applied to displace the closure part of a connector, into a transverse flexure force for flexing each respective finger portion towards the other as the bearing surfaces 'ride over' the local part of the circumferential peripheral edge of the through-opening (200A) of the terminal end wall of the bore of the socket part. Once the notch indentation upon a given finger portion aligns with local part of the circumferential peripheral edge of the through-opening, then in a snap-fit action the notch indentation engages with (receives) the local part of the circumferential peripheral edge. This defines a mechanical latch mechanism for retaining the two connectors in a connected state.

Figure 23A:
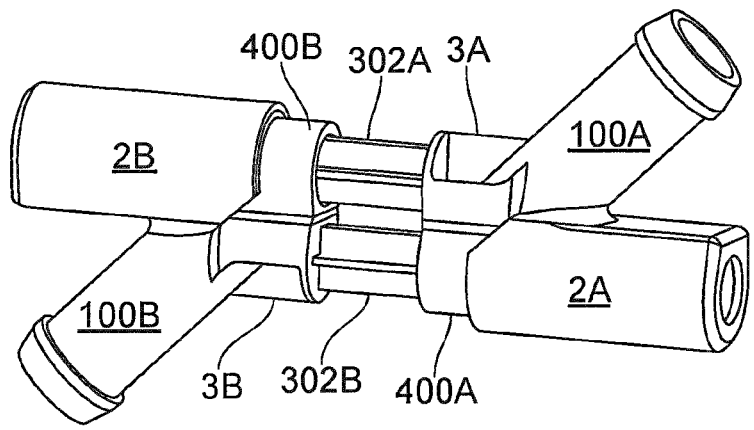
FIGS. 23a, 23b and 23c show perspective views of a connector assembly formed from two connectors of FIGS. 22a and 22b.
Figure 23B:
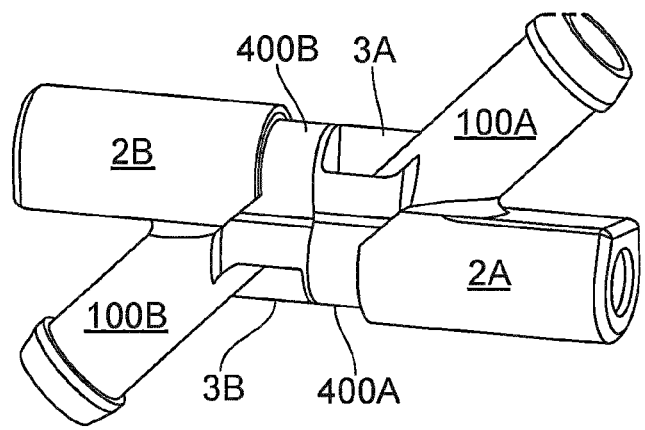
Figure 23C:
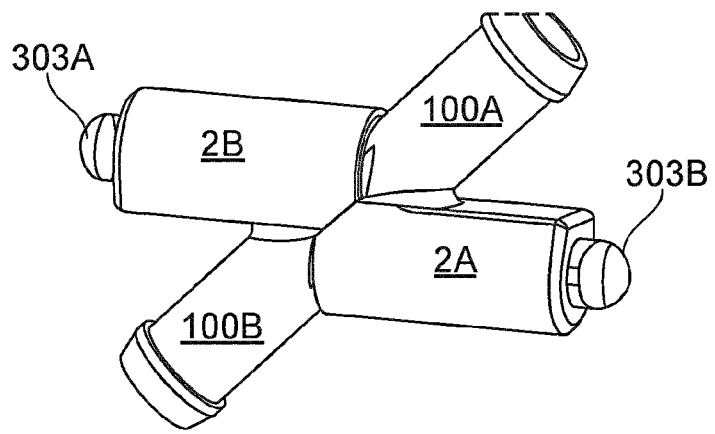

All other parts of the connector (and its reciprocal) are as described above with reference to FIGS. 20a and 20b. FIGS. 23a, 23b and 23c show a series of perspective views of the connector of FIGS. 22a and 22b when connected to a reciprocal such connector are at progressive stages of connection (FIGS. 23a and 23b) and in a final state of full connection (FIG. 23c). FIGS. 24a and 24b show cross-sectional views of the when the connector and reciprocal connector are at the progressive stage (FIG. 24a) of connection shown in FIG. 23b and when in the final state of full connection (FIG. 24b) shown in FIG. 23c.

Figure 26:
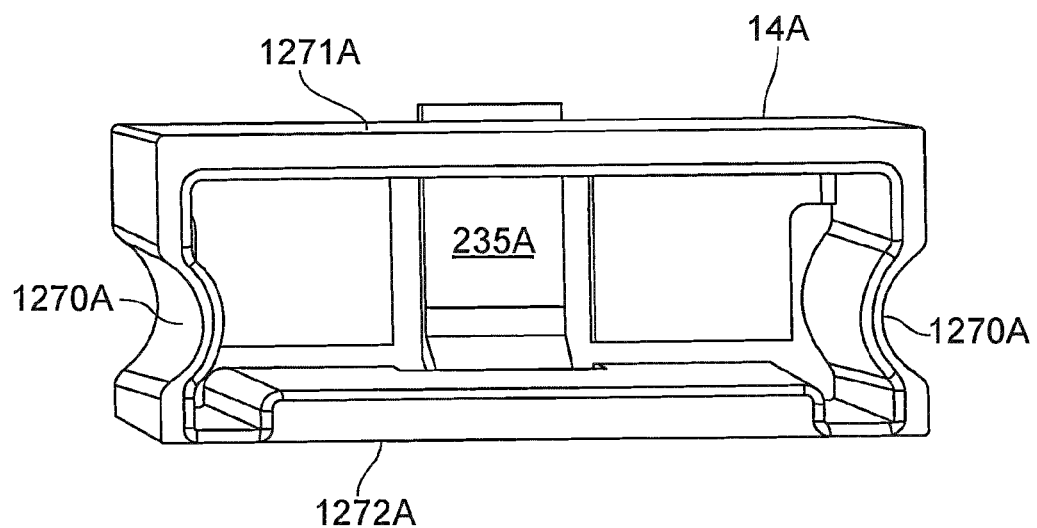
FIG. 26 shows a perspective view of a closure part of a connector.

FIGS. 25a, 25b and 26 show an example of an alternative design of some aspects of the connector described above with reference to FIGS. 13a to 19. As shown in FIG. 25b, the closure part (14A) has two opposing curved side walls (1270A) extending between opposing upper (1272A) and lower (1271A) platform parts of the closure part. The upper and lower platform parts are generally planar and mutually parallel. The upper and lower platform parts are spaced apart from each other in a direction parallel to the longitudinal axis of the fluid flow part (11A, 26A). These upper and lower platform parts form the upper and lower parts of the closure part. The outer surface of the upper platform (1272A) provides a closure surface (e.g. concealment surface) for directly (but displacably) covering the fluid flow opening (26A) of the connector. The top of a respective resiliently deformable curved side wall formation is joined to the upper platform of the closure part, and the other end of the respective resiliently deformable curved side wall formation is joined to the lower platform of the closure part on the same side. The curvature comprises a radius of curvature in a plane which is substantially perpendicular to the longitudinal axis of the closure part and of the bore of the socket part, and which is substantially parallel to the longitudinal axis of the fluid flow part. Each side wall has an inner wall surface facing into the bore of the closure part and having a first radius of curvature, and an outer wall surface facing away from the bore of the closure part and having a second radius of curvature which exceeds the first radius of curvature by an amount that is substantially constant along the arc of the curvature of the respective side wall. This results in a respective side wall of substantially uniform thickness along the arc of curvature of the wall in question. The first and second radii of curvature shares a common centre of curvature such that the arc of the outer wall surface is substantially parallel to the arc of the inner wall surface. This allows the resiliently deformable curved wall formation to curve in a direction transverse to the compressive forces to be experienced by the closure part as it is displaced into the bore of the socket part (12A) of the connector. Consequently, this curvature direction allows the walls (1270A) to resiliently flex, or bow, in response to the compressive forces in question, in a manner sympathetic to the pre-existing curvature of the wall in question, to put into effect the operation of the resilient 'springy' action of the curved wall formations.

FIG. 25a shows the perspective view of the connector (or reciprocal connector) of FIG. 25b, but with the closure part (14A) made absent for improved clarity and to better reveal a pair of parallel ridges (254A) embossed upon a surface of the connector otherwise covered by the closure part (when not displaced) at a location between the fluid flow opening (26A) and the plug part (13A) of the connector. The pair of parallel ridges (254A) comprises two linear parallel ridge lines (255A, 256A) of equal embossed height and embossed thickness, and in the surface between them they define a trough (257A) of uniform depth and width as defined between opposing linear, parallel edges of the two parallel ridge lines. These parallel ridge lines play a role in the aseptic aspect of the invention, in preferred embodiments. In preferred embodiments, the parallel ridge lines press/scrape against the surface of the fluid flow part of the reciprocal connector surrounding the periphery of the fluid flow opening (26B) of that reciprocal connector as it is pushed into register/alignment with the opposing fluid flow opening (26A) of the connector during the act of connecting the connector to the reciprocal connector. This scraping action aims to remove contaminants from the scraped surface.

Figure 27:
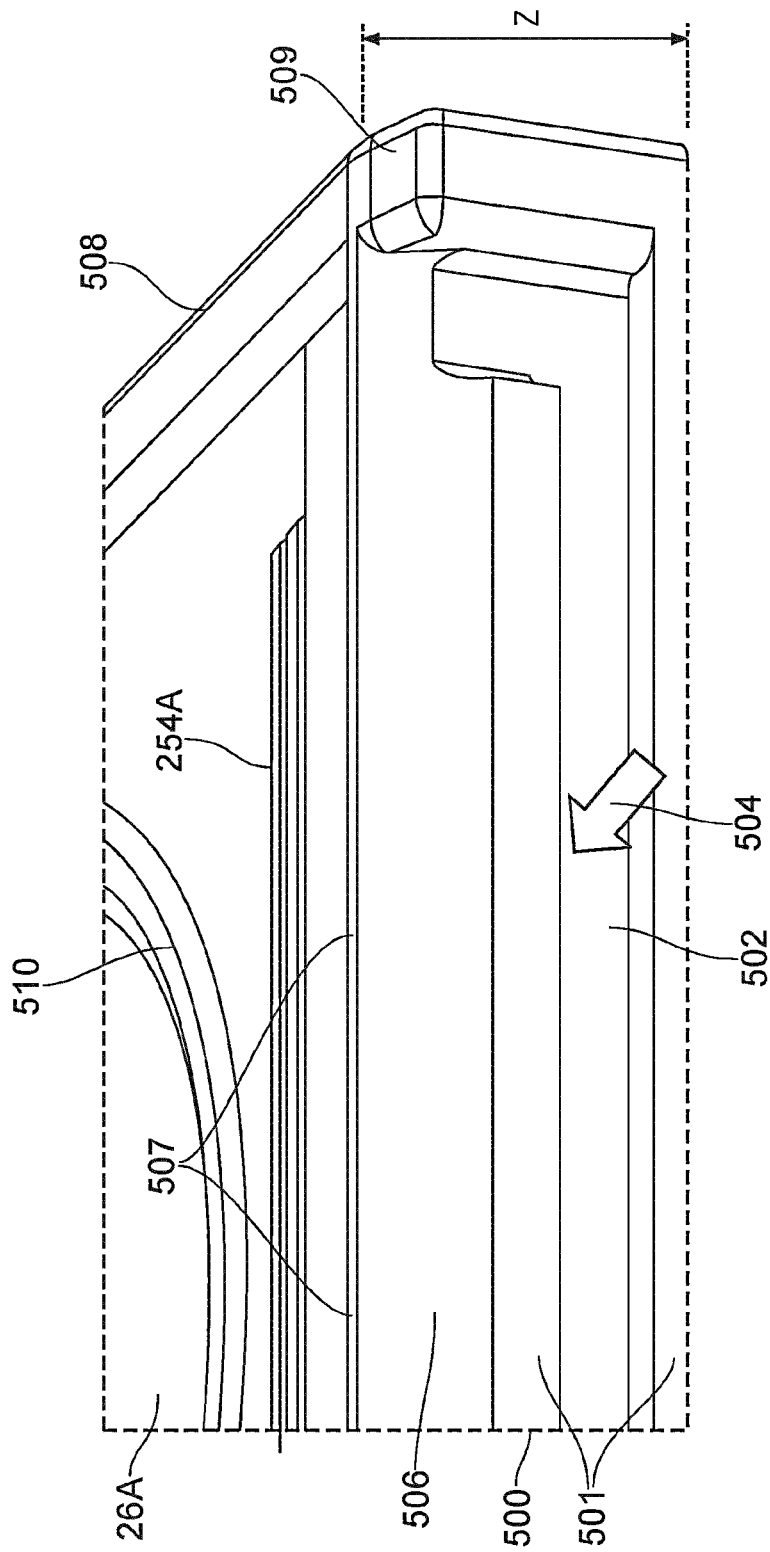
FIG. 27 shows a view of a part of connector including a buffer member.
Figure 28A:
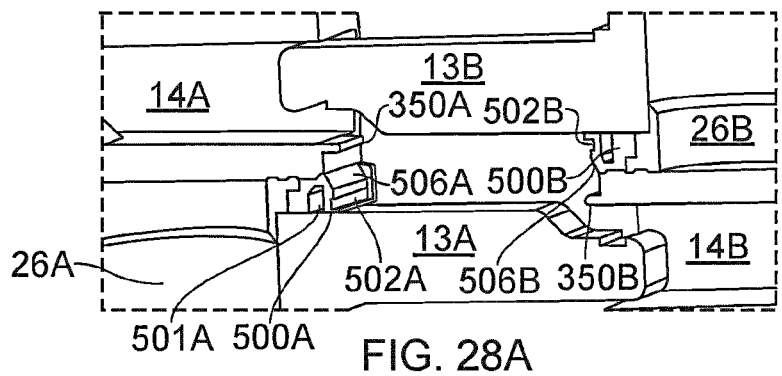
FIGS. 28A, 28B 28C and 28D show cross-sectional views of a process of interconnection of a connector assembly formed from two connectors of FIG. 27.
Figure 28B:
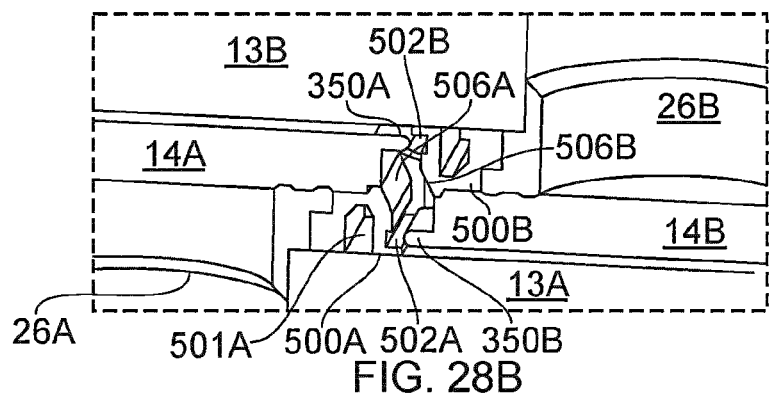
Figure 28C:
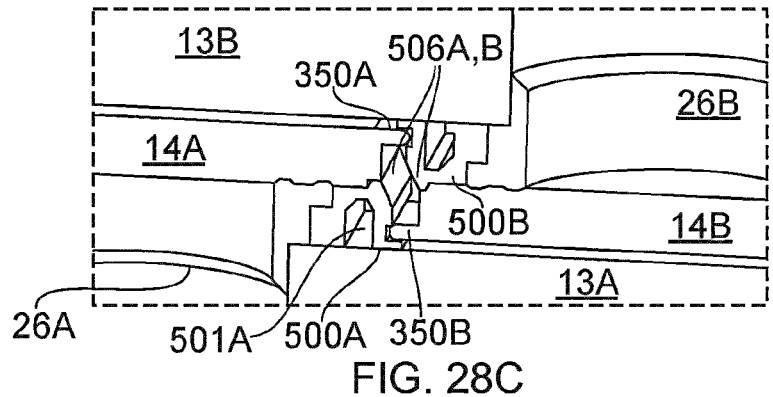
Figure 28D:
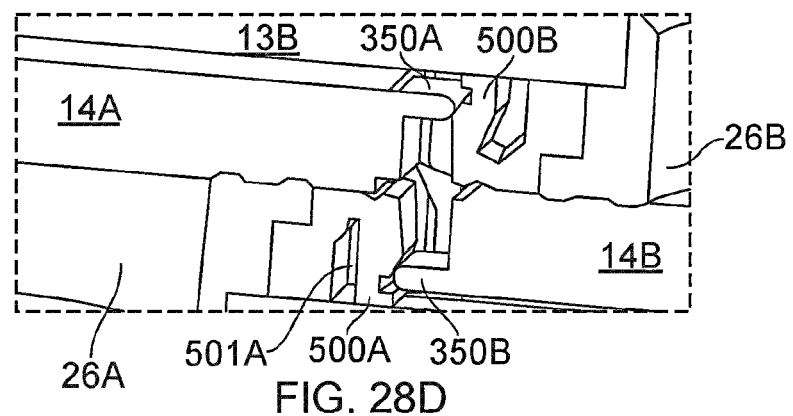

FIG. 27 shows a view of a part of connector as described above, but with the closure part (14A) not shown for clarity, and further including a transverse buffer member (500) attached to the connector along a step formation (258A) of the connector formed by an offset between adjacent surfaces of the connector where the base of the plug part (13A) meets the rest of the connector. The transverse buffer member extends along the whole length of the step formation and is positioned upon surface parts of the plug part (13A) immediately adjacent to the step formation. The height "Z" (see FIGS. 25a and 25b) of the step formation substantially matches the thickness "Z" of the lower platform part (1271A) of the closure part (14A). Similarly, the height "Z" of the transverse buffer member (500) also substantially matches both the height of the step formation and the thickness "Z" of the lower platform part (1271A) of the closure part. In this sense, the transverse buffer member (500) serves as a longitudinal extension of the step formation (258A) over which the lower platform part of the closure part (14B) of a reciprocal connector may slide during the process of connecting the connector part to the reciprocal connector part.

The transverse buffer member is formed from a compressible, compliant and/or resiliently deformable material (e.g., having significant elasticity). It comprises a front face and a back face between which runs a transverse void (501A; FIGS. 28A-D) which extends along the longitudinal axis of the transverse buffer member and extends across, and is exposed to, the opposing surface parts of the plug part (13A) upon which the transverse buffer member is positioned. The opposing surface parts of the plug part (13A) serve to cover the transverse void. The inner edge of the transverse void, closest to the step formation, is positioned to securely abut the corner formed by the step formation where it meets the surface of the plug part (13A), to retain the transverse buffer member. Conversely, the leading edge of the transverse void, furthest from the step formation, is positioned and configured to slide over the surface of the plug part (13A) in a direction towards the inner edge of the transverse void in response to a compressive force (504) applied to it in that direction. The result is to compress the transverse void to narrow the width of the transverse buffer member in the direction of compression, which is perpendicular to the long axis of the buffer member and towards the fluid flow opening (26A).

The transverse buffer member serves as an interface between the step formation on a given connector part, and the lower platform part (1271A) on the closure part of a reciprocal connector. A leading surface of the transverse buffer member comprises an inclined surface part (506), being the part of the leading surface that is closest to (and inclined relative to) to the flat surface of the adjacent lower platform part (1271A) of the closure part of the connector. Contiguous with the inclined surface part is an upright front surface part (501), being the part of the leading surface that is furthest from (and perpendicular relative to) to the flat surface of the lower platform part (1271A) of the connector and closest to the adjacent surface of the plug part (13A) upon which the transverse buffer member is positioned. An outer groove (502) is formed within the upright front surface part (501) and is dimensioned to receive a generally reciprocally-dimensioned tongue part (350B; FIGS. 28A-D) protruding from a leading edge of the closure part (14B) of the reciprocal connector. The location of the outer groove (502) is such that the tongue part (350B) of the closure part (14B;

or reciprocally 14A) of the reciprocal connector becomes aligned in register with the outer groove (502) of the connector when the connector and reciprocal connector are brought together during the act of connecting them as described above. It is during this connecting act, and as a result of the aforementioned alignment in register, that the tongue part of the reciprocal connector is able to apply a compressive force (504) to the transverse buffer member via the outer groove (502) in which it is received, as is shown in the sequence of cross-sectional views of FIGS. 28A-D.

The transverse buffer member also comprises a covered surface part (507; also see 507A and 507B of FIG. 29) which is protectively covered by, and in physical contact with, the closure part (14A) of the connector when the connector is un-connected to a reciprocal connector. In FIG. 27, the closure part (14A) of the connector not shown for clarity, in order to reveal the covered surface part (507). The transverse buffer member is configured such that, as the leading edge of the transverse void slides over the surface of the plug part (13A) in a direction towards the inner edge of the transverse void in response to a compressive force (504) applied to it in that direction, the resulting compression of the transverse void narrows the width of the transverse buffer member with increasing effect at locations thereon that are closer to the opposing surface parts of the plug part (13A). The result is to cause the upright front surface part (501) to tilt towards the surface of the plug part (13A) and to cause the inclined surface part (506) to tilt towards the opposing surface of the closure part (14B) of the reciprocal connector that applies the compressive force (504).

This tilting deformation of the transverse buffer member causes the covered surface part (507; also see 507A and 507B of FIG. 29) to peel away from the protective covering surface of the closure part (14A; or reciprocally 14B) with which it was in physical contact. The inclined surface part (506) ultimately tilts sufficiently towards the opposing surface of the closure part (14B) of the reciprocal connector so that the uppermost boundary of the inclined surface part (506), that is contiguous with the newly-exposed covered surface part (507; also see 507A and 507B of FIG. 29), comes into contact with the opposing surface of the closure part (14B) of the reciprocal connector. The result it that those parts of the leading surface of the transverse buffer member extending between the uppermost boundary of the inclined surface part (506) and the outer groove (502) containing the force-supplying tongue part of the reciprocal connector, are closed-off, sealed-off (e.g., an airtight seal) and contained within a trapped volume defined by the opposing parts of the leading surface of the transverse buffer member and the abutting surface of the closure part (14B) of the reciprocal connector.

A key benefit of this action is to close-off, seal-off and contain any contaminants that may have accumulated upon the surfaces of the connector and the reciprocal connector that are now within the trapped volume and, simultaneously, to reveal clean surfaces (507; also see 507A and 507B of FIG. 29) previously under a protective covering surface of the closure part (14A). Of course, the same principles apply to the corresponding surface parts of the reciprocal connector. This benefit is important in clinical and other applications of the invention, where contamination mitigation is necessary, because the trapped surface parts as well as the clean surface parts of the connectors are subsequently moved in a direction across the openings (26A, 26B) of the fluid flow passageways of the connector and reciprocal connector as the two are urged together during the connection process, as described above and in more detail below.

Prior to being connected, the leading surface parts of the transverse buffer member and the abutting surface of the closure part (14B) are exposed to ambient contaminants. These contaminants might otherwise fall into the openings (26A, 26B) of the fluid flow passageways from either of the contaminated surfaces, during the connection process, if they were not closed-off, sealed-off and contained in this way.

FIGS. 28A, 28B, 28C and 28D show cross-sectional views of the process of interconnection of a connector assembly formed from two connectors of FIG. 27. These figures show a first position (FIG. 28A) in which a connector and a reciprocal connector are aligned immediately prior to connection. One can see that the leading surface parts of the transverse buffer members (500A, 500B) and the exposed surfaces at and around the tongue parts (350A, 350B) of the closure parts (14A, 14B) are exposed to ambient contaminants. In a second position (FIG. 29) in the process of interconnection, plug parts (13A, 13B) are inserted into closure parts (14A, 14B) of the two connectors of the connector assembly. The tongue parts (350A, 350B) of the closure parts (14A, 14B) approach the outer grooves (502) of the transverse buffer members (500A, 500B). The tongue parts (350A, 350B) of the closure parts (14A, 14B) of the reciprocal connectors are aligned in register with the outer grooves (502 of FIG. 27; also see 502A and 502B of FIGS. 28A and 28B) of the connector and reciprocal connector. In a third position (FIG. 28C), the tongue parts (350A, 350B) of the closure parts (14A, 14B) of the reciprocal connectors engage with the outer grooves (502 of FIG. 27; also see 502A and 502B of FIGS. 28A and 28B) of the connector and reciprocal connector. In a fourth position (FIG. 28C), the tongue parts (350A, 350B) of the closure parts (14A, 14B) of the reciprocal connectors press against the outer grooves (502 of FIG. 27; also see 502A and 502B of FIGS. 28A and 28B) of the connector and reciprocal connector to apply a force (504) to them to deform then as described above. This tilting deformation of the transverse buffer members (500A, 500B) causes the covered surface parts (507) to peel away from the protective covering surface of the closure parts (14A, 14B) with which it was in physical contact.

Figure 29:
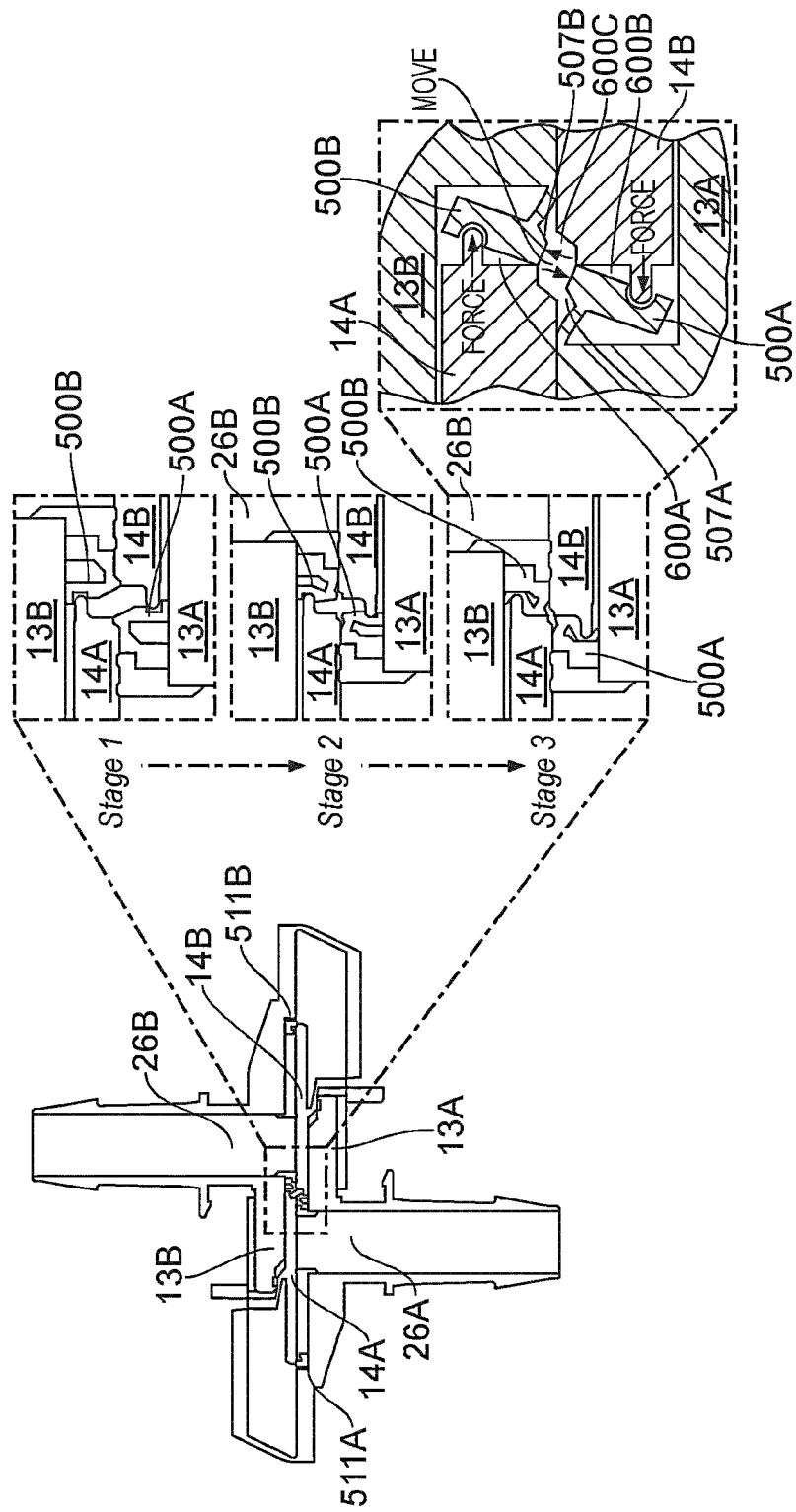
FIG. 29 shows a cross-sectional view of a process of interconnection of a connector assembly formed from two connectors of FIGS. 28A, 28B 28C and 28D.

FIG. 29 shows this process in more detail in similar cross-sectional views of the process of interconnection of a connector assembly. The inset "Stage 1" of FIG. 29 corresponds to the circumstances of the third position shown in FIG. 28C. The inset "Stage 2" of FIG. 29 corresponds to the circumstances of the fourth position shown in FIG. 28D. The inset "Stage 3" of Figure shows a fifth and final position in which the tilting deformation of the transverse buffer member is maximal and the covered surface part (507 of FIG. 27; also see 507A and 507B of FIG. 29) thereof has peeled away from the protective covering surface of the closure part (14A, 14B) with which it was in physical contact. The inclined surface part (506 of FIG. 27; also see 506A and 506B of FIGS. 28A-C) has tilted sufficiently towards the opposing surface of the closure part (14A, 14B) of the adjacent (connected) connector so that the uppermost boundary of the inclined surface part (506 of FIG. 27; also see 506A and 506B of FIGS. 28A-C) comes into contact with the opposing surface of the closure part (14A, 14B) of the adjacent connector. Those parts of the leading surface of the transverse buffer member extending between the uppermost boundary of the inclined surface part (506 of FIG. 27; also see 506A and 506B of FIGS. 28A-C) and the outer groove (502) containing a tongue part (350A, 350B) of an adjacent connector, are closed-off, sealed-off and contained within a trapped volume (600A, 600B). Simultaneously, clean surfaces (600C) previously under a protective covering surface of the closure part (14A, 14B) are revealed.

FIGS. 30A, 30B, 30C and 30D show cross-sectional views of the process of interconnection of a connector assembly formed from two connectors of FIG. 27, and as described above with reference to FIGS. 28A, 28B, 28C, 28D and 29. The stage of connection shown in FIG. 30A corresponds with the circumstances shown in FIG. 29 at "Stage 2". Here, plug parts (13A, 13B) are inserted into closure parts (14A, 14B) of the two connectors of the connector assembly. Simultaneously, a notch part 237A formed within the closure part (14A, 14B) of a given connector (or reciprocal connector) engages with a catch part (13D) formed within the surface of the plug part (13A, 13B) of an adjacent reciprocal connector (or connector) in such a way that the latter may not be retracted from the former.

This means that only onward insertion of the plug part (13A, 13B) into the closure part (14A, 14B) may take place. Such onward insertion progresses the connection process from "Stage 2" to "Stage 3" of FIG. 29 whereby tilting deformation of the transverse buffer members (500A, 500B) ensues and causes the covered surface parts (507 of FIG. 27; also see 507A and 507B of FIG. 29) to peel away from the protective covering surface of the closure parts (14A, 14B) with which it was in physical contact.

At that point in the connection process, the distal end (13C) of the plug part (13A, 13B) of an adjacent reciprocal connector (or connector) abuts against the inner resiliently flexible protruding clip part (235A, and 235B identically on the reciprocal connector) formed across the bore of the closure part (14A, 14B) of the connector (and the reciprocal connector similarly). A notch formation (230A) of the connector (similarly for the reciprocal connector) is formed into which the distal free end of the resiliently flexible protruding clip part protrudes to retain the closure part relative to the connector containing it. Each inner resiliently flexible protruding clip part comprises a resiliently flexible limb which extends across the bore of a closure part from its proximal end which is joined to the closure part, to its distal end/tip which is not joined to anything but is disposed within the notch formation of the socket part containing the closure part in question. When in the un-displaced state, the closure part of the connector (or the reciprocal connector) is positioned such that the distal free tip of the inner resiliently flexible protruding clip part engages with the respective notch formation to retain the closure part in position within the bore of the socket part to cover the fluid flow opening of the connector in question.

Figure 30A:
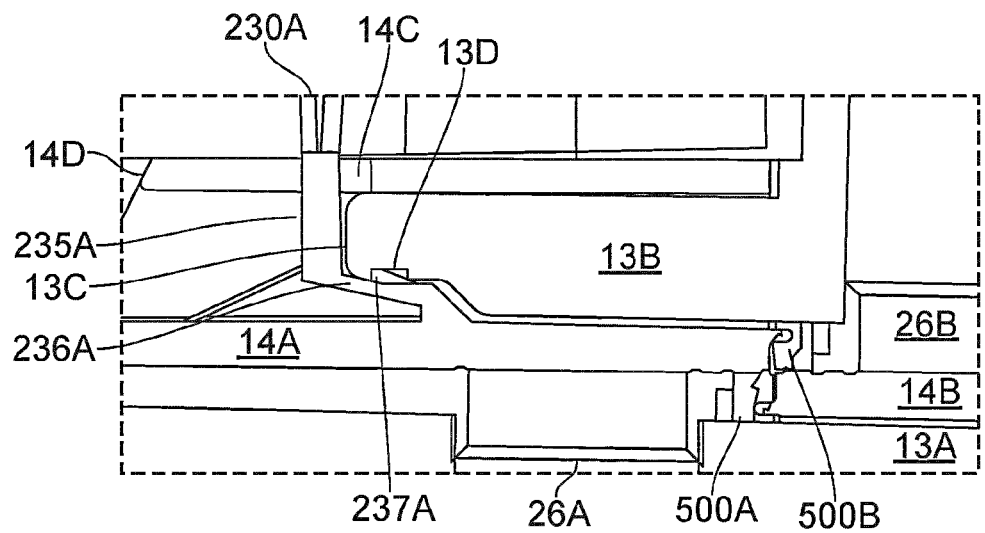
FIGS. 30A, 30B, 30C and 30D show cross-sectional views of a process of interconnection of a connector assembly formed from two connectors of FIG. 29.
Figure 30B:
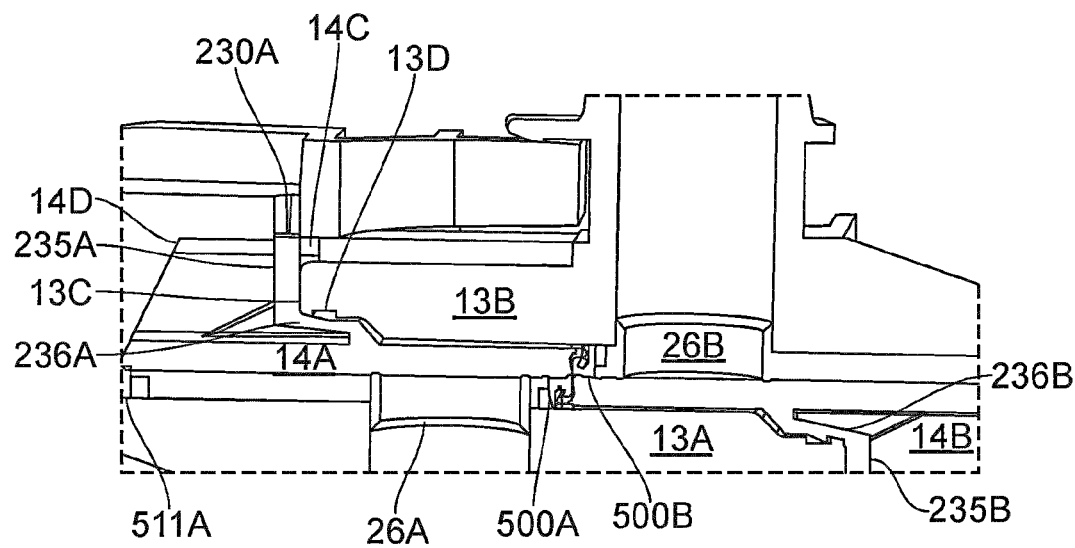

However, upon insertion of a plug part (13A, 13B) of another such connector to such an extent that the terminal end of the inserted plug part presses against the inner resiliently flexible protruding clip part (235A, and 235B identically on the reciprocal connector), as shown in FIG. 30B, internally from within the bore of the closure part. In response to such a pressing or urging force from the abutting plug part, the abutted surface of the inner resiliently flexible protruding clip part is able to rotate about its proximal end so as to displace its distal free tip away from the notch formation (230A). This is achieved by action of the flexing of the closure part at a flexure region (236A, 236B) formed by a relatively thinner portion of the closure part at which proximal end of the inner resiliently flexible protruding clip part is joined to the adjoining portions of the closure part. It this stage, the closure parts (14A, 14B) are free to move along the bore of associated socket parts by being further pushed by plug parts (13A, 13B). This coincides with "Stage 3" shown in FIG. 29.

Figure 30C:
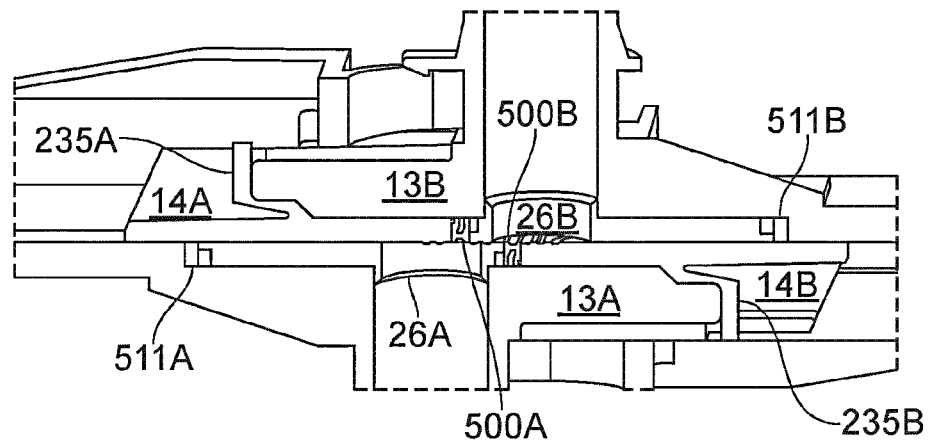
Figure 30D:
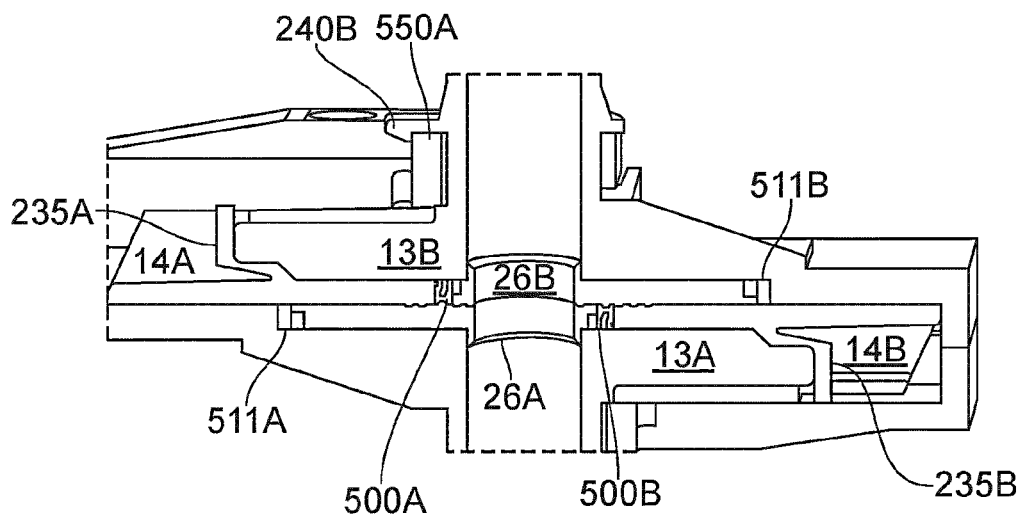

FIGS. 30C and 30D show an intermediate state (FIG. 30C) of this further pushing of closure parts (14A, 14B) by plug parts (13A, 13B) in which the trapped volumes (600A, 600B) are passed across the bores of the fluid flow passageways (26A, 26B) of the connectors, and a final stage (FIG. 30D) in which full connections is achieved and the trapped volumes (600A, 600B) are contained within the connector assembly isolated from the fluid flow passageways (26A, 26B) of the connectors. Simultaneously with achieving this final connection stage, a retaining clip (13E) of the reciprocal connector engages a catch on the connector, and similarly a retaining clip (240B) of the connector engages a catch (550A) on the reciprocal connector, to lock the reciprocal connector to the connector.

FIGS. 31A, 31B, 31C and 31D show views of parts of connectors employed in a process of interconnection of a connector assembly formed from two connectors of FIG. 29. Referring again to FIG. 27, this illustrates a view of one of two parallel longitudinal buffer members (508) each of which enable the formation of side seals concurrently at either longitudinal side of the parts of each connector surrounding its respective fluid flow opening (26A, or reciprocally 26B). The longitudinal buffer members are configured to be resiliently flexible/conformable against the abutting sides of an opposing closure part of the connector while the connector remains unconnected, and to be resiliently flexible/conformable against the abutting surfaces of reciprocal longitudinal buffer members of an opposing a reciprocal connector during and after the process of forming a connection between the two connectors. In particular, longitudinal buffer members are configured to clash with and deform relative to the longitudinal buffer members of an incoming reciprocal connector, thereby forming an outer perimeter seal (e.g., an airtight seal) around the base of the closure part surrounding the respective fluid flow opening (26A, or reciprocally 26B) of the connector in question. This ensures that any tolerance differences in the two connectors are absorbed and a fully closed system is created around the base of the closure part prior to it moving and revealing the internal sealing/contact faces surrounding the fluid flow passageways as those passageways are brought into alignment and contact to form the interconnected fluid flow passageway. This aids the ability of the sides of the closure part to prevent contamination ingress on to the sealing/contact faces as those faces are brought into contact.

A circular ring (510), or rings (250A), is embossed around the fluid flow opening (26A) of the connector. This ring plays a role in the aseptic aspect of the invention, in preferred embodiments. In preferred embodiments, the surface of the fluid flow part of the connector surrounding the periphery of the fluid flow opening (26A, or reciprocally 26B) bears at least one, optionally two (as in FIGS. 18a and 19), or optionally three or more such concentric surface embossments each defining a ring (e.g. circular) of raised surface material of the fluid flow part configured to abut against the opposing surface of the closure part of the connector when the fluid flow opening is closed and the connector is not connected to a reciprocal connector. Such a ring may be considered as a bearing surface against which the corresponding ring of a reciprocal connector may sealingly press when the connector is fully connected to a reciprocal connector, as described above. The pressure with which the ring(s) of one connector bear against the ring(s) of the other connector, when the respective rings are in register, improves the sealing contact interface between them. The longitudinal buffer members (508) collectively with the transverse buffer (500), form an edge buffer assembly extending along a contiguous three edges of the parts of each connector surrounding its respective fluid flow opening (26A, or reciprocally 26B).

The longitudinal buffer members (508) may be formed from the same material as the transverse buffer (500), preferably integrally formed with the transverse buffer as one part, although the longitudinal buffer members may be separate parts formed separately from the transverse buffer with each being an independent insert. The two longitudinal buffer members may preferably meet, or join, the transverse buffer at opposite respective ends of the transverse buffer. The direction of the meeting, or jointing, may be substantially perpendicular to the axis of the transverse buffer, as is shown in the examples. At the corner of the edge buffer assembly defining the location where the outwardly presented bearing surfaces of the transverse buffer and the two longitudinal buffer members meet, the outer surface of the edge buffer assembly is inclined to form a ramp surface part (509) defining a surface region of the edge buffer assembly having an angle of repose intermediate between the angle of repose of the outer surface of the transverse buffer and the angle of repose of the outer surface of the adjacent longitudinal buffer (which may be substantially perpendicular to the surface of the transverse buffer). The ramp surface part (509) is configured to abut the reciprocal ramp surface part of an oncoming reciprocal connector as the two connectors progress through the process of connection together. This is shown in FIG. 34A. The abutment of the two opposing ramp surfaces assists in starting the process of mutual compression of the resiliently compliant material of the longitudinal buffer members as the edge buffer assembly of the connector slide longitudinally along, and against, the opposing longitudinal buffer members of the reciprocal edge buffer assembly of the reciprocal connector.

Figure 31A:
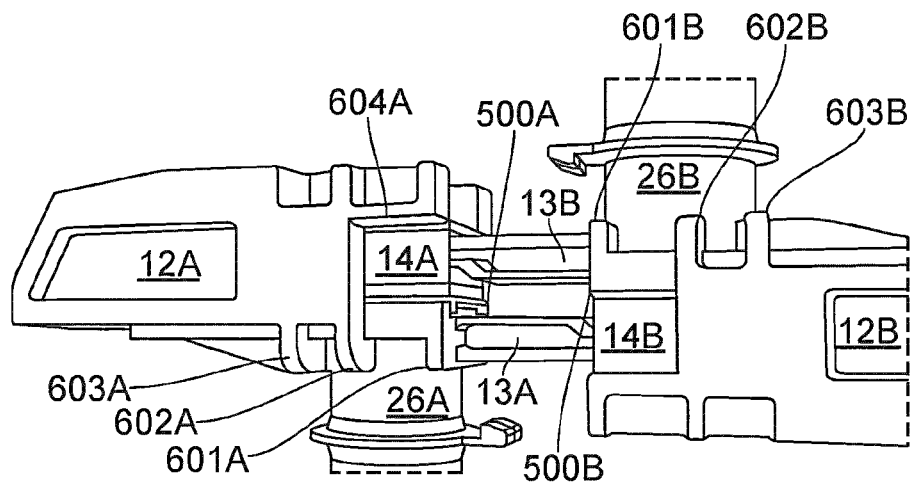
FIGS. 31A, 31B, 31C and 31D show views of parts of connectors employed in a process of interconnection of a connector assembly formed from two connectors of FIG. 29.

FIG. 31A shows two identical connectors each with a respective socket part (12A, or reciprocally 12B) aligned to admit a plug part (13A, or reciprocally 13B) of the other connector into its respective closure part (14A, or reciprocally 14B) to openably close the fluid flow opening (26A, 26B) of the connector and reciprocal connector by receiving an urging force from the received plug part (13A, 13B) of the oncoming connector. The received urging force displaces the closure part (14A, 14B) of the respective connector in a direction crossing the fluid flow opening (26A, 26B) of the connector in question so as to uncover the fluid flow opening of that connector. This is done simultaneously in both connectors, as described above.

The external surface of the socket part of each connector comprises two symmetrically disposed sets of three successive lateral upstand parts (601A, 602A, 603A; or reciprocally 601B, 602B, 603B) each upstanding from the adjacent surface of the socket part in a direction parallel to the axis of the fluid flow passageway of the connector in question. The two sets of lateral upstand parts, and each respective one of the three upstand parts within each set, is disposed symmetrically about opposite lateral sides and about opposite longitudinal sides of the location of the fluid flow passageway of the connector in question. Each lateral upstand part defines a transverse bearing ridge extending in a direction transverse to the longitudinal axis of the socket part of the connector, and the plug part of the connector, and in a direction parallel to the transverse axis of the socket within which the closure part (14A, 14B) resides. The top parts of these transverse bearing ridges define bearing surfaces configured to form sliding bearing interfaces with opposing bearing surfaces of a reciprocal connector part, as discussed below.

A first set of three lateral upstand parts comprises three longitudinally separated upstand parts each located at a first external lateral side of the fluid flow passageway of the connector. A second set of three lateral upstand parts comprises three longitudinally separated upstand parts each located at a second external lateral side (opposite to the first side) of the fluid flow passageway of the connector. Each of the first and second set of three lateral upstand parts comprises a leading upstand part (603A; or reciprocally 603B) located longitudinally between the position of the fluid flow passageway and the position of the plug part, an intermediate upstand part (602A; or reciprocally 602B) longitudinally aligned with the location of the fluid flow passageway, and a trailing upstand part (601A; or reciprocally 601B) located longitudinally such that the position of the fluid flow passageway resides between the positions, respectively, of the plug part (13A; or reciprocally 13B) and the trailing upstand part.

Figure 31B:
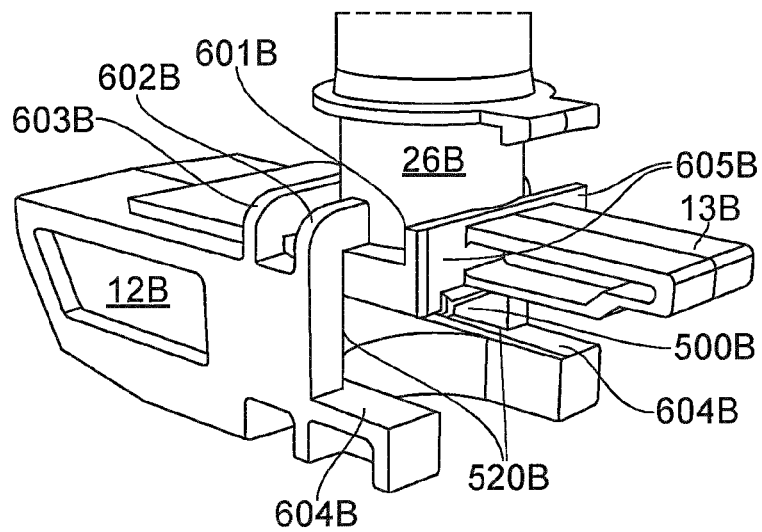
Figure 31C:
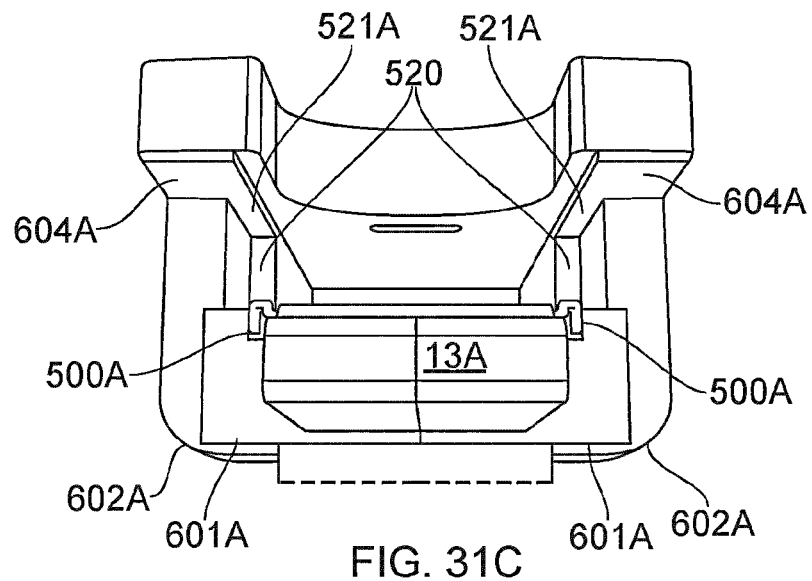
Figure 31D:
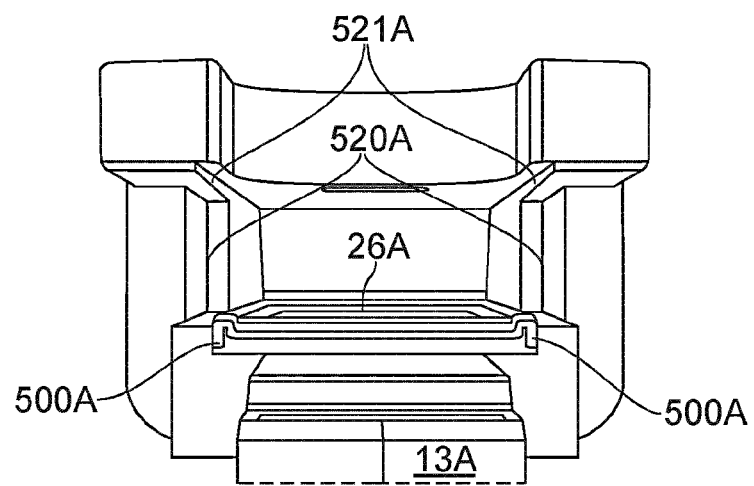

FIGS. 31B, 31C and 31D show views of the socket part (12A; or reciprocally 12B) of a connector in which the closure part (14A, 14B) is omitted to aid clarity. The inner bore of the socket part defines two opposing and mutually parallel bore side walls each located at a respective one of two opposite sides of the longitudinal axis of the fluid flow part (26A, 26B) of the connector, the bore side walls being joined together by two opposing and mutually parallel bore main walls spaced-apart by the bore side walls. The inner surface of each side wall defines a longitudinally extending bearing groove (520B, 520A) having a groove height, in the dimension parallel to the axis of the fluid flow passageway, that reduces at increasing locations along the bearing groove away from the location of the fluid flow opening. In this way, the bearing groove tapers so as to narrow as one progresses along the groove into the socket part. In particular, a surface (521A) of the bore main wall that is opposite to the main bore wall containing the fluid flow opening (i.e., the bore main wall that does not possess the fluid flow opening 26A), and which forms a boundary of the longitudinally extending bearing groove, is inclined relative to the plane of the surface of the opposing main bore wall containing the fluid flow opening (i.e., the bore main wall that does possess the fluid flow opening 26A). As a result, parts of the longitudinally extending bearing groove longitudinally deeper within the groove are closer to the opposing main bore wall than are parts of the longitudinally extending bearing groove that are not as deep within the groove.

Figure 32A:
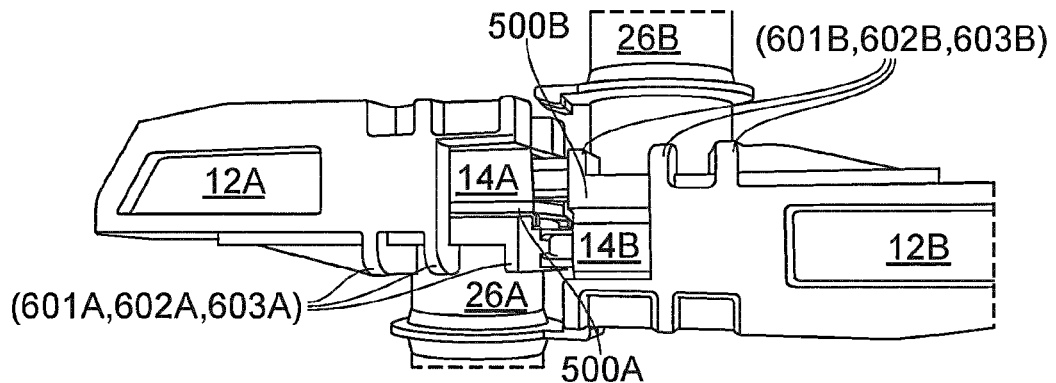
FIGS. 32A, 32B, 32C, 32D and 32E show views of two connectors in successive positions in a process of interconnection of a connector assembly formed from two connectors of FIG. 29.
Figure 32B:
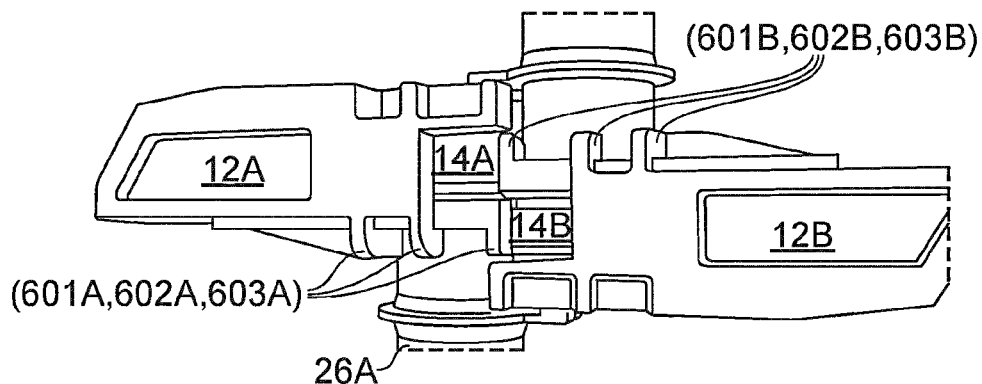
Figure 32C:
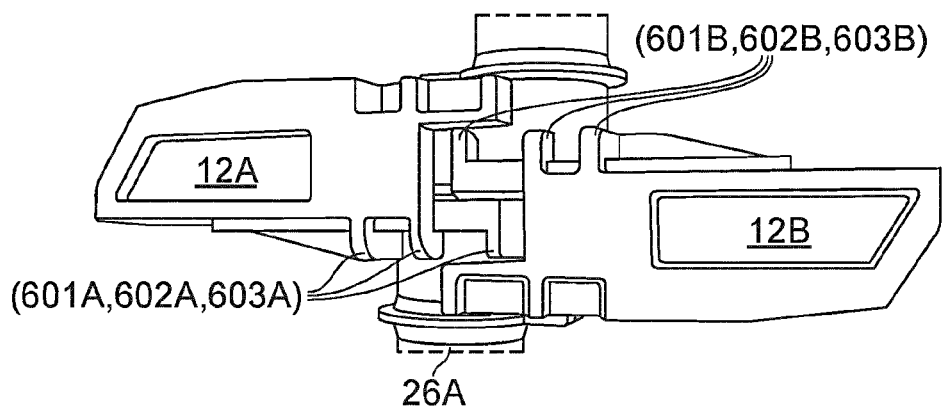
Figure 32D:
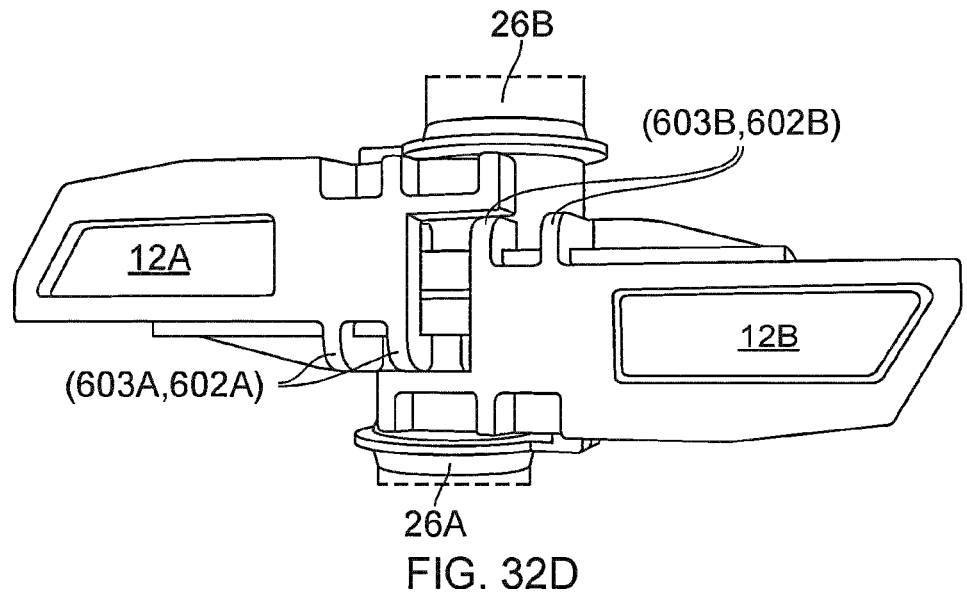
Figure 32E:
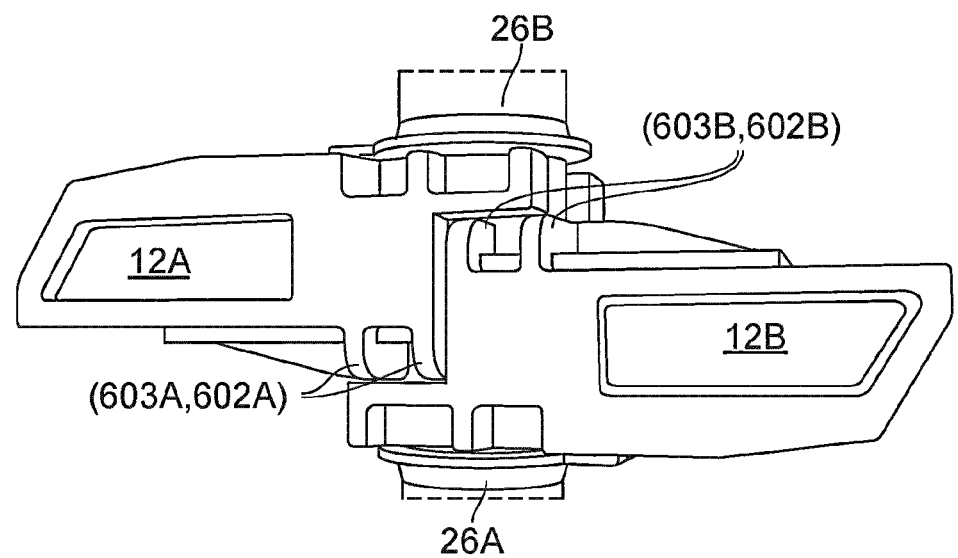
Figure 33A:
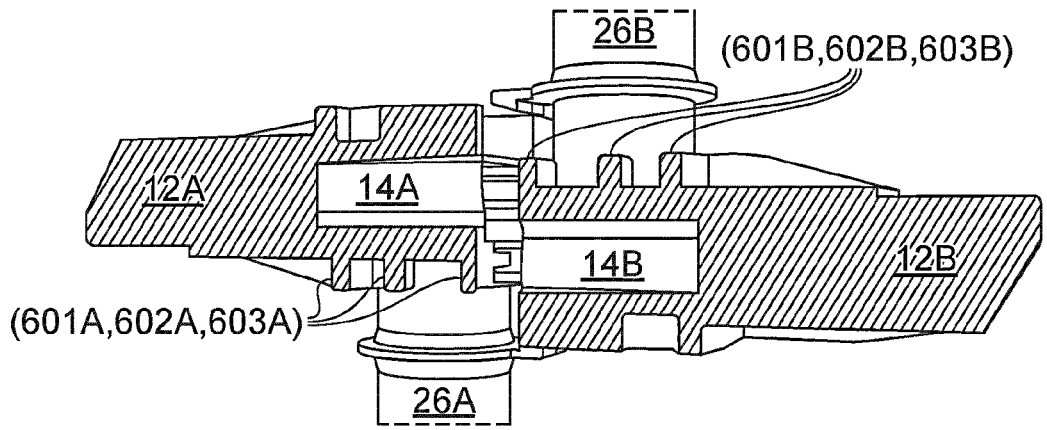
FIGS. 33A, 33B, 33C, 33D and 33E show cross-sectional views of the two connectors in successive positions shown in FIGS. 32A, 32B, 32C, 32D and 32E.
Figure 33B:
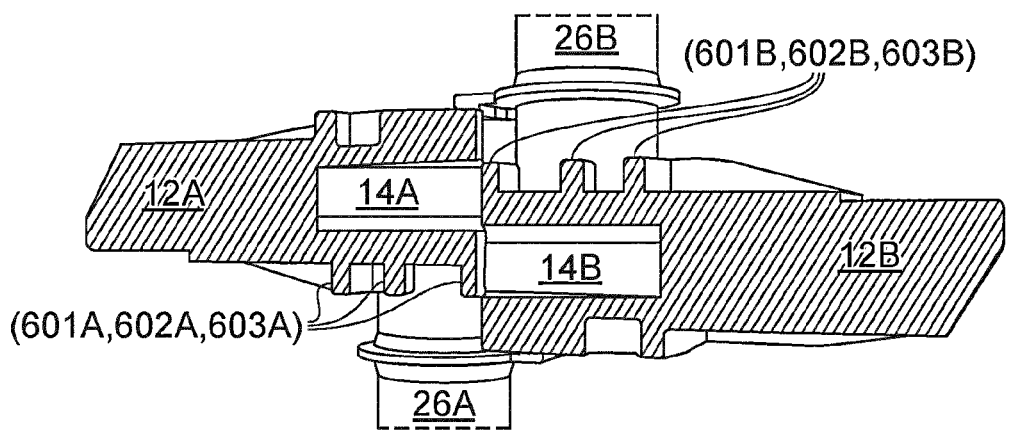
Figure 33C:
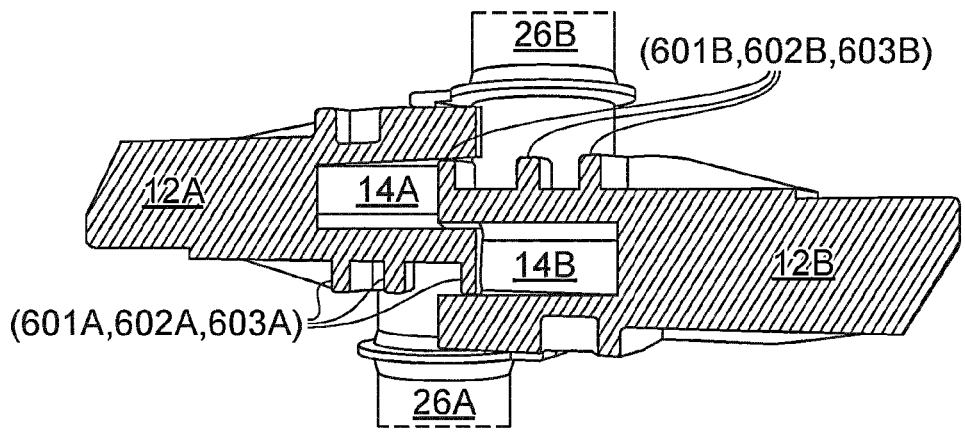
Figure 33D:
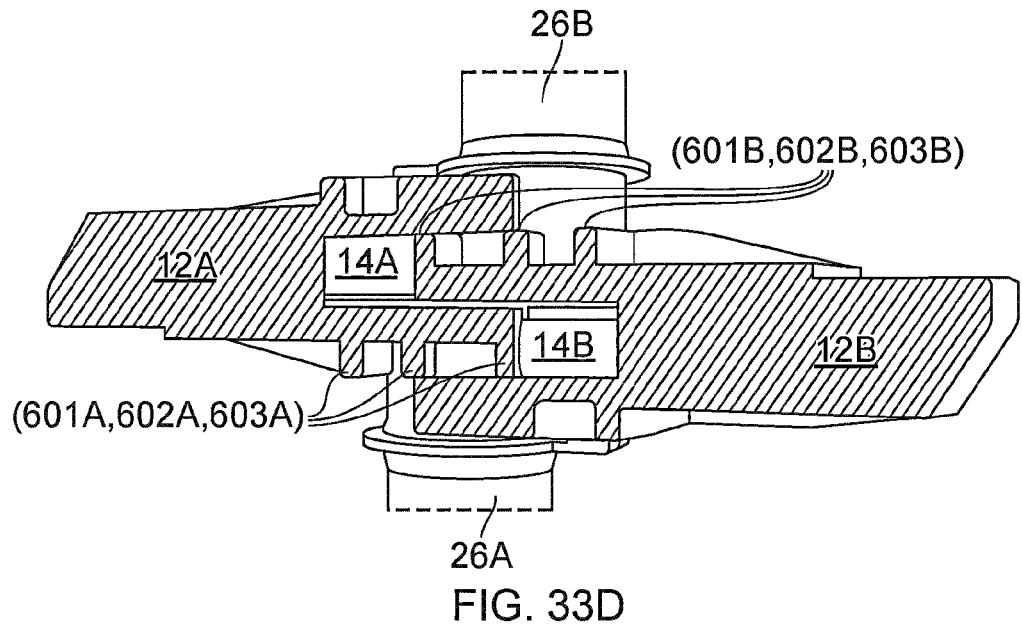
Figure 33E:
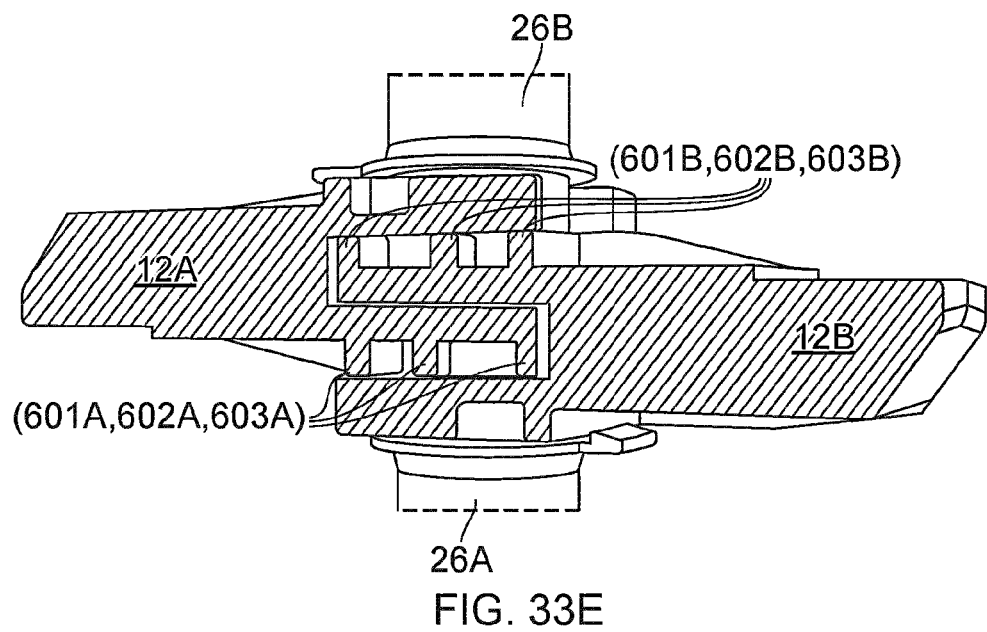

The height and position of the inclined surface of each one of the two longitudinally extending bearing grooves (520B, 520A) in a given connector, is configured to receive and slidingly bear against the bearing edge a respective one of the two leading upstand parts (601A; or reciprocally 601B) of an oncoming reciprocal connector during the connection process. In addition, the inclined surface of each one of the two longitudinally extending bearing grooves (520B, 520A) extends beyond the opening of the respective groove so as to form an overhang surface part (604A, 604B) of the bore main wall not containing the fluid flow opening (i.e., the bore main wall that does not possess the fluid flow opening 26A). These inclined bearing surface extensions are each configured to slidingly bear against the bearing edge of the two intermediate upstand part and the trailing upstand part (603A; or reciprocally 603B) of a respective one of the two sets of three upstand parts of an oncoming reciprocal connector during the connection process. Consequently, as is shown in the sequence of perspective views of FIGS. 32A, 32B, 32C, 32D and 32E, illustrating perspective views of two connectors in successive positions in a process of interconnection of a connector assembly, and as is shown in the corresponding sequence of cross-sectional views of FIGS. 33A, 33B, 33C, 33D and 33E show cross-sectional views of the two connectors in successive positions shown in FIGS. 32A, 32B, 32C, 32D and 32E, the leading upstand parts enter inside the ramped groove of the socket part socket and will abut against and slide along the internal ramp surface (521A,B). In FIG. 32A and 33A, the two connectors are about to engage respective ramping surfaces and upstand edges. In FIGS. 32B and 33B, the two connectors have moved in a purely horizontal direction into a position in which the two leading upstands (601A, 601B) of each connector engage with the inclined surfaces of each one of the two longitudinally extending bearing grooves (520B, 520A) of the other connector. Onward movement to push the two connectors further together causes an increasing squeezing together of the two connectors in a direction parallel to the fluid flow axes of each, thereby pushing the longitudinal buffer members of one connector against the opposing longitudinal buffer members of the other connector to begin to form a sealing interface between them. This is shown in the onward pushing together of the connectors as illustrated in FIG. 32C and 33C FIG. 32D and 33D, and then FIG. 32E and 33E, show the point at which the following two upstands (the intermediate upstand part and the trailing upstand part) abut against and slide along the external ramp surfaces (604A,B) of the connectors. FIG. 32D and 33D show the abutment of the intermediate bearing edges (602A, 602B) which occurs simultaneously for both the connector and the reciprocal connector such that as the two are pushed together, as the intermediate bearing edges of the one connector slidingly bear against the external ramped bearing surface of the reciprocal connector, they apply a compression force which further compress the longitudinal buffer members of one connector against the opposing longitudinal buffer members of the other connector and also compresses together opposing parts of respective circular rings (510) embossed around the fluid flow openings (26A, 26B) of the two connectors. FIG. 32E and 33E show the abutment of the trailing bearing edges (603A, 603B) which occurs simultaneously for both the connector and the reciprocal connector.

In the way, movement of the two connectors together is initially in a direction perpendicular to the fluid flow axis of each. When the leading upstand parts (601A,B) enter the reciprocal connector socket part, as shown in FIG. 34B, they will soon start to rub against the internal ramp section (521A,B) which will start the ramping down process at an inclination angle of about 3.0 degrees. Here the intermediate upstand parts (602A,B) come in to play and rub against the external ramp surfaces (604A,B), quickly followed by the trailing upstand parts (603A,B) to help confirm the ramping angle of about 3.0 degrees. It is to be understood that the ramping angle may be between about 1.0 degree and 5.0 degrees, or more preferably between 2.0 and 4.0 degrees, such as about 3.0 degrees.

In preferred aspects of the invention, a connector may comprise an inner transverse buffer member (511A, 511B: FIGS. 29, 30B-D) located within a surface region of the bore of the socked part (12A, 12B) that is substantially coplanar with the surface region of the connector along which (or adjacent which) the outer transverse buffer member (500) is located. The inner transverse buffer member is located at one side of the fluid flow opening (26A, 26B) opposite to the side at which both the plug part (13A, 13B) and the outer transverse buffer member are located. The inner transverse buffer member is configured to be resiliently flexible/conformable against the abutting surface of the base of an opposing closure part (14A, 14B) of the connector both while the connector remains unconnected, and during and after the process of forming a connection with a reciprocal connector. In particular, the inner transverse buffer member is configured to slidingly abut and deform against the opposing surface of the closure part whether that opposing closure part is stationary or moving along the bore of the socket part (12A, 12B) in response to forces from an inserted plug part (13A, 13B) of an oncoming reciprocal connector during the process of connecting the two connectors. This contributes to forming an outer perimeter seal (e.g., an airtight seal) around the base of the closure part (14A, 14B) surrounding the respective fluid flow opening (26A, or reciprocally 26B) of the connector in question.

The inner transverse buffer (511) may be formed from the same material as the two longitudinal buffer members (508) and may be integrally formed with the two longitudinal buffer members as one part. Alternatively, the inner transverse buffer (511) may be a separate part formed separately from the two longitudinal buffer members (508), e.g., as an independent insert. The inner transverse buffer member may preferably meet, or join, the two longitudinal buffer members at opposite respective ends of the inner transverse buffer. The direction of the axis of the inner transverse buffer member may be substantially perpendicular to the axis of the two longitudinal buffer members, as is shown in the examples.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described. Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps. It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The invention claimed is:

1. A genderless connector adapted for forming a fluid flow pathway therethrough by connection with a genderless reciprocal connector, wherein both the connector and the reciprocal connector each comprise:
a fluid flow passageway part defining a fluid flow opening;
a socket part located upon the fluid flow passageway part adjacent to the fluid flow opening;
a plug part located upon the fluid flow passageway part adjacent to the fluid flow opening and spaced from the socket part such that the plug part and the socket part are located upon the fluid flow passageway part adjacent to opposite respective sides of the fluid flow opening, being separated in a direction transverse to an axis of the fluid flow passageway part, wherein the socket part of the connector is configured to receive therein the plug part of said reciprocal connector to connect thereto such that the fluid flow opening of the connector is aligned in register with the fluid flow opening of the reciprocal connector; and,
a closure part arranged to openably close the fluid flow opening of the connector and to receive an urging force from said received plug part of the reciprocal connector thereby to be displaced in said direction crossing the fluid flow opening transversely to said axis of the fluid flow passageway part thereby uncovering the fluid flow opening such that the connector is thereby connectable to the reciprocal connector with respective fluid flow openings in fluid communication;
a releasable catch mechanism operable to change from a first state in which the releasable catch mechanism prevents displacement of the closure part relative to the socket part thereby to retain the closure part in a position closing the fluid flow opening, to a second state in which the releasable catch mechanism permits said displacement of the closure part and said uncovering of the fluid flow opening;
wherein the releasable catch mechanism comprises an abutment surface configured for abutment by the plug part of the reciprocal connector thereby to receive a pressing force from the plug part when the plug part of the reciprocal connector is received within the socket part of the connector, for actuation of the releasable catch mechanism by the plug part of the reciprocal connector from within the socket part of the connector whereby the state of the releasable catch mechanism is operable to change from said first state to said second state in response to said pressing force from the plug part during abutment between the releasable catch mechanism and the plug part of said reciprocal connector thereby to change from said first state to said second state by action of receiving the plug part of the reciprocal connector within the socket part of the connector.

2. A genderless connector according to claim 1 wherein the socket part of the connector comprises the abutment surface of the releasable catch mechanism.

3. A genderless connector according to claim 1 wherein the closure part of the connector comprises the abutment surface of the releasable catch mechanism.

4. A genderless connector according to claim 1 wherein the closure part comprises a bearing surface configured for receiving said urging force from the plug part of said reciprocal connector when received within the socket part of the connector not before said releasable catch mechanism has changed from said first state to said second state.

5. A genderless connector according to claim 1 wherein the socket part thereof defines a bore for receiving the plug part of the reciprocal connector, whereby the diameter of an opening of the bore exceeds an internal diameter of the bore which abuts against the plug part of the reciprocal connector when received therein to urge the fluid flow passageway part of the connector towards the fluid flow passageway part of the reciprocal connector.

6. A genderless connector according to claim 1 wherein the plug part and the socket part are located upon the fluid flow passageway part adjacent to opposite respective sides of the fluid flow opening, being separated in a direction axially along the axis of the fluid flow passageway part.

7. A genderless connector according to claim 1 wherein the fluid flow opening, the socket part and the plug part of both the connector and the reciprocal connector are configured such that the connector is connectable to the reciprocal connector to position the axis of respective fluid flow passageways thereof in mutually coaxial alignment.

8. A genderless connector according to claim 1 wherein the plug part of the connector is configured for insertion into the socket part of the reciprocal connector to connect thereto such that the fluid flow passageway part of the connector is urged against the fluid flow passageway part of the reciprocal connector to urge respective fluid flow openings together.

9. A genderless connector according to claim 1 wherein the closure part comprises a concealment surface portion which is disposed to overlay the fluid flow opening.

10. A genderless connector according to claim 9 wherein the closure part is resiliently deformable and compressed within the socket part to resiliently urge the concealment surface against the fluid flow passageway parts surrounding the peripheral edge of the fluid flow opening.

11. A genderless connector according to claim 9 wherein the concealment surface portion comprises a surface relief ramp formation configured to project therefrom through the fluid flow opening and into the fluid flow passageway whereby said displacement in said direction crossing the fluid flow opening causes the surface relief ramp formation to ride over an abutting peripheral edge of the fluid flow opening thereby to displace the concealment surface portion in a direction away from the fluid flow opening.

12. A genderless connector according to claim 11 wherein the surface relief ramp formation extends along the concealment surface to define a shape reciprocating the shape of a peripheral edge of the fluid flow opening.

13. A genderless connector according to claim 11 wherein the closure part is resiliently deformable to compress resiliently in a direction away from the fluid flow opening in response to the surface relief ramp formation riding over an abutting peripheral edge of the fluid flow opening.

14. A genderless connector assembly comprising a pair of connectors each being according to claim 1 and wherein any one connector of the pair of connectors is a said reciprocal connector for the other connector of the pair of connectors.

15. A method for forming a fluid flow pathway comprising the steps of:
providing a genderless connector assembly according to claim 14;

connecting the connector to the reciprocal connector with respective fluid flow openings in fluid communication.

\* \* \* \* \*